United States Patent
Hu et al.

(10) Patent No.: US 10,766,878 B2
(45) Date of Patent: Sep. 8, 2020

(54) SULFONYLCYCLOALKYL CARBOXAMIDE COMPOUNDS

(71) Applicant: Genentech, Inc., South San Francisco, CA (US)

(72) Inventors: Baihua Hu, Beijing (CN); Vishal Verma, South San Francisco, CA (US); Matthew Volgraf, South San Francisco, CA (US); Anthony Estrada, San Mateo, CA (US); Joseph Lyssikatos, Piedmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/247,995

(22) Filed: Jan. 15, 2019

(65) Prior Publication Data
US 2019/0144430 A1    May 16, 2019

Related U.S. Application Data

(63) Continuation of application No. PCT/EP2017/068171, filed on Jul. 18, 2017.

(51) Int. Cl.

| | | |
|---|---|---|
| *C07D 403/04* | (2006.01) | |
| *C07D 401/04* | (2006.01) | |
| *C07D 231/12* | (2006.01) | |
| *C07D 237/08* | (2006.01) | |
| *C07D 213/61* | (2006.01) | |
| *C07D 231/16* | (2006.01) | |
| *C07D 231/20* | (2006.01) | |
| *C07D 239/26* | (2006.01) | |

(52) U.S. Cl.
CPC .......... *C07D 403/04* (2013.01); *C07D 213/61* (2013.01); *C07D 231/12* (2013.01); *C07D 231/16* (2013.01); *C07D 231/20* (2013.01); *C07D 237/08* (2013.01); *C07D 239/26* (2013.01); *C07D 401/04* (2013.01)

(58) Field of Classification Search
CPC . A61P 11/00; A61P 11/06; A61P 11/14; A61P 13/00; A61P 13/02; A61P 17/04; A61P 17/06; A61P 19/02; A61P 1/00; A61P 25/00; A61P 25/02; A61P 27/16; A61P 29/00; A61P 43/00; C07D 213/61; C07D 231/16; C07D 231/12; C07D 231/20; C07D 237/08; C07D 239/26; C07D 401/04; C07D 403/04
See application file for complete search history.

(56) References Cited

FOREIGN PATENT DOCUMENTS

| | | | |
|---|---|---|---|
| WO | 2010/141805 A1 | 12/2010 | |
| WO | WO 2010/141805 | * 12/2010 | .......... C07D 207/48 |
| WO | 2015/052264 A1 | 4/2015 | |
| WO | 2016/128529 A1 | 8/2016 | |
| WO | 2018/015410 A1 | 1/2018 | |
| WO | 2018/029288 A1 | 2/2018 | |

OTHER PUBLICATIONS

"International Preliminary Report on Patentability—PCT/EP2017/068171":pp. 1-7 (Jan. 31, 2019).
"International Search Report—PCT/EP2017/068171":pp. 1-11 (Aug. 25, 2017).

* cited by examiner

*Primary Examiner* — Erich A Leeser
(74) *Attorney, Agent, or Firm* — Robert C. Hall

(57) ABSTRACT

The invention is concerned with the compounds of formula I:

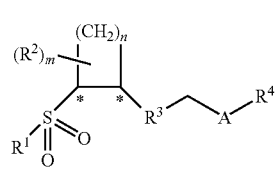

and pharmaceutically acceptable salts thereof. In addition, the present invention relates to methods of manufacturing and methods of using the compounds of formula I as well as pharmaceutical compositions containing such compounds. The compounds may be useful in treating diseases and conditions mediated by TRPA1, such as pain.

23 Claims, No Drawings

SULFONYLCYCLOALKYL CARBOXAMIDE COMPOUNDS

CROSS-REFERENCE TO RELATED APPLICATION

This application is a Continuation of PCT/EP2017/068171 filed Jul. 18, 2017, which claims the benefit of priority to International Patent Application No. PCT/CN2016/090637 filed 20 Jul. 2016, the contents of which application is hereby incorporated by reference in their entirety.

FIELD OF THE INVENTION

The invention relates to sufonyl cyclobutyl and cyclopentyl carboxamine compounds, their manufacture, pharmaceutical compositions containing them and their use as Transient Receptor Potential (TRP) channel antagonists.

BACKGROUND OF THE INVENTION

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor.'

Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation. Moreover, recently findings have correlated activation of TRPA1 channels with increased pain perception (Kosugi et al., *J. Neurosci* 27, (2007) 4443-4451; Kremayer et al., *Neuron* 66 (2010) 671-680; Wei et al., *Pain* 152 (2011) 582-591; Wei et al., *Neurosci Lett* 479 (2010) 253-256)) providing additional rationale for the utility of small molecule TRPA1 inhibitors in the treatment of pain disorders.

SUMMARY OF THE INVENTION

In some embodiments, a compound or a pharmaceutically acceptable salt thereof of the following formula (I) is provided:

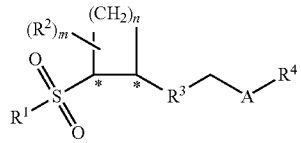

wherein n is 2 or 3. $R^1$ is aryl or heteroaryl, each optionally substituted with one or more groups independently selected from halogen, —$C_{1-6}$ alkyl and —$C_{1-6}$ haloalkyl. m is 0, 1, 2, or 3 and each $R^2$ is independently selected from halogen, —$C_{1-6}$ alkyl, —$C_{1-6}$ haloalkyl, —O—$C_{1-6}$ alkyl, —$C_{3-7}$ cycloalkyl, and —CN. $R^3$ is an amide selected from the orientation —NH—C(O)— and —C(O)—NH—. $R^4$ is a 4, 5, 6 or 7-membered heterocycle, aryl or heteroaryl optionally substituted with one or more groups independently selected from halogen, $C_{1-6}$ alkyl, $C_{1-6}$ haloalkyl, O—$C_{1-6}$ haloalkyl, and —CN. A is selected from $A^1$, $A^2$ and $A^3$ wherein: $A^1$ is unsubstituted or substituted 5-membered heteroaryl comprising one or two nitrogen hetero atoms; $A^2$ is unsubstituted or substituted aryl; and $A^3$ is unsubstituted or substituted 6-membered heteroaryl comprising one or two hetero nitrogen atoms. Each * represents a chiral center (i) in an R configuration or in an S configuration or (ii) a mixture of R and S configurations for a plurality of compounds of formula (I) or a pharmaceutically acceptable salt thereof.

In some embodiments, a pharmaceutical composition comprising a compound of formula (I) or a pharmaceutically acceptable salt thereof, and a pharmaceutically acceptable carrier, diluent or excipient is provided.

In some embodiments, a compound of formula (I) or a pharmaceutically acceptable salt thereof is provided for use in medical therapy.

In some embodiments, a compound of formula (I) or a pharmaceutically acceptable salt thereof is provided for use in the treatment or prophylaxis of a respiratory disorder.

In some embodiments, a compound of formula (I) or a pharmaceutically acceptable salt thereof is provided for the preparation of a medicament for the treatment or prophylaxis of a respiratory disorder.

In some embodiments, a method for treating a respiratory disorder in a mammal is provided, the method comprising, administering a compound of formula (I) or a pharmaceutically acceptable salt thereof to the mammal.

In some embodiments, a compound of formula (I) or a pharmaceutically acceptable salt thereof is provided for modulating TRPA1 activity.

In some embodiments, a compound of formula (I) or a pharmaceutically acceptable salt thereof is provided for the treatment or prophylaxis of a disease or condition mediated by TRPA1 activity.

In some embodiments, a compound of formula (I) or a pharmaceutically acceptable salt thereof is provided for use for the preparation of a medicament for the treatment or prophylaxis of a disease or condition that is mediated by TRPA1 activity.

In some embodiments, a method for modulating TRPA1 activity is provided, the method comprising contacting TRPA1 with a compound of formula (I) or a salt thereof.

In some embodiments, a method for treating a disease or condition mediated by TRPA1 activity in a mammal is provided, the method comprising administering a compound of formula (I) or a pharmaceutically acceptable salt thereof to the mammal.

DETAILED DESCRIPTION OF THE INVENTION

Definitions

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ to $R^5$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms. In particular embodiments the alkyl has 1 to 6 carbon atoms.

"Aryl" means a cyclic aromatic hydrocarbon moiety having a mono-, bi- or tricyclic aromatic ring of 5 to 16 carbon ring atoms. The aryl group can be optionally substituted as defined herein. Examples of aryl moieties include, but are not limited to, phenyl, naphthyl, phenanthryl, fluorenyl, indenyl, pentalenyl, azulenyl, and the like, The term "aryl" also includes partially hydrogenated derivatives of the cyclic aromatic hydrocarbon moiety provided that at least one ring of the cyclic aromatic hydrocarbon moiety is aromatic, each being optionally substituted. In one embodiment the aryl has 6 to 14 carbon ring atoms (i.e., ($C_6$-$C_{14}$) aryl). In another embodiment the aryl has 6 to 10 carbon ring atoms (i.e., ($C_6$-$C_{10}$)aryl)

The term "heteroaryl" denotes an aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein one or more of the hydrogen atoms of the alkyl group has been replaced by the same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a saturated or partially unsaturated carbocyclic moiety having mono- or bicyclic (including bridged bicyclic) rings and 3 to 10 carbon atoms in the ring. The cycloalkyl moiety can optionally be substituted with one or more substituents. In particular embodiments cycloalkyl contains from 3 to 8 carbon atoms (i.e., ($C_3$-$C_8$) cycloalkyl). In other particular embodiments cycloalkyl contains from 3 to 6 carbon atoms (i.e., ($C_3$-$C_6$)cycloalkyl). Examples of cycloalkyl moieties include, but are not limited to, cyclopropyl, cyclobutyl, cyclopentyl, cyclohexyl, cycloheptyl, and partially unsaturated (cycloalkenyl) derivatives thereof (e.g. cyclopentenyl, cyclohexenyl, and cycloheptenyl). The cycloalkyl moiety can be attached in a "spirocycloakyl" fashion such as "spirocyclopropyl":

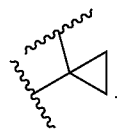

"Heterocycle" or "heterocyclyl" refers to a 4, 5, 6 and 7-membered monocyclic or 7, 8, 9 and 10-membered bicyclic (including bridged bicyclic) heterocyclic moiety that is saturated or partially unsaturated, and has one or more (e.g., 1, 2, 3 or 4 heteroatoms selected from oxygen, nitrogen and sulfur in the ring with the remaining ring atoms being carbon. When used in reference to a ring atom of a heterocycle, a nitrogen or sulfur may also be in an oxidized form, and a nitrogen may be substituted with one or more ($C_1$-$C_6$)alkyl or groups. The heterocycle can be attached to its pendant group at any heteroatom or carbon atom that results in a stable structure and any of the ring atoms can be optionally substituted. Examples of such saturated or partially unsaturated heterocycles include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term the term heterocycle also includes groups in which a heterocycle is fused to one or more aryl, heteroaryl, or cycloalkyl rings, such as indolinyl, 3H-indolyl, chromanyl, 2-azabicyclo [2.2.1]heptanyl, octahydroindolyl, or tetrahydroquinolinyl.

Unless otherwise indicated, the term "hydrogen" or "hydro" refers to the moiety of a hydrogen atom (—H) and not $H_2$.

The term "respiratory disorder" includes chronic obstructive pulmonary disorder (COPD), asthma, allergic rhinitis, bronchospasm, and cystic fibrosis.

Unless otherwise indicated, the term "a compound of the formula" or "a compound of formula" or "compounds of the formula" or "compounds of formula" refers to any compound selected from the genus of compounds as defined by the formula (including, if not otherwise noted, any embodiment thereof such as a pharmaceutically acceptable salt or ester of any such compound, a stereoisomer, a geometric isomer, a tautomer, a solvate, a metabolite, an isotope, a pharmaceutically acceptable salt, or a prodrug).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. Another embodiment provides non-pharmaceutically acceptable salts of a compound of formula I, which can be useful as an intermediate for isolating or purifying a compound of formula I. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". In certain embodiments the compound is enriched by at least about 90% by weight with a single diastereomer or enantiomer. In other embodiments the compound is enriched by at least about 95%, 98%, or 99% by weight with a single diastereomer or enantiomer. Enantiomers may be separated from a racemic mixture by a chiral separation method, such as supercritical fluid chromatography (SFC).

The term "chiral center" refers to an atom holding a set of ligands in a spatial arrangement, which is not superimposable on its mirror image. A chirality center may be considered a generalized extension of the concept of the asymmetric carbon atom to central atoms of any element. Each chiral center (*C) is suitably labeled R or S according to a system by which its substituents are each designated a priority according to the Cahn Ingold Prelog priority rules (CIP), based on atomic number. In some embodiments, the stereochemistry of the chiral centers (marked by "*C") represents all possible combinations in terms of relative and absolute chemistry.

Certain compounds of the present invention possess asymmetric carbon atoms (optical centers) or double bonds. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned. Assignment of configuration at chiral centers in separated enantiomers may be tentative, and depicted in Tables 1 to 3 structures for illustrative purposes, while stereochemistry is definitively established, such as from x-ray crystallographic data.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered, including but not limited to, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Compounds

In the various embodiments of the present disclosure, the sulfonylcycloalkyl carboxamide compounds or a pharmaceutically acceptable salt thereof are of the following formula (I):

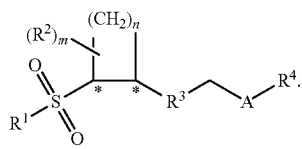

(I)

In any of the various embodiments, n is 2 or 3. In some embodiments, n is 2 thereby providing for a cyclobutane ring. In some embodiments, n is 3 thereby providing for a cyclopentane ring.

$R^1$ is aryl or heteroaryl, each optionally substituted with one or more groups independently selected from halogen, —CN, $C_{1-6}$ alkyl and $C_{1-6}$ haloalkyl. In some embodiments, $R^1$ is aryl substituted with a substituent selected from Br, Cl, F, —CHF$_2$, —CF$_3$, —CHCl$_2$ and —CCl$_3$ at any of the ortho, meta or para positions.

In some embodiments, $R^1$ is:

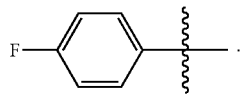

In some alternative embodiments, F may be at a ring position other than the indicated position, and F may replaced with —CHF$_2$ or —CF$_3$.

In any of the various embodiments, m is 0, 1, 2 or 3. In some embodiments, m is 0. In some embodiments, m is 1. In some embodiments, m is 2. In some embodiments, m is 3. Each $R^2$ is independently selected from halogen, —C$_{1-6}$ alkyl, —C$_{1-6}$ haloalkyl, —O—C$_{1-6}$ alkyl, —C$_{3-7}$ cycloalkyl, and —CN. In some embodiments, each $R^2$ is independently selected from —CH$_3$, —CH$_2$CH$_3$, -cyclopropane, —CF$_3$, —CN and F.

$R^3$ is an amide selected from the orientation —NH—C(O)— and —C(O)—NH—.

$R^4$ is a 4, 5, 6 or 7-membered heterocycle, aryl or heteroaryl optionally substituted with one or more groups independently selected from halogen, —C$_{1-6}$ alkyl, —C$_{1-6}$ haloalkyl, —O—C$_{1-6}$ haloalkyl, and —CN.

In some embodiments, $R^4$ is of the formula:

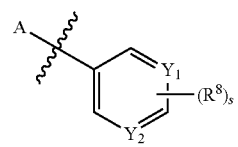

In such embodiments, $Y_1$ and $Y_2$ are independently selected from C and N and s is 0 or 1. $R^8$ is selected from halogen, —O—C$_{1-6}$ haloalkyl, and —C$_{1-6}$ haloalkyl. In some embodiments, $R^4$ is selected from:

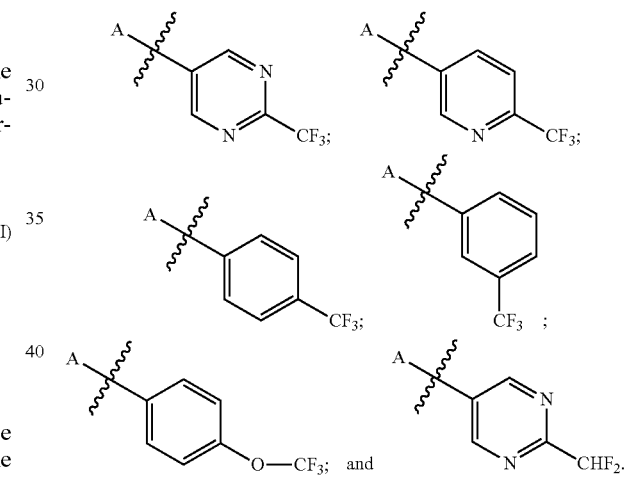

In some embodiments, —CF$_3$, —O—CF$_3$ and —CHF$_2$ may be located at a ring position other than the indicated position.

A is selected from $A^1$, $A^2$ and $A^3$. $A^1$ is unsubstituted or substituted 5-membered heteroaryl comprising one or two nitrogen hetero atoms. $A^2$ is unsubstituted or substituted aryl. $A^3$ is unsubstituted or substituted 6-membered heteroaryl comprising one or two hetero nitrogen atoms.

In some embodiments, A is A1 where A1 is selected from:

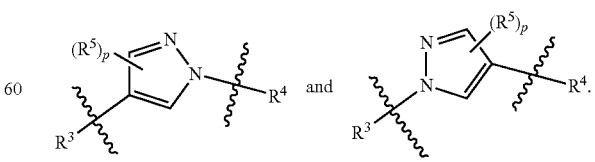

In such embodiments, p is 0 or 1 and $R^5$ is selected from halogen, —O—C$_{1-6}$ alkyl, —C$_{1-6}$ haloalkyl and —C$_{3-7}$ cycloalkyl. In some embodiments, A1 is selected from:

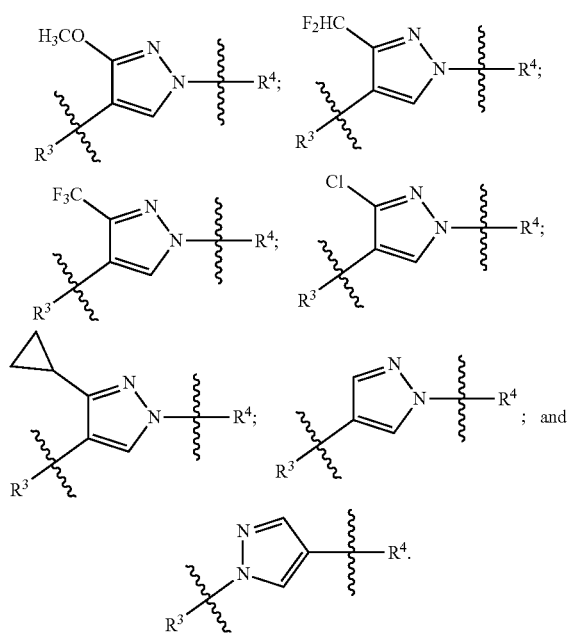

In some embodiments, —O—CH$_3$, —CHF$_2$, —CF$_3$, —Cl, and cyclopropyl may be located at a ring position other than the indicated position.

In some embodiments, A is A2 where A2 is of the formula:

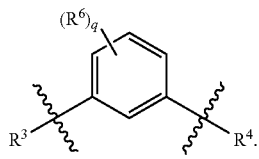

In such embodiments, q is 0, 1 or 2. Each R$^6$ is independently selected from halogen, —O—C$_{1-6}$ alkyl and —C$_{1-6}$ haloalkyl. In some embodiments, A2 is of the formula:

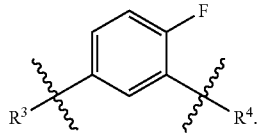

In some alternative embodiments, F may be at a ring position other than the indicated position, and F may replaced with —CHF$_2$ or —CF$_3$.

In some embodiments, A is A3 where A3 is of the formula:

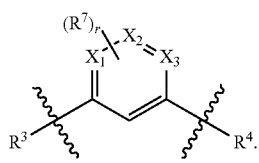

In such embodiments, X$_1$, X$_2$ and X$_3$ are independently selected from C and N wherein: (i) one of X$_1$, X$_2$ and X$_3$ is N and r is 0, 1 or 2; or (ii) X$_1$ and X$_3$ are each N and r is 0 or 1. Each R$^7$ is independently selected from halogen, —O—C$_{1-6}$ alkyl, and —C$_{1-6}$ haloalkyl. In some embodiments, A3 is selected from:

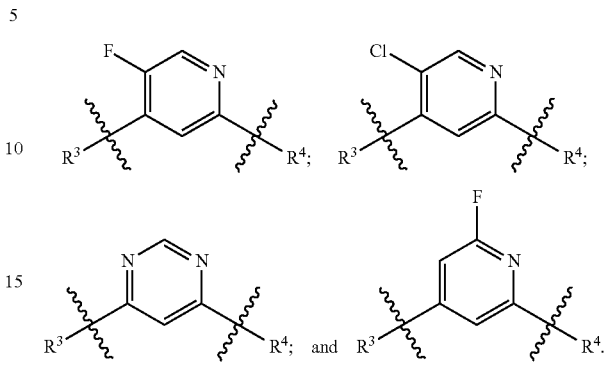

In some alternative embodiments, F and Cl may be at a ring position other than the indicated position, and F and Cl may replaced with —CHF$_2$ or —CF$_3$.

In some embodiments, n is 2 and the sulfonylcycloalkyl carboxamide compound is selected from the following listing of compounds, wherein the ring substitutions may be at a ring position other than the indicated ring position, the indicated substituent may alternatively be replaced by a substituent as described elsewhere herein, and the asterisks denote chiral centers:

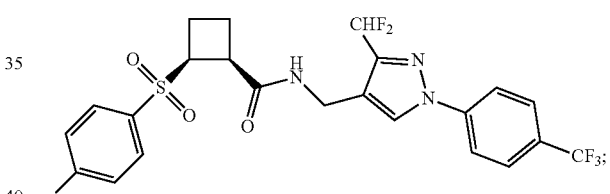

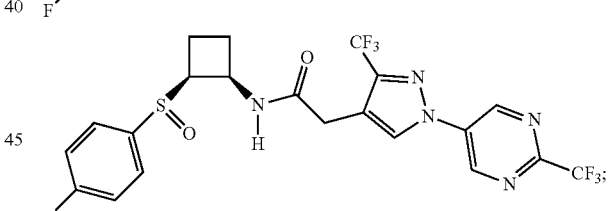

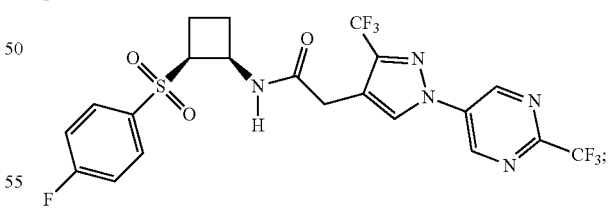

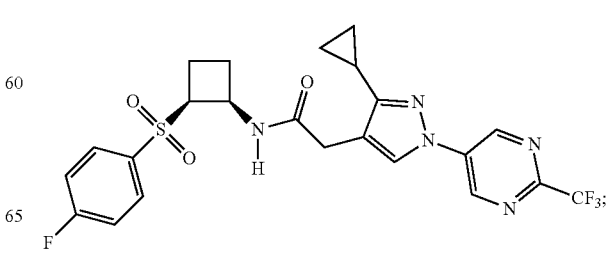

-continued
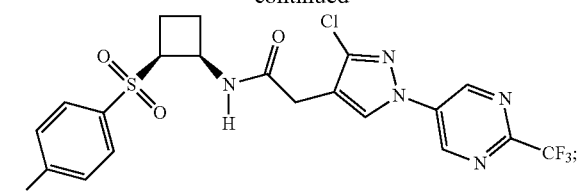
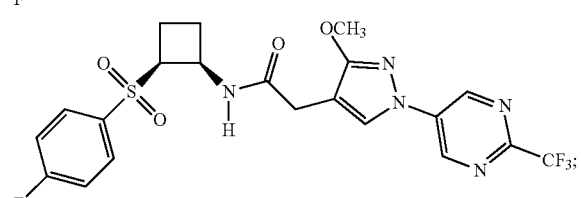
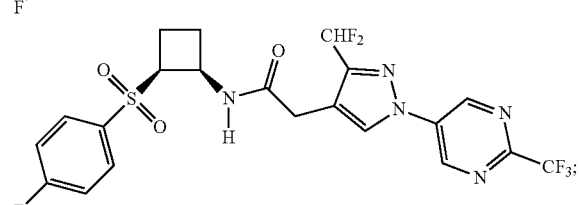
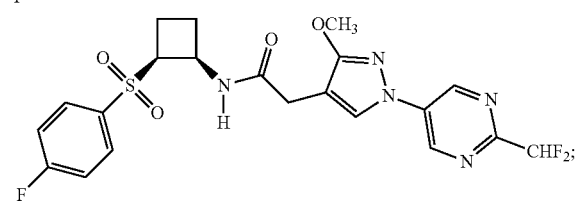
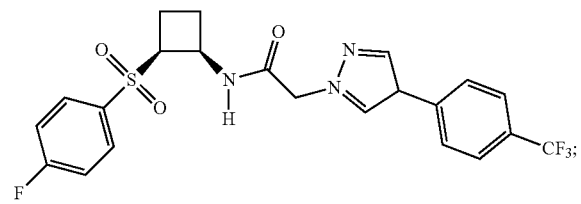
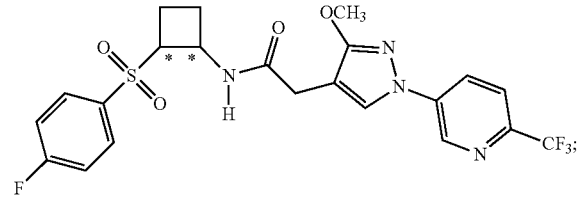
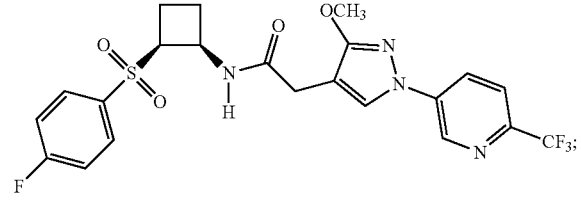
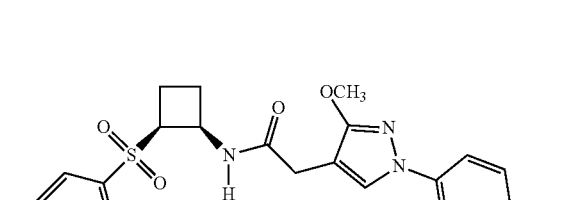
-continued
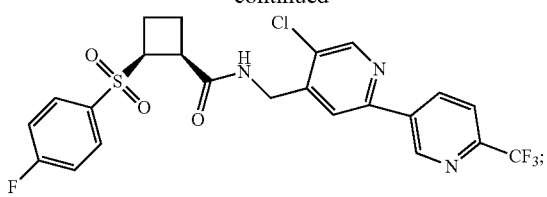
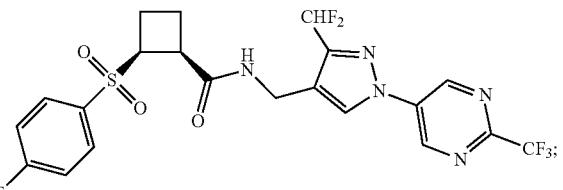
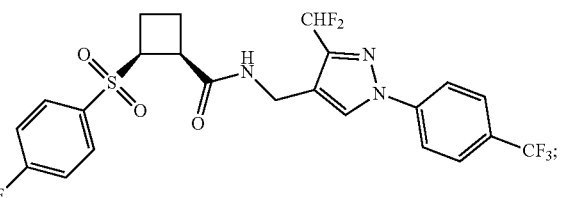
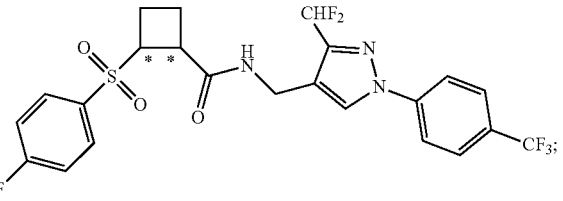
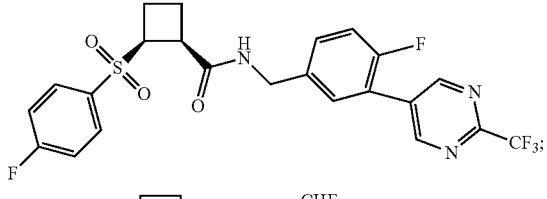
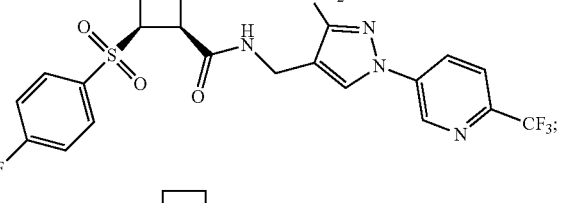
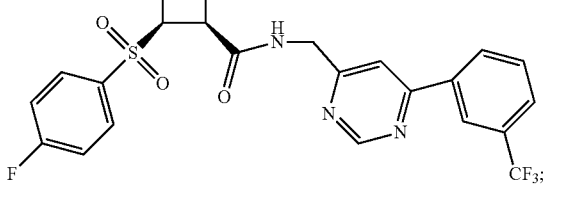
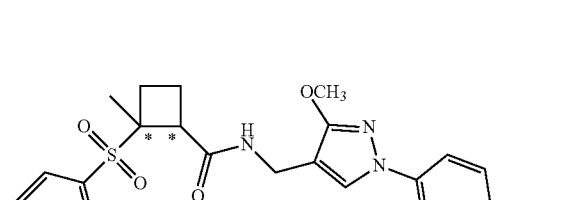

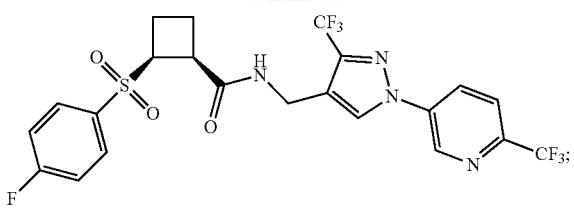

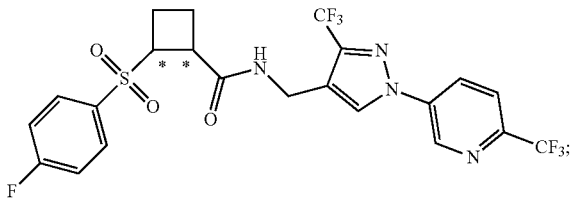

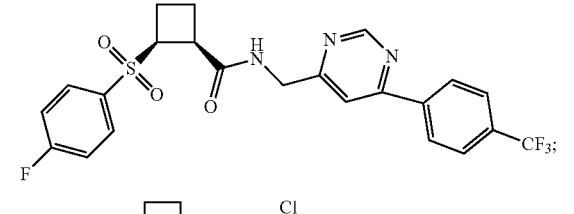

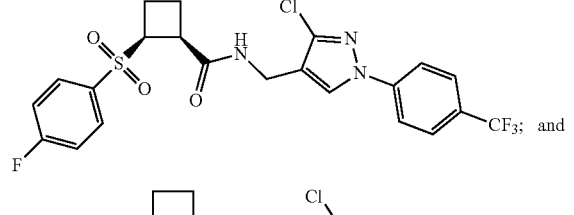

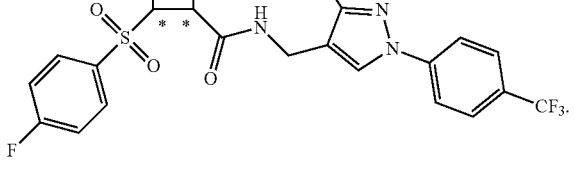

In some embodiments, n is 3 and the sulfonylcycloalkyl carboxamide compounds is selected from the following listing of compounds, wherein the ring substitutions may be at a ring position other than the indicated ring position, the indicated substituent may alternatively be replaced by a substituent as described elsewhere herein, and the asterisks represent chiral centers:

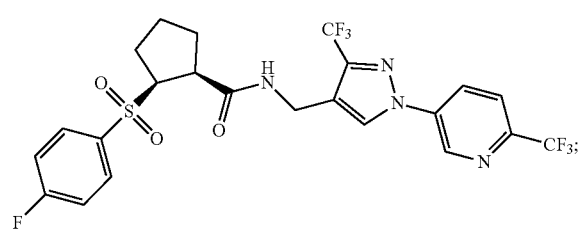 [SMILES: O=C(NCc1cn(-c2ccc(C(F)(F)F)cc2)nc1Cl)[C@@H]1CCC[C@@H]1S(=O)(=O)c1ccc(F)cc1]

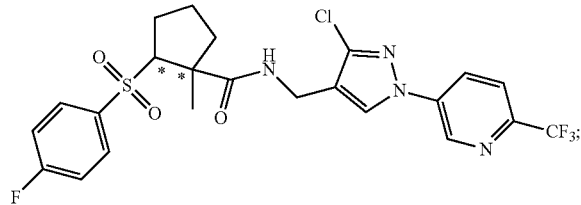

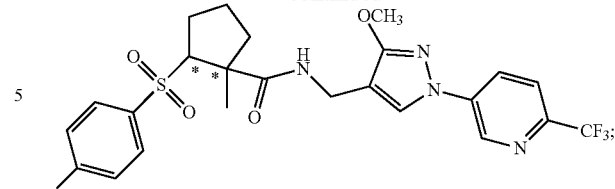

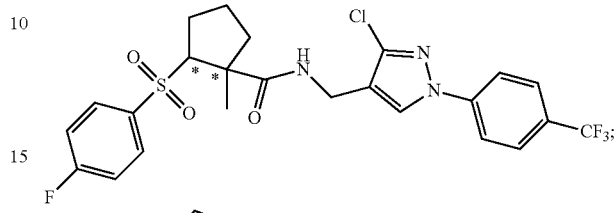

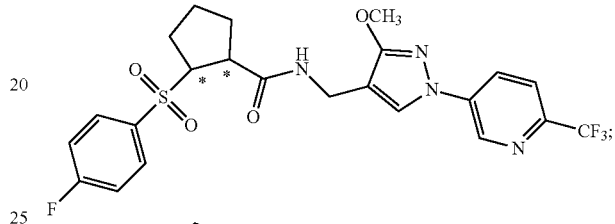

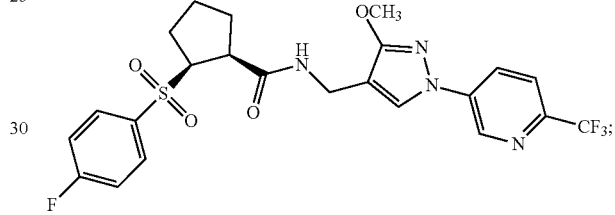

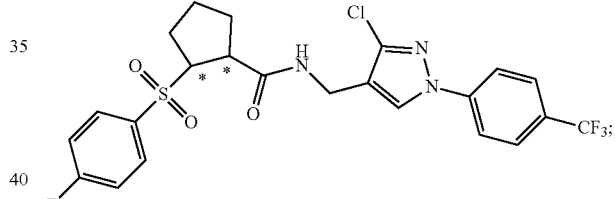

and

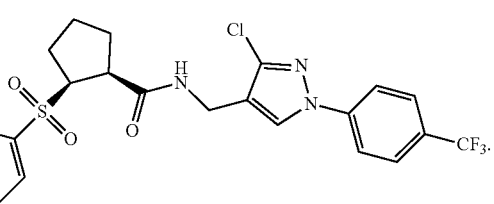

In another embodiment of the invention, the compounds of formula I are isotopically-labeled by having one or more atoms therein replaced by an atom having a different atomic mass or mass number. Such isotopically-labeled (i.e., radio-labelled) compounds of formula I are considered to be within the scope of this invention. Examples of isotopes that can be incorporated into the compounds of formula I include isotopes of hydrogen, carbon, nitrogen, oxygen, phosphorous, sulfur, fluorine, chlorine, and iodine, such as, but not limited to, $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These isotopically-labeled compounds would be useful to help determine or measure the effectiveness of the compounds, by characterizing, for example, the site or mode of action on the ion channels, or binding affinity to pharmacologically important site of action on the ion channels, particularly TRPA1. Certain isotopically-labeled compounds of formula I, for example, those incorporating a radioactive isotope, are useful in drug and/or substrate tissue distribution studies. The radioactive isotopes tritium, i.e. $^3$H, and carbon-14, i.e., $^{14}$C, are particularly useful for this purpose in view of their ease of incorporation and ready means of detection. For example, a compound of formula I can be enriched with 1, 2, 5, 10, 25, 50, 75, 90, 95, or 99 percent of a given isotope.

Substitution with heavier isotopes such as deuterium, i.e. $^2$H, may afford certain therapeutic advantages resulting from greater metabolic stability, for example, increased in vivo half-life or reduced dosage requirements.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula I can generally be prepared by conventional techniques known to those skilled in the art or by processes analogous to those described in the Examples as set out below using an appropriate isotopically-labeled reagent in place of the non-labeled reagent previously employed.

In another embodiment, the invention provides for a pharmaceutical composition, comprising a therapeutically effective amount of a compound according to formula I or a pharmaceutically acceptable salt thereof and a pharmaceutically acceptable carrier.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, $—P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}$C or $^3$H) isotope of a compound of the invention, administering it parenterally in a detectable dose (e. g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Pharmaceutical Compositions and Administration

In addition to one or more of the compounds provided above (including stereoisomers, geometric isomers, tautomers, solvates, metabolites, isotopes, pharmaceutically acceptable salts, or prodrugs thereof), the invention also provides for compositions and medicaments comprising a compound of formula I or and embodiment thereof and at least one pharmaceutically acceptable carrier. The compositions of the invention can be used to selectively inhibit TRPA1 in patients (e.g., humans).

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In one embodiment, the invention provides for pharmaceutical compositions or medicaments comprising a compound of formula I (or embodiments thereof including stereoisomers, geometric isomers, tautomers, solvates, metabolites, isotopes, pharmaceutically acceptable salts, and prodrugs thereof) and a pharmaceutically acceptable carrier, diluent or excipient. In another embodiment, the invention provides for preparing compositions (or medicaments) comprising compounds of the invention. In another embodiment, the invention provides for administering compounds of formula I or its embodiments and compositions comprising compounds of formula I or an embodiment thereof to a patient (e.g., a human patient) in need thereof.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The effective amount of the compound to be administered will be governed by such considerations, and is the minimum amount necessary to inhibit TRPA1 activity as required to prevent or treat the undesired disease or disorder, such as for example, pain. For example, such amount may be below the amount that is toxic to normal cells, or the mammal as a whole.

In one example, the therapeutically effective amount of the compound of the invention administered parenterally per dose will be in the range of about 0.01-100 mg/kg, alternatively about e.g., 0.1 to 20 mg/kg of patient body weight per day, with the typical initial range of compound used being 0.3 to 15 mg/kg/day. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

The compounds of the invention may be administered by any suitable means, for instance, oral (e.g., buccal), topical, sublingual, rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, intracerebral, intraocular, intralesional or subcutaneous administration.

The compositions comprising compounds of formula I (or embodiments thereof including stereoisomers, geometric isomers, tautomers, solvates, metabolites, isotopes, pharmaceutically acceptable salts, and prodrugs thereof) are normally formulated in accordance with standard pharmaceutical practice as a pharmaceutical composition. A typical formulation is prepared by mixing a compound of the present invention and a diluent, carrier or excipient. Suitable diluents, carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament). Suitable carriers, diluents and excipients are well known to those skilled in the art and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., a compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy:

Remington the Science and Practice of Pharmacy (2005) 21$^{st}$ Edition, Lippincott Williams & Wilkins, Philadelphia, Pa. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

Formulations of a compound of the invention (e.g., compound of formula I or an embodiment thereof) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of formula I or an embodiment thereof) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

An example of a suitable oral administration form is a tablet containing about 0.1 mg, about 1 mg, about 5 mg, about 10 mg, about 25 mg, about 30 mg, about 50 mg, about 80 mg, about 100 mg, about 150 mg, about 250 mg, about 300 mg and about 500 mg of the compounds (or an embodiment thereof) of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base. If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

For topical formulations, it is desired to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention (or an embodiment thereof) per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use.

Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

When the binding target is located in the brain, certain embodiments of the invention provide for a compound of formula I (or an embodiment thereof) to traverse the blood-brain barrier. Certain neurodegenerative diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods.

Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™ Guildford. Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I (or an embodiment thereof) in liposomes that are coupled to antibody binding fragments that bind to receptors on the vascular endothelium of the blood-brain barrier (see, e.g., U.S. Patent Application Publication No. 2002/0025313), and coating a compound of formula I (or an embodiment thereof) in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating a compound of formula I (or an embodiment thereof) with a transferrin and modulating activity of the one or more transferrin receptors (see, e.g., U.S. Patent Application Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

Representative compounds of the invention have been shown to modulate TRPA1 activity. Accordingly, the compounds of the invention (or an embodiment thereof) are useful as a medical therapy for treating diseases and conditions mediated by TRPA1 activity. Such diseases and conditions include but are not limited to: pain (acute, chronic, inflammatory, or neuropathic pain); itch or various inflammatory disorders; inner ear disorders; fever or other disorders of thermoregulation; tracheobronchial or diaphragmatic dysfunction; gastrointestinal or urinary tract disorders; respiratory disorders such as chronic obstructive pulmonary disease; incontinence; and disorders associated with reduced blood flow to the CNS or CNS hypoxia.

In a specific embodiment, compounds of the invention (or an embodiment thereof) can be administered as a medical therapy to treat pain, including but not limited to neuropathic and inflammatory pain, among others. Certain types of pain may be considered a disease or disorder, while other types may be considered symptoms of various diseases or disorders, and pain may include various etiologies. Exemplary types of pain treatable with a TRPA1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports* 2004, 8, 393), sinusitis, oral mucositis, toothache, dental trauma, dental extractions, dental infections, burn (Bolcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, Gl tract disorders, cystitis, interstitial cystitis, cholecystitis, urinary tract infection, urethral colic, renal colic, pharyngitis, cold sores, stomatitis, external otitis, otitis media (Chan et al., *Lancet,* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J Pharmacal Exp Ther.,* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barre syndrome, Raynaud's syndrome, coronary artery spasm (Printzmetal's or variant angina), visceral hyperalgesia (Pomonis, J. D. et al. *J. Pharmacal. Exp. Ther.* 2003, 306, 387; Walker, K. M. et al., *J. Pharmacal. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25, 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another specific embodiment, compounds of the invention (or an embodiment thereof) can be administered as a medical therapy to treat itch, which may arise from various sources, such as dermatological or inflammatory disorders.

In another specific embodiment, compounds of the invention (or an embodiment thereof) can be administered as a medical therapy to treat inflammatory disorders, including disorders selected from the group consisting of: renal or hepatobiliary disorders, immunological disorders, medication reactions and unknown/idiopathic conditions. Inflammatory disorders treatable with an inventive agent include, for example, inflammatory bowel disease (1BO), Crohn's disease, and ulcerative colitis (Geppetti, P. et al., *Br. J. Pharmacal.* 2004, 141, 1313-20; Yiangou, Y. et al., *Lancet* 2001, 357, 1338-39; Kimball, E. S. et al., *Neurogastroenterol. Motif,* 2004, 16, 811), osteoarthritis (Szabo, A. et al., *J. Pharmacal. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another specific embodiment, compounds of the invention (or an embodiment thereof) can be administered as a medical therapy to treat inner ear disorders. Such disorders include, for example, hyperacusis, tinnitus, vestibular hypersensitivity, and episodic vertigo.

For example, compounds of the invention (or an embodiment thereof) can be administered as a medical therapy to treat tracheobronchial and diaphragmatic dysfunctions including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacal.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In another specific embodiment, compounds of the invention (or an embodiment thereof) can be administered as a medical therapy to treat gastrointestinal and urinary tract disorders such as, bladder overactivity, inflammatory hyperalgesia, visceral hyperreflexia of the urinary bladder, hemorrhagic cystitis (Dinis, P. et al., *J Neurosci.,* 2004, 24, 11253-11263), interstitial cystitis (Sculptoreanu, A. et al., *Neurosci Lett.,* 2005, 381, 42-46), inflammatory prostate disease, prostatitis (Sanchez, M. et al., *Eur J Pharmacal.,* 2005, 515, 20-27), nausea, vomiting, intestinal cramping, intestinal bloating, bladder spasms, urinary urgency, defecation urgency and urge incontinence.

In another specific embodiment, compounds of the invention (or an embodiment thereof) can be administered as a medical therapy to treat disorders associated with reduced blood flow to the CNS or CNS hypoxia. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, compounds of the invention (or an embodiment thereof) can be administered as a medical therapy to treat other diseases, disorders, or conditions mediated through TRPA1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In one specific embodiment, compounds of the invention (or an embodiment thereof) are administered as a medical therapy to treat pain (including but not limited to acute, chronic, neuropathic and inflammatory pain), arthritis, itch, cough, asthma, or inflammatory bowel disease.

In another embodiment, the invention provides for a method for treating neuropathic pain or inflammatory pain, comprising the step of administering a therapeutically effective amount of a compound according to formula I (or an embodiment thereof) as described elsewhere herein to a subject in need thereof.

In another embodiment, the invention provides for a compound of formula I as described elsewhere herein or (or an embodiment thereof) for use in modulating TRPA1 activity. In some embodiments, the invention provides for a pharmaceutically acceptable salt of compound of formula I for use in modulating TRPA1 activity.

In another embodiment, the invention provides for a compound of formula I as described elsewhere herein, or an embodiment thereof such as a pharmaceutically acceptable salt thereof, for use in medical therapy.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula I (or an embodiment thereof) as described elsewhere herein to a subject in need thereof.

In another embodiment, the invention provides for a compound of formula I as described elsewhere herein or an embodiment thereof such as a pharmaceutically acceptable salt thereof for the treatment or prophylaxis of a respiratory disorder.

In another embodiment, the invention provides for the use of a compound of formula I as described elsewhere herein or an embodiment thereof such as a pharmaceutically acceptable salt thereof for the preparation of a medicament for the treatment or prophylaxis of a respiratory disorder.

In another embodiment, the invention provides for a method for treating a respiratory disorder in a mammal (e.g., a human) comprising administering a compound of formula I as described elsewhere herein or an embodiment thereof such as a pharmaceutically acceptable salt thereof to the mammal.

In another embodiment, the invention provides for a method for modulating TRPA1 activity, comprising contacting TRPA1 with a compound of formula I as described elsewhere herein or an embodiment thereof such as a salt thereof.

In another embodiment, the invention provides for a compound of formula I as described elsewhere herein or an embodiment thereof such as a pharmaceutically acceptable salt thereof for the treatment or prophylaxis of a disease or condition mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, wherein the disease or condition is pain (including but not limited to acute, chronic, neuropathic and inflammatory pain), arthritis, itch, cough, asthma, inflammatory bowel disease, or an inner ear disorder.

In another embodiment, the invention provides for the use of a compound of formula I as described elsewhere herein or an embodiment thereof such as a pharmaceutically acceptable salt thereof for the preparation of a medicament for the treatment or prophylaxis of a disease or condition that is mediated by TRPA1 activity. Within aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within aspects of this embodiment, the disease or condition is pain (including but not limited to acute, chronic, neuropathic and inflammatory pain), arthritis, itch, cough, asthma, inflammatory bowel disease, or an inner ear disorder.

In another embodiment, the invention provides for a method for treating a disease or condition mediated by TRPA1 activity in a mammal (e.g., a human), comprising administering a compound of formula I as described elsewhere herein or an embodiment thereof such as a pharmaceutically acceptable salt thereof to the mammal. Within certain aspects of this embodiment, the disease or condition is pain (including but not limited to acute, chronic, neuropathic and inflammatory pain), itch, an inflammatory disorder, an inner ear disorder, fever or another disorder of thermoregulation, tracheobronchial or diaphragmatic dysfunction, a gastrointestinal or urinary tract disorder, chronic obstructive pulmonary disease, incontinence, or a disorder associated with reduced blood flow to the CNS or CNS hypoxia. Within certain aspects of this embodiment, the disease or condition is pain (including but not limited to acute, chronic, neuropathic and inflammatory pain), arthritis, itch, cough, asthma, inflammatory bowel disease, or an inner ear disorder.

In one aspect, compounds of the invention demonstrate higher potency as compared to other analogues. Such representative compounds, commensurate in scope of the present invention, are shown below in Table 1 wherein "$IC_{50}$" denotes hTRPA1 CHO Ca2+AUC EVO ($IC_{50}$) in micromolar units, and wherein the asterisks denote chiral centers:

TABLE 1

| Formula | Name | IC$_{50}$ |
|---|---|---|
| | N-((1R,2S)-2-((4-fluorophenyl)sulfonyl)cyclobutyl)-2-(3-methoxy-1-(4-(trifluoromethyl)phenyl)-1H-pyrazol-4-yl)acetamide | 0.0052 |
| | N-((1R,2S)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide | 0.00788 |
| | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 1) | 0.00879 |
| | N-((1R,2S)-2-((4-fluorophenyl)sulfonyl)cyclobutyl)-2-(3-methoxy-1-(6-(trifluoromethyl)pyridin-3-yl)-1H-pyrazol-4-yl)acetamide | 0.0185 |
| | (1S,2S)-N-((3-chloro-1-(4-(trifluoromethyl)phenyl)-1H-pyrazol-4-yl)methyl)-2-(4-fluorophenylsulfonyl)cyclobutanecarboxamide | 0.0194 |
| | (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide | 0.0218 |

TABLE 1-continued

| Formula | Name | IC$_{50}$ |
|---|---|---|
| | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 2) | 0.0239 |
| | (1S,2S)-N-((3-(difluoromethyl)-1-(4-(trifluoromethyl)phenyl)-1H-pyrazol-4-yl)methyl)-2-(4-fluorophenylsulfonyl)cyclobutanecarboxamide | 0.0242 |
| | 2-(4-fluorophenylsulfonyl)-N-((3-methoxy-1-(6-(trifluoromethyl)pyridin-3-yl)-1H-pyrazol-4-yl)methyl)-1-methylcyclopentanecarboxamide (Enantiomer 1) | 0.0331 |
| | (1S,2S)-N-((3-(difluoromethyl)-1-(4-(trifluoromethyl)phenyl)-1H-pyrazol-4-yl)methyl)-2-(4-fluorophenylsulfonyl)cyclobutanecarboxamide | 0.0346 |
| | 2-(3-(difluoromethyl)-1-(2-(trifluoromethyl)pyrimidin-5-yl)-1H-pyrazol-4-yl)-N-((1R,2S)-2-(4-fluorophenylsulfonyl)cyclobutyl)acetamide | 0.0352 |
| | 2-(4-fluorophenylsulfonyl)-N-((3-methoxy-1-(4-(trifluoromethyl)phenyl)-1H-pyrazol-4-yl)methyl)-2-methylcyclobutanecarboxamide (Enantiomer 2) | 0.038 |

TABLE 1-continued

| Formula | Name | IC$_{50}$ |
|---|---|---|
| | (1S,2S)-N-((3-chloro-1-(4-(trifluoromethyl)phenyl)-1H-pyrazol-4-yl)methyl)-2-(4-fluorophenylsulfonyl)cyclopentanecarboxamide | 0.0389 |
| | N-((3-chloro-1-(6-(trifluoromethyl)pyridin-3-yl)-1H-pyrazol-4-yl)methyl)-2-(4-fluorophenylsulfonyl)-1-methylcyclopentanecarboxamide (Enantiomer 1) | 0.0392 |
| | 2-(3-chloro-1-(2-(trifluoromethyl)pyrimidin-5-yl)-1H-pyrazol-4-yl)-N-((1R,2S)-2-(4-fluorophenylsulfonyl)cyclobutyl)acetamide | 0.0403 |
| | (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide | 0.0404 |
| | (1S,2S)-2-(4-fluorophenylsulfonyl)-N-((3-(trifluoromethyl)-1-(6-(trifluoromethyl)pyridin-3-yl)-1H-pyrazol-4-yl)methyl)cyclobutanecarboxamide | 0.0415 |

TABLE 1-continued

| Formula | Name | IC$_{50}$ |
|---|---|---|
|  | N-((3-chloro-1-(4-(trifluoromethyl)phenyl)-1H-pyrazol-4-yl)methyl)-2-(4-fluorophenylsulfonyl)cyclopentanecarboxamide (Enantiomer 2) | 0.0455 |
|  | 2-(3-cyclopropyl-1-(2-(trifluoromethyl)pyrimidin-5-yl)-1H-pyrazol-4-yl)-N-((1R,2S)-2-(4-fluorophenylsulfonyl)cyclobutyl)acetamide | 0.0469 |
|  | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 3) | 0.0471 |

Combination Therapy

The compounds of the invention (or an embodiment thereof) may be usefully combined with one or more other compounds of the invention or one or more other therapeutic agent or as any combination thereof, in the treatment of ion channel-mediated diseases and conditions. For example, a compound of the invention may be administered simultaneously, sequentially or separately in combination with one or more co-therapeutic agents.

In some embodiments, the co-therapeutic agent is an opiate analgesic. Examples of opiate analgesics include morphine, heroin, cocaine, oxymorphone, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine, pentazocine, and combinations thereof.

In some embodiments, the co-therapeutic agent is a non-opiate analgesic such as acetomeniphen and/or salicylate (e.g., aspirin).

In some embodiments, the co-therapeutic agent is a non-steroidal antiinflammatory drug (NSAIDs). Examples of NSAIDs include ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin, zomepirac, and combinations thereof.

In some embodiments, the co-therapeutic agent is an anticonvulsant. Examples of anticonvulsants include carbamazepine, oxcarbazepine, lamotrigine, valproate, topiramate, gabapentin, pregabalin, and combinations thereof.

In some embodiments, the co-therapeutic agent is an antidepressant. Examples of antidepresents include amitriptyline, clomipramine, despramine, imipramine, nortriptyline, and combinations thereof.

In some embodiments, the co-therapeutic agent is a COX-2 selective inhibitor. Examples of COX-2 inhibitors include celecoxib, rofecoxib, parecoxib, valdecoxib, deracoxib, etoricoxib, lumiracoxib, and combinations thereof.

In some embodiments, the co-therapeutic agent is an alpha-adrenergic. Examples of alpha-adrenergics include doxazosin, tamsulosin, clonidine, guanfacine, dexmetatomidine, modafinil, 4-amino-6,7-dimethoxy-2-(5-methane sulfonamido-1,2,3,4-tetrahydroisoquinol-2-yl)-5-(2-pyridyl) quinazoline, and combinations thereof.

In some embodiments, the co-therapeutic agent is a barbiturate sedative. Examples of barbiturate sedatives include amobarbital, aprobarbital, butabarbital, butabital, mephobarbital, metharbital, methohexital, pentobarbital, phenobarbital, secobarbital, talbutal, theamylal, thiopental, and combinations thereof.

In some embodiments, the co-therapeutic agent is a tachykinin (NK) antagonist. Examples of tachykinin antagonists include NK-3, NK-2 or NK-1 antagonist such as (7R, 9R)-7-[3,5-bis(trifluoromethyl)benzyl)]-8,9,10,11-tetrahydro-9-methyl-5-(4-methylphenyl)-7H-[1,4]diazocino[2, 1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant, 3-[[2-methoxy5-(trifluoromethoxy)phenyl]-methylamino]-2-phenylpiperidine (2S,3S), and combinations thereof.

In some embodiments, the co-therapeutic agent is a coal-tar analgesic such as paracetamol.

In some embodiments, the co-therapeutic agent is a serotonin reuptake inhibitor (SRI). Examples of SRIs include paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone, fluoxetine, and combinations thereof.

In some embodiments, the co-therapeutic agent is a noradrenaline (norepinephrine) reuptake inhibitors. Examples of noradrenaline reuptake inhibitors include maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, venlafaxine duloxetine neuroleptics sedative/anxiolytics, and combinations thereof.

In some embodiments, the co-therapeutic agent is a dual serotonin-noradrenaline reuptake inhibitors. Examples of such dual inhibitors include venlafaxine metabolite O-desmethylvenlafaxine, clomipramine, clomipramine metabolite desmethylclomipramine, duloxetine, milnacipran, imipramine, and combinations thereof.

In some embodiments, the co-therapeutic agent is an acetylcholinesterase inhibitor such as donepezil.

In some embodiments, the co-therapeutic agent is an 5-HT3 antagonist such as ondansetron.

In some embodiments, the co-therapeutic agent is a metabotropic glutamate receptor (mGluR) antagonist.

In some embodiments, the co-therapeutic agent is a local anaesthetic. Examples of local anaesthetics include mexiletine and lidocaine.

In some embodiments, the co-therapeutic agent is a corticosteroid such as dexamethasone.

In some embodiments, the co-therapeutic agent is an antiarrhythimic. Examples of antiarrhythimics include mexiletine and phenytoin.

In some embodiments, the co-therapeutic agent is a muscarinic antagonist. Examples of muscarinic antagonists include tolterodine, propiverine, tropsium t chloride, darifenacin, solifenacin, temiverine, ipratropium, and combinations thereof.

In some embodiments, the co-therapeutic agent is a cannabinoid.

In some embodiments, the co-therapeutic agent is a vanilloid receptor agonist such as resinferatoxin or an antagonist such as capsazepine.

In some embodiments, the co-therapeutic agent is a sedative. Examples of sedatives include glutethimide, meprobamate, methaqualone, dichloralphenazone, and combinations thereof.

In some embodiments, the co-therapeutic agent is an anxiolytic such as benzodiazepine.

In some embodiments, the co-therapeutic agent is an antidepressant such as mirtazapine.

In some embodiments, the co-therapeutic agent is a topical agent. Examples of topical agents include lidocaine, capsacin, resiniferotoxin, and combinations thereof.

In some embodiments, the co-therapeutic agent is a muscle relaxant. Examples of muscle relaxants include benzodiazepines, baclofen, carisoprodol, chlorzoxazone, cyclobenzaprine, methocarbamol, orphrenadine, and combinations thereof.

In some embodiments, the co-therapeutic agent is an anti-histamine or an H1 antagonist.

In some embodiments, the co-therapeutic agent is a NMDA receptor antagonist.

In some embodiments, the co-therapeutic agent is a 5-HT receptor agonist/antagonist.

In some embodiments, the co-therapeutic agent is a PDEV inhibitor.

In some embodiments, the co-therapeutic agent is Tramadol®.

In some embodiments, the co-therapeutic agent is a cholinergic (nicotinc) analgesic.

In some embodiments, the co-therapeutic agent is an alpha-2-delta ligand.

In some embodiments, the co-therapeutic agent is a prostaglandin E2 subtype antagonist.

In some embodiments, the co-therapeutic agent is a leukotriene B4 antagonist.

In some embodiments, the co-therapeutic agent is a 5-lipoxygenase inhibitor.

In some embodiments, the co-therapeutic agent is a 5-HT3 antagonist.

As used herein "combination" refers to any mixture or permutation of one or more compounds of the invention (or an embodiment thereof) and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In another embodiment, provided is an invention as hereinbefore described.

General Preparation of Compounds of Formula I

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention (or an embodiment thereof) can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

EXAMPLES

Although certain exemplary embodiments are depicted and described herein, the compounds of the present invention (or embodiments thereof) can be prepared using appropriate starting materials according to the methods described generally herein and/or by methods available to one of ordinary skill in the art.

Intermediates and final compounds were purified by either flash chromatography, and/or by reverse-phase preparative HPLC (high performance liquid chromatography), and/or by supercritical fluid chromatography. Unless otherwise noted, flash chromatography was carried out using pre-packed silica gel cartridges from either ISCO or SiliCycle on an ISCO CombiFlash® chromatography instrument (from Teledyne Isco, Inc.). Reverse-phase preparative HPLC was performed using a (1) Polaris C-18 5 µM column (50×21 mm), or (2) XBridge Prep C-18 OBD 5 µM column (19×150 mm). Supercritical fluid chromatography was carried out using packed columns by Chiral Technologies, Chiralpak AD, Chiralpak AS, Chiralpak IA, Chiralpak IB, Chiralpak IC, Chiralcel OD, or Chiralcel OJ with column dimensions such as (1) 4.6 cm×5 cm, 3 µM, (2) 4.6 cm×5 cm, 5 µM, or (3) 15 cm×21.2 mm, 5 µM.

Mass spectrometry (MS) was performed using a (1) Sciex 15 mass spectrometer in ES+ mode, or (2) Shimadzu liquid chromatography-masss spectrometry (LCMS) 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) was performed using a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

All reactions involving air-sensitive reagents were performed under an inert atmosphere. Reagents were used as received from commercial suppliers unless otherwise noted.

Example 1: Preparation of (1S,2R)—N-((3-(difluoromethyl)-1-(4-(trifluoromethyl)phenyl)-1H-pyrazol-4-yl)methyl)-2-(4-fluorophenylsulfonyl)cyclobutanecarboxamide The overall Example 1 reaction scheme was as follows:

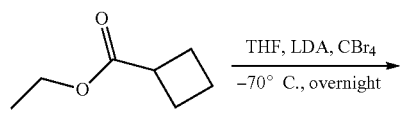

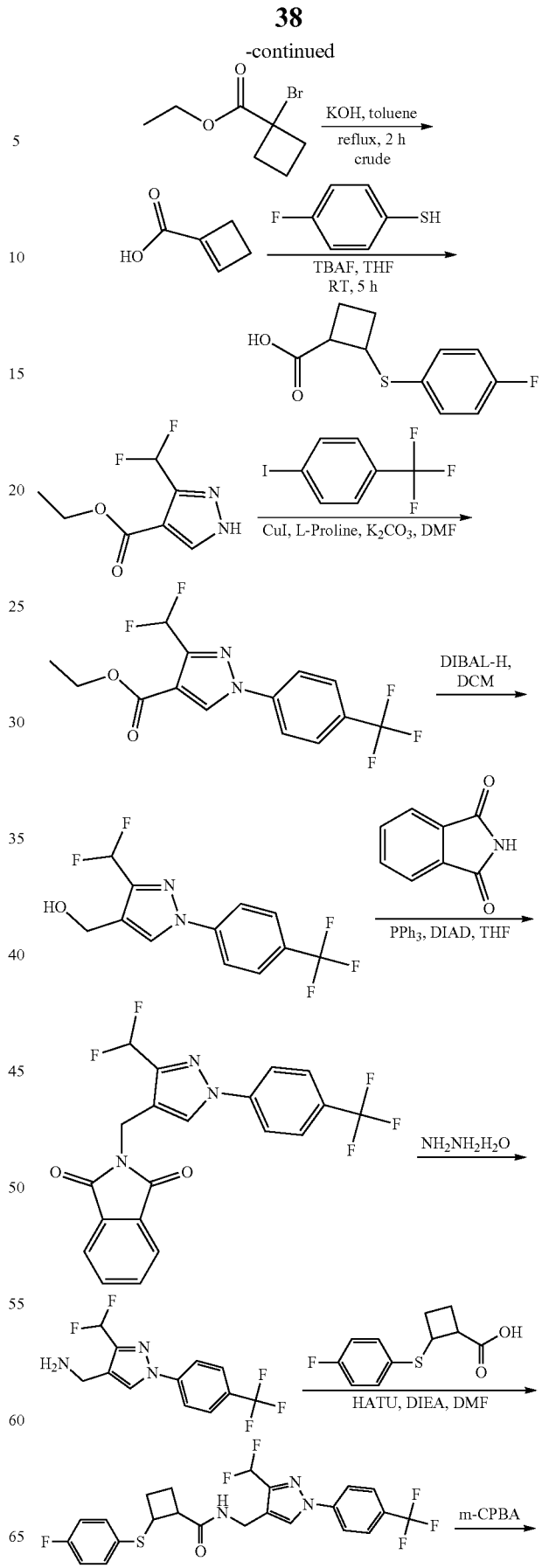

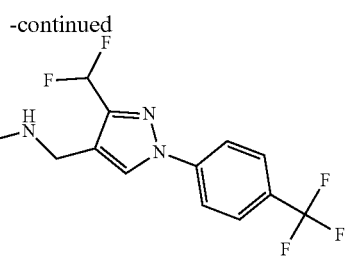

Example 1, Step 1: Preparation of ethyl 1-bromocyclobutanecarboxylate

Step 1 proceeded according to the following scheme:

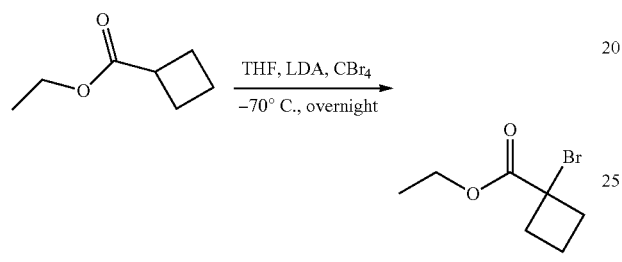

To a 20-L 4-necked round-bottom flask, purged and maintained with an inert atmosphere of nitrogen, was placed LDA solution in THF (1 M) (2295 mL, 1.10 equiv) followed by the addition of a solution of ethyl cyclobutanecarboxylate (500 g, 3.90 mol, 1.00 equiv) in tetrahydrofuran (2.5 L) dropwise with stirring at −78° C. The mixture was stirred at −60° C. for 1 h. To this was added a solution of tetrabromomethane (1250 g, 3.77 mol, 1.00 equiv) in tetrahydrofuran (1250 mL) dropwise with stirring. The resulting solution was stirred overnight from −70° C. to room temperature, quenched by the addition of 600 mL of saturated aqueous NH$_4$Cl at −10° C., and extracted with 3×800 mL of ethyl acetate. The combined organic layers were washed with 2×500 mL of brine, dried over anhydrous sodium sulfate and concentrated under vacuum. The residue was applied onto a silica gel column eluted with ethyl acetate/petroleum ether (1:50) to afford 620 g (77%) of ethyl 1-bromocyclobutane-1-carboxylate as light yellow oil.

Example 1, Step 2: Preparation of cyclobut-1-enecarboxylic acid

Step 2 proceeded according to the following scheme:

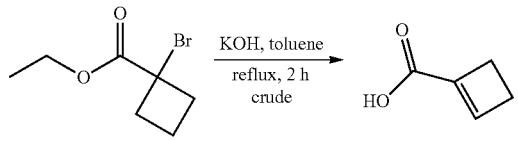

To a 5000-mL 4-necked round-bottom flask, purged and maintained with an inert atmosphere of nitrogen, was placed toluene (2.5 L), potassium hydroxide (240 g, 4.28 mol, 5.50 equiv), and ethyl 1-bromocyclobutane-1-carboxylate (150 g, 724.41 mmol, 1.00 equiv). The resulting solution was heated to reflux for 2 h in an oil bath. This reaction was repeated twice. The reaction mixture was cooled to 25° C. with a water/ice bath, quenched by the addition of 500 mL of water/ice, and extracted with 500 mL of ether. The aqueous layers were combined. The pH value of the solution was adjusted to 2 with aqueous hydrogen chloride (6 N). The resulting solution was extracted with 3×500 mL of ether. The combined organic layers were dried over anhydrous sodium sulfate and concentrated under vacuum. The residue was applied onto a silica gel column eluted with ethyl acetate/petroleum ether (1:50-1:20) to afford 230 g (crude) of cyclobut-1-ene-1-carboxylic acid as a white solid.

Example 1, Step 3: Preparation of 2-((4-fluorophenyl)thio)cyclobutanecarboxylic acid Step 3 proceeded according to the following scheme:

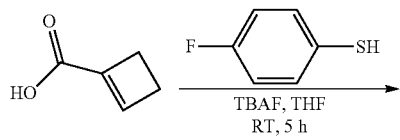

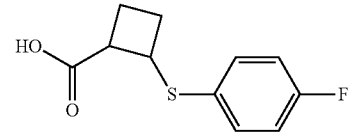

To a 5000-mL 3-necked round-bottom flask, purged and maintained with an inert atmosphere of nitrogen, was placed cyclobut-1-ene-1-carboxylic acid (220 g, 2.24 mol, 1.00 equiv), 4-fluorobenzene-1-thiol (420 g, 3.28 mol, 1.50 equiv) and tetrahydrofuran (2500 mL), followed by the addition of TBAF (900 mL) dropwise with stirring in an ice/water bath. The resulting solution was stirred at room temperature for 5 h, concentrated under vacuum, quenched by the addition of 1200 mL of water/ice, and extracted with 3×1300 mL of ethyl acetate. The organic layers were combined, washed with 2×600 mL of brine, dried over anhydrous sodium sulfate and concentrated under vacuum. The residue was applied onto a silica gel column eluted with ethyl acetate/petroleum ether (1:50-1:20) to afford 246 g (48%) of 2-[(4-fluorophenyl)sulfanyl]cyclobutane-1-carboxylic acid as a white solid. LC-MS: (ES, m/z): [M−H]$^+$= 225; $^1$H-NMR: (300 MHz, CDCl3, ppm): [ ] 1.901~2.181 (m, 1.5H), 2.281~2.440 (m, 2.5H), 3.048~3.078 (m, 0.28H), 3.510~3.544 (m, 0.75H), 3.944~4.142 (m, 1H), 6.931~7.037 (m, 2H), 7.259~7.427 (m, 2H), 10.50 (s, 1H).

Example 1, Step 4: Preparation of ethyl 3-(difluoromethyl)-1-[4-(trifluoromethyl)phenyl]-1H-pyrazole-4-carboxylate Step 4 proceeded according to the following scheme:

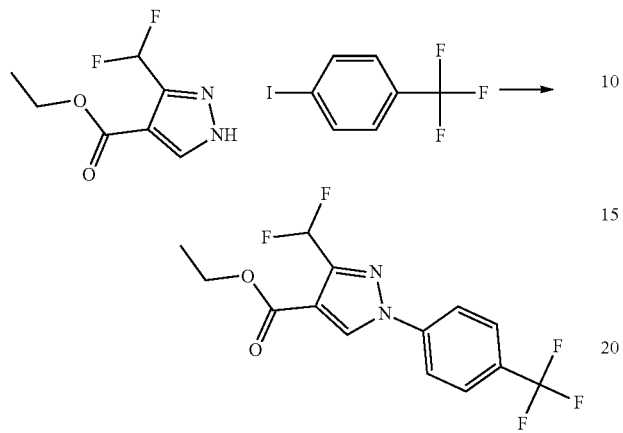

A mixture of ethyl 3-(difluoromethyl)-1H-pyrazole-4-carboxylate (1.23 g, 6.47 mmol, 1.00 equiv), 1-iodo-4-(trifluoromethyl)benzene (2.51 g, 9.21 mmol, 1.42 equiv), CuI (123 mg, 0.65 mmol, 0.10 equiv), L-proline (149 mg, 1.29 mmol, 0.20 equiv), $Cs_2CO_3$ (5.276 g, 16.19 mmol, 2.50 equiv), and N,N-dimethylformamide (50 mL) was stirred for 12 h at 90° C. under nitrogen. The resulting solution was diluted with brine, extracted with ethyl acetate, washed with brine, dried over anhydrous sodium sulfate and concentrated under vacuum. The residue was purified by a silica gel column eluting with ethyl acetate/hexane (1/50) to afford the title compound (1.322 g, 61%) as a light yellow solid. LC-MS (ESI): $[M+H]^+$=335.1.

Example 1, Step 5: Preparation of [3-(difluoromethyl)-1-[4-(trifluoromethyl)phenyl]-1H-pyrazol-4-yl]methanol Step 5 proceeded according to the following scheme:

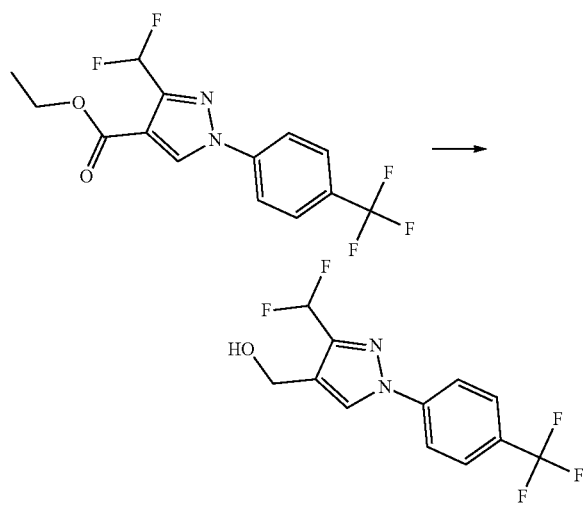

DIBAL (12 mL, 1M in hexane, 3.00 equiv) was added dropwise into a solution of ethyl 3-(difluoromethyl)-1-[4-(trifluoromethyl)phenyl]-1H-pyrazole-4-carboxylate (1.322 g, 3.96 mmol, 1.00 equiv) in dichloromethane (100 mL) at −70° C. under nitrogen. The resulting solution was stirred for 1 h at −70° C. then quenched by the addition of methanol, warmed to room temperature, and concentrated under vacuum. The residue was purified by a silica gel column eluting with ethyl acetate/hexane (1/5) to afford the title compound (1 g, 87%) as a light yellow solid. LC-MS (ESI): $[M+H]^+$=293.1.

Example 1, Step 6: Step 6: Preparation of 2-[[3-(difluoromethyl)-1-[4-(trifluoromethyl)phenyl]-1H-pyrazol-4-yl]methyl]-2,3-dihydro-1H-isoindole-1,3-dione Step 6 proceeded according to the following scheme:

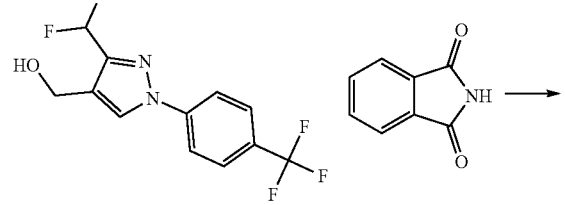

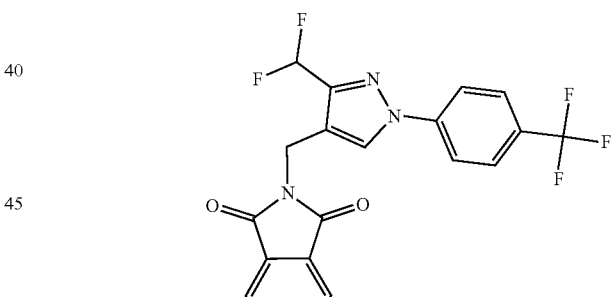

DIAD (1.383 g, 6.84 mmol, 2.00 equiv) was added dropwise into a solution of [3-(difluoromethyl)-1-[4-(trifluoromethyl)phenyl]-1H-pyrazol-4-yl]methanol (1 g, 3.42 mmol, 1.00 equiv), 2,3-dihydro-1H-isoindole-1,3-dione (1 g, 6.80 mmol, 2.00 equiv), and $PPh_3$ (1.79 g, 6.84 mmol, 2.00 equiv) in tetrahydrofuran (200 mL) at 0° C. under nitrogen. The resulting solution was stirred for 3 h at room temperature. The reaction was then quenched by the addition of brine, extracted with ethyl acetate, washed with brine, and dried over anhydrous sodium sulfate. The residue was purified by a silica gel column eluting with ethyl acetate/hexane (1/10) to afford the title compound (2.3 g) as a white solid. LC-MS (ESI): $[M+H]^+$=422.1.

Example 1, Step 7: Preparation of [3-(difluoromethyl)-1-[4-(trifluoromethyl)phenyl]-1H-pyrazol-4-yl]methanamine Step 7 proceeded according to the following scheme:

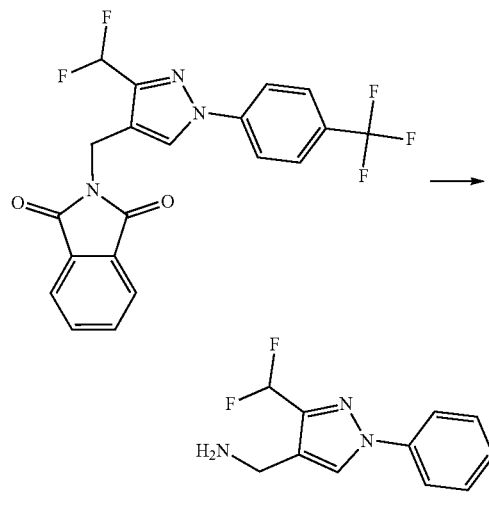

A mixture of 2-[[3-(difluoromethyl)-1-[4-(trifluoromethyl)phenyl]-1H-pyrazol-4-yl]methyl]-2,3-dihydro-1H-isoindole-1,3-dione (2.3 g, 5.46 mmol, 1.00 equiv), methanol (200 mL), and NH2NH2.H2O (2.732 g, 80%) was stirred for 12 h at 60° C. The resulting mixture was concentrated under vacuum and dissolved in 300 mL of ethyl acetate. The solids were filtered out. The filtrate was concentrated under vacuum to afford the title compound (1.58 g) as yellow oil which was used for the next step without any further purification. LC-MS (ESI): [M+H]$^+$=292.1.

Example 1, Step 8: Preparation of N-[[3-(difluoromethyl)-1-[4-(trifluoromethyl)phenyl]-1H-pyrazol-4-yl]methyl]-2-[(4-fluorophenyl)sulfanyl]cyclobutane-1-carboxamide Step 8 proceeded according to the following scheme:

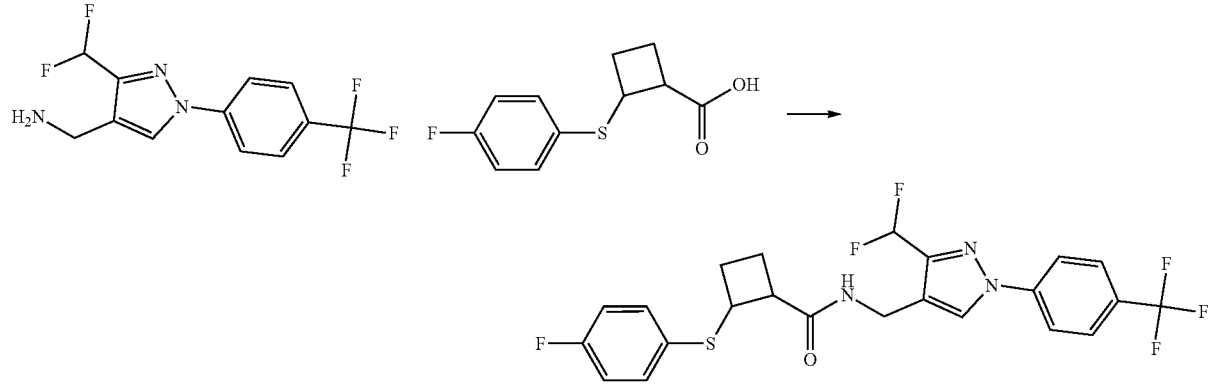

A mixture of 2-[(4-fluorophenyl)sulfanyl]cyclobutane-1-carboxylic acid (730 mg, 3.23 mmol, 1.00 equiv), HATU (833 mg, 2.19 mmol, 0.68 equiv), DIEA (1.473 g, 11.40 mmol, 3.53 equiv), N,N-dimethylformamide (15 mL), and [3-(difluoromethyl)-1-[4-(trifluoromethyl)phenyl]-1H-pyrazol-4-yl]methanamine (940 mg, 3.23 mmol, 1.00 equiv) was stirred for 12 h at room temperature. The resulting solution was diluted with brine, extracted with ethyl acetate, washed with brine, dried over anhydrous sodium sulfate and concentrated under vacuum. The residue was purified by a silica gel column eluting with ethyl acetate/hexane (1/50) to afford the title compound (2.1 g) as a yellow solid. LC-MS (ESI): [M+H]$^+$=500.1.

Example 1, Step 9: Preparation of (1S)—N-[[3-(difluoromethyl)-1-[4-(trifluoromethyl)phenyl]-1H-pyrazol-4-yl]methyl]-2-[(4-fluorobenzene)sulfonyl]cyclobutane-1-carboxamide Step 9 proceeded according to the following scheme:

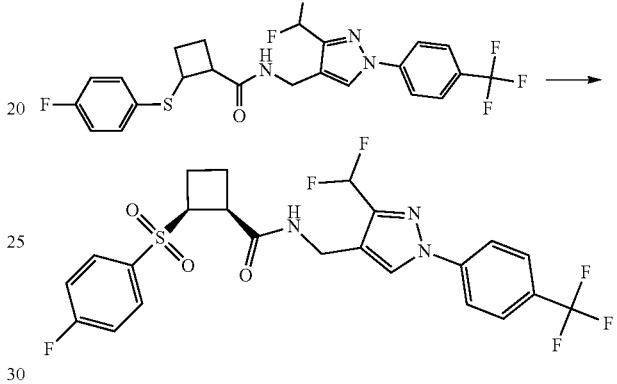

A solution of m-CPBA (1.476 g, 8.55 mmol, 2.14 equiv) in acetate (10 mL) was added dropwise at 0° C. into a solution of N-[[3-(difluoromethyl)-1-[4-(trifluoromethyl)phenyl]-1H-pyrazol-4-yl]methyl]-2-[(4-fluorophenyl)sulfanyl]cyclobutane-1-carboxamide (2 g, 4.00 mmol, 1.00 equiv) in dichloromethane (200 mL). The resulting solution was stirred for 1 h at room temperature. The reaction mixture was diluted with dichloromethane, washed with saturated solution of sodium bicarbonate and brine, dried over anhydrous sodium sulfate and concentrated under vacuum. The residue was purified by a silica gel column eluting with ethyl acetate/petroleum ether (1/1).

The crude product was purified by Chiral-Prep-HPLC to afford (1S,2S)—N-((3-(difluoromethyl)-1-(4-(trifluoromethyl)phenyl)-1H-pyrazol-4-yl)methyl)-2-(4-fluorophenylsulfonyl)cyclobutanecarboxamide (118.8 mg, 6%) as a white solid. tR=3.01 min (CHIRALPAK IC-3, 0.46×5 cm, 3 μm, Hex:EtOH=90:10, 1.0 ml/min). LC-MS (ESI): [M+H]$^+$ =532.1; ¹H NMR (400 MHz, CDCl3) δ 8.12 (s, 1H), 7.9-7.83 (m, 4H), 7.76-7.74 (d, J=8.4 Hz, 2H), 7.24 (t, J=8.4 Hz, 2H), 6.98-6.71 (m, 2H), 4.58 (dd, J=15.0, 6.0 Hz, 1H), 4.43 (dd, J=15.0, 5.6 Hz, 1H), 4.00-3.95 (m, 1H), 3.64-3.57 (m, 1H), 2.45-2.3 (m, 2H), 2.23-2.16 (m, 1H), 2.01-1.97 (m, 1H).

Three more stereoisomers were also isolated from the Chiral-Prep-HPLC resolution.

Isomer 1: (92.5 mg, 4%) as a white solid. tR=1.56 min (Lux 3 u Celloluse-2, 4.6×100 mm, 3 μm, MeOH (0.1% DEA), 10% to 40% in 2.0 min, hold 1.0 min at 40%, 4.0 ml/min). LC-MS (ESI): [M+H]⁺=532.1; ¹H NMR (400 MHz, CDCl3) δ 8.42 (s, 1H), 7.91-7.84 (m, 4H), 7.70 (d, J=8.4 Hz, 2H), 7.25 (d, J=8.4 Hz, 2H), 6.97-6.70 (t, J=54.4 Hz, 1H), 6.60 (s, 1H), 4.73 (dd, J=16, 6.8 Hz, 1H), 4.55 (dd, J₁=15.6, 5.2 Hz, 1H), 4.11-4.05 (m, 1H), 3.61-3.55 (m, 1H), 2.74-2.51 (m, 2H), 2.2-2.1. (m, 2H).

Isomer 2: (136.2 mg, 6%) as a white solid. tR=1.75 min (Lux 3 u Celloluse-2, 4.6×100 mm, 3 μm, MeOH (0.1% DEA), 10% to 40% in 2.0 min, hold 1.0 min at 40%, 4.0 ml/min). LC-MS (ESI): [M+H]⁺=532.1; ¹H NMR (400 MHz, CDCl3) δ 8.42 (s, 1H), 7.91-7.84 (m, 4H), 7.70 (d, J=8.4 Hz, 2H), 7.25 (d, J=6.8 Hz, 2H), 6.97-6.7 (t, J=54 Hz, 1H), 6.59 (t, J=5.6 Hz, 1H), 4.74 (dd, J=15.6, 6.4 Hz, 1H), 4.55 (dd, J₁=15.6, 5.2 Hz, 1H), 4.11-4.05 (m, 1H), 3.59-3.55 (m, 1H), 2.73-2.52 (m, 2H), 2.19-2.12 (m, 2H).

Isomer 3: (95.1 mg, 4%) as a white solid. tR=2.47 min (CHIRALPAK IC-3, 0.46×5 cm, 3 μm, Hex:EtOH=90:10, 1.0 ml/min). LC-MS (ESI): [M+H]⁺=532.1; ¹H NMR (400 MHz, CDCl3) δ 8.12 (s, 1H), 7.90-7.83 (m, 4H), 7.75 (d, J=8.4 Hz, 2H), 7.24 (t, J=8.4 Hz, 2H), 6.98-6.71 (m, 2H), 4.58 (dd, J=15.0, 6.0 Hz, 1H), 4.43 (dd, J=15.0, 5.6 Hz, 1H), 4.00-3.94 (m, 1H), 3.64-3.57 (m, 1H), 2.47-2.3 (m, 2H), 2.23-2.16 (m, 1H), 2.04-1.97 (m, 1H).

Example 2: N-((1R, 2S)-2-(4-fluorophenylsulfinyl)cyclobutyl)-2-(3-(trifluoromethyl)-1-(2-(trifluoromethyl)pyrimidin-5-yl)-1H-pyrazol-4-yl)acetamide The overall Example 2 reaction scheme was as follows:

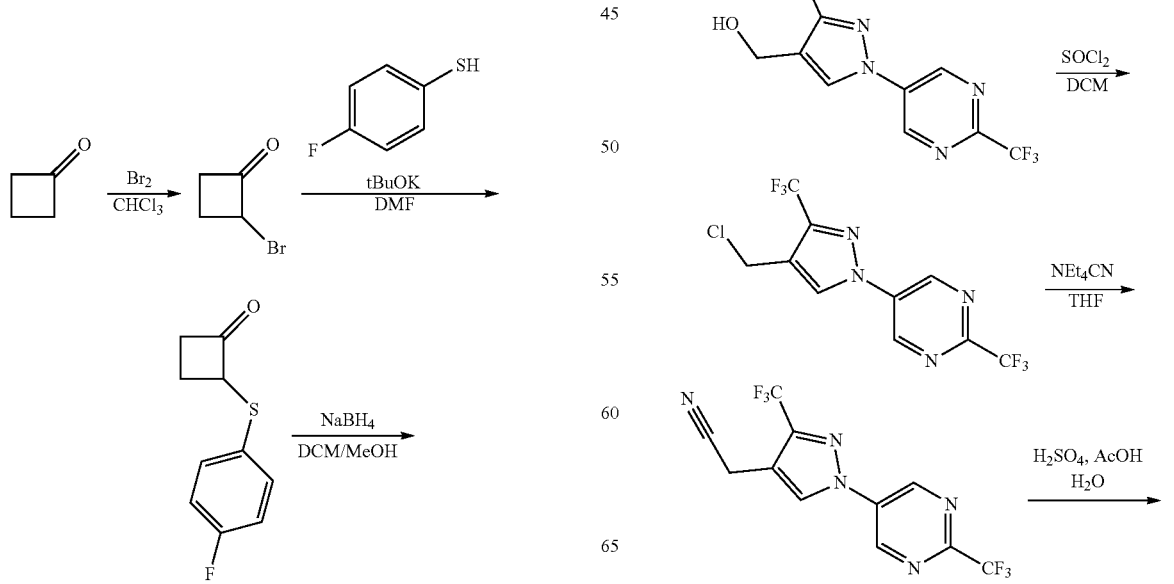

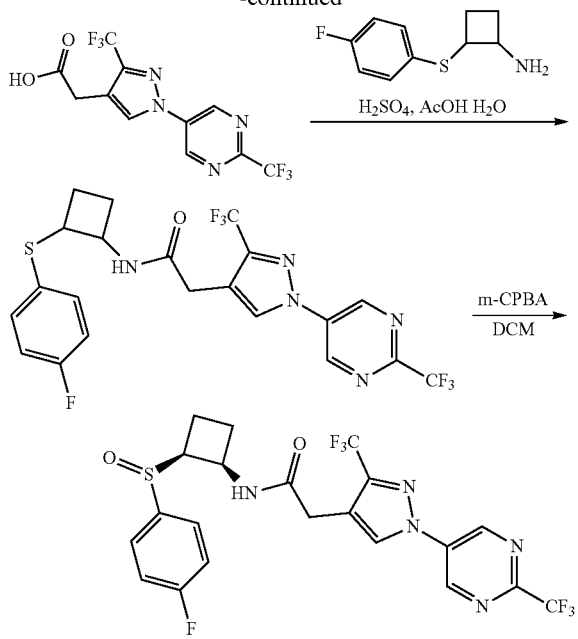

Example 2, Step 1: Preparation of 2-bromocyclobutanone

Step 1 proceeded according to the following scheme:

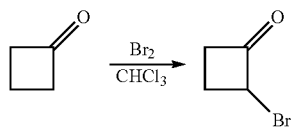

A solution of Br$_2$ (3.5 g, 14.11 mmol, 1.0 equiv) in chloroform (20 mL) was added to a solution of cyclobutanone (1 g, 14.26 mmol, 1.0 equiv) in chloroform (50 mL) dropwise with stirring at 0° C. The resulting solution was stirred for overnight at room temperature, diluted with 50 mL of chloroform, washed with 100 mL of H$_2$O, dried over anhydrous sodium sulfate, and concentrated under vacuum. This resulted in 1.2 g (56%) of 2-bromocyclobutan-1-one as a yellow liquid.

Example 2, Step 2: Preparation of 2-(4-fluorophenylthio)cyclobutanone

Step 2 proceeded according to the following scheme:

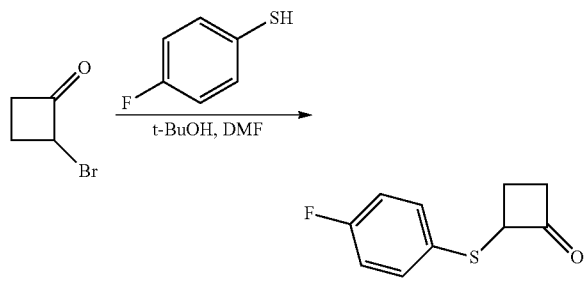

t-BuOH/THF (1M) (8 mL, 71.29 mmol, 8.9 equiv) was added to a solution of 4-fluorobenzene-1-thiol (900 mg, 7.02 mmol, 0.8 equiv) in N,N-dimethylformamide (30 mL) dropwise at 0° C. and stirred for 20 min under nitrogen. To the above was added a solution of 2-bromocyclobutan-1-one (1.2 g, 8.05 mmol, 1.0 equiv) in DMF (5 mL) dropwise and the mixture was stirred for an additional 1 h at room temperature. The reaction was then quenched with water, extracted with ethyl acetate, dried over anhydrous sodium sulfate, and concentrated under vacuum. The residue was purified by a silica gel column eluting with ethyl acetate/petroleum ether (1:10) to afford the title compound (1 g, 61%) as yellow oil.

Example 2, Step 3: Preparation of 2-(4-fluorophenylthio)cyclobutanol

Step 3 proceeded according to the following scheme:

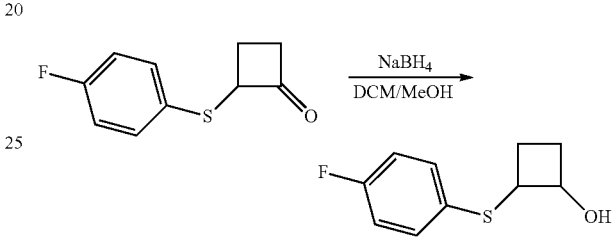

A solution of 2-[(4-fluorophenyl)sulfanyl]cyclobutan-1-one (900 mg, 4.58 mmol, 1.0 equiv) in dichloromethane (5 mL) was added to a mixture of NaBH$_4$ (262 mg, 6.92 mmol, 1.5 equiv), DCM (20 mL), methanol (10 mL) dropwise at 0° C. and stirred for 1 h. The reaction was then quenched with water, extracted with dichloromethane, dried over anhydrous sodium sulfate, and concentrated under vacuum. The residue was purified by a silica gel column eluting with ethyl acetate/petroleum ether (1:10) to afford the title compound (800 mg, 88%) as colorless oil.

Example 2, Step 4: Preparation of 2-(2-(4-fluorophenylthio)cyclobutyl)isoindoline-1,3-dione Step 4 proceeded according to the following scheme:

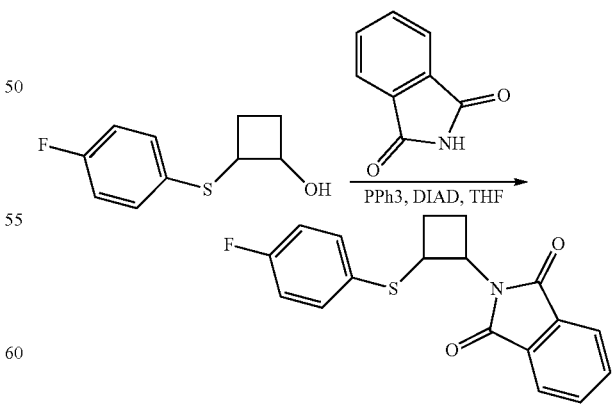

DIAD (1.5 g, 7.41 mmol, 2.0 equiv) was added to a solution of 2-[(4-fluorophenyl)sulfanyl]cyclobutan-1-ol (750 mg, 3.78 mmol, 2.0 equiv), 2,3-dihydro-1H-isoindole-1,3-dione (1.1 g, 7.47 mmol, 1.0 equiv), and PPh$_3$ (2 g, 7.62 mmol, 2.0 equiv) in THF (30 mL) dropwise and stirred overnight at room temperature. The resulting mixture was concentrated under vacuum. The residue was purified by a silica gel column eluting with ethyl acetate/petroleum ether (1:5) to afford the title compound (850 mg, 35%) as a white solid. LC-MS (ESI): [M+H]$^+$=328.1.

Example 2, Step 5: Preparation of 2-(4-fluorophenylthio)cyclobutanamine

Step 5 proceeded according to the following scheme:

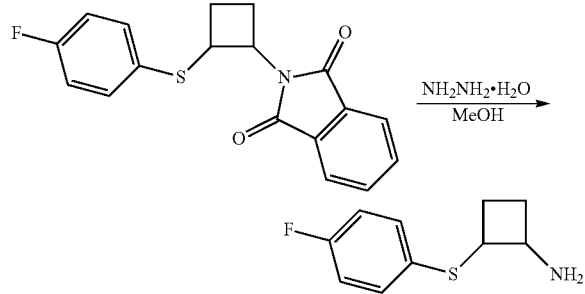

A solution of 2-[2-[(4-fluorophenyl)sulfanyl]cyclobutyl]-octahydro-1H-isoindole-1,3-dione (850 mg, 2.54 mmol, 1.0 equiv) and NH$_2$NH$_2$·H$_2$O (20 mL, 80%) in methanol (20 mL) was stirred overnight at room temperature. The resulting mixture was concentrated under vacuum. The residue was dissolved in ethyl acetate. The solid was filtered out and the filtrate was concentrated under vacuum. This resulted in the title compound (170 mg, 34%) as yellow oil. LC-MS (ESI): [M+H]$^+$=198.1.

Example 2, Step 6: Preparation of N-(2-(4-fluorophenylthio)cyclobutyl)-2-(3-(trifluoromethyl)-1-(2-(trifluoromethyl)pyrimidin-5-yl)-1H-pyrazol-4-yl)acetamide Step 6 proceeded according to the following scheme:

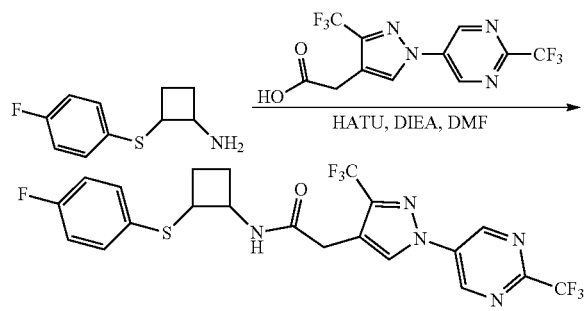

A solution of 2-[(4-fluorophenyl)sulfanyl]cyclobutan-1-amine (400 mg, 2.02 mmol, 1.0 equiv), 2-[3-(trifluoromethyl)-1-[2-(trifluoromethyl)pyrimidin-5-yl]-1H-pyrazol-4-yl]acetic acid (690 mg, 2.02 mmol, 1.0 equiv), DIEA (524 mg, 4.05 mmol, 2.0 equiv), HATU (926 mg, 2.43 mmol, 1.2 equiv) in DMF (10 mL) was stirred for 2 h at room temperature. The resulting solution was diluted with 100 ml of ethyl acetate, washed with H$_2$O, dried over sodium sulfate, and concentrated under vacuum. The residue was purified by silica gel column eluting with ethyl acetate/petroleum ether (1:1) to afford the title compound (750 mg, 71%) as a yellow solid. LC-MS (ESI): [M+H]$^+$=520.1.

Example 2, Step 7: Preparation of N-((1R,2S)-2-(4-fluorophenylsulfinyl)cyclobutyl)-2-(3-(trifluoromethyl)-1-(2-(trifluoromethyl)pyrimidin-5-yl)-1H-pyrazol-4-yl)acetamide Step 7 proceeded according to the following scheme:

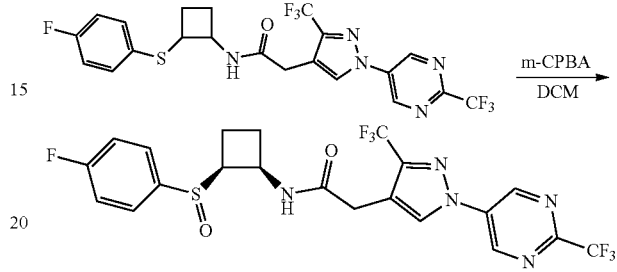

mCPBA (298 mg, 1.72 mmol, 1.2 equiv) was added to a solution of N-[2-[(4-fluorophenyl)sulfanyl]cyclobutyl]-2-[3-(trifluoromethyl)-1-[2-(trifluoromethyl)pyrimidin-5-yl]-1H-pyrazol-4-yl]acetamide (750 mg, 1.44 mmol, 1.0 equiv) in DCM (20 mL) in portions and stirred for 3 h at room temperature. The resulting mixture was concentrated under vacuum. The residue was purified by a silica gel column eluting with ethyl acetate/petroleum ether (2:1). The crude product was purified by Chiral-Prep-HPLC to afford N-((1R,2S)-2-(4-fluorophenylsulfinyl)cyclobutyl)-2-(3-(trifluoromethyl)-1-(2-(trifluoromethyl)pyrimidin-5-yl)-1H-pyrazol-4-yl)acetamide (13.3 mg, 1.7%) as a white solid. $t_R$=1.09 min. (Chiralpak IB4.6*250 mm, 5 um HPLC Chiral-A(IB) 001IB00CE-LA026, Hex (0.1% DEA):EtOH=80:20, 1 ml/min). LC-MS (ESI): [M+H]$^+$=536.1; $^1$H-NMR (400 MHz, CDCl3) δ 9.36 (s, 2H), 8.45 (s, 1H), 7.54-7.51 (m, 2H), 7.28-7.23 (m, 2H), 6.87-6.85 (m, 1H), 5.16-5.07 (m, 1H), 3.79-3.68 (m, 2H), 3.58-3.53 (m, 1H), 2.51-2.40 (m, 2H), 2.18-2.08 (m, 1H), 1.85-1.81 (m, 1H).

Seven additional stereoisomers were isolated from the Chiral-Prep-HPLC resolution.

Isomer 1: (13.0 mg, 1.6%) as a white solid. $t_R$=1.43 min. (Chiralpak IB4.6*250 mm, 5 um HPLC Chiral-A(IB) 001IB00CE-LA026, Hex (0.1% DEA):EtOH=80:20, 1 ml/min). LC-MS (ESI): [M+H]$^+$=536.1; $^1$H-NMR (400 MHz, CDCl3) δ 9.36 (s, 2H), 8.45 (s, 1H), 7.54-7.51 (m, 2H), 7.28-7.23 (m, 2H), 6.87-6.85 (m, 1H), 5.16-5.07 (m, 1H), 3.79-3.68 (m, 2H), 3.58-3.53 (m, 1H), 2.51-2.40 (m, 2H), 2.18-2.08 (m, 1H), 1.85-1.81 (m, 1H).

Isomer 2: (15.7 mg, 2%) as a white solid. $t_R$=4.19 min. (Chiralpak IB4.6*250 mm, 5 um HPLC Chiral-A(IB) 001IB00CE-LA026, Hex (0.1% DEA):EtOH=90:10, 1 ml/min). LC-MS (ESI): [M+H]$^+$=536.1; $^1$H NMR (300 MHz, CDCl3) δ 9.32 (s, 2H), 8.34 (s, 1H), 7.64-7.58 (m, 2H), 7.54-7.48 (m, 1H), 7.28-7.16 (m, 2H), 5.01-4.94 (m, 1H), 3.75-3.67 (m, 2H), 3.55-3.38 (m, 2H), 2.53 (m, 1H), 2.46-2.29 (m, 3H).

Isomer 3: (27.2 mg, 3.5%) as a white solid. $t_R$=5.10 min. (Chiralpak IB4.6*250 mm, 5 um HPLC Chiral-A(IB) 001IB00CE-LA026, Hex (0.1% DEA):EtOH=90:10, 1 ml/min). LC-MS (ESI): [M+H]$f$=536.1; $^1$H NMR (300 MHz, CDCl3) δ 9.32 (s, 2H), 8.34 (s, 1H), 7.64-7.58 (m, 2H), 7.54-7.48 (m, 1H), 7.28-7.16 (m, 2H), 5.01-4.94 (m, 1H), 3.75-3.67 (m, 2H), 3.55-3.38 (m, 2H), 2.53 (m, 1H), 2.46-2.29 (m, 3H).

Isomer 4: (67.9 mg, 8.7%) as a white solid. $t_R$=3.98 min. (Chiralpak IB4.6*250 mm, 5 um HPLC Chiral-A(IB) 001IB00CE-LA026, Hex (0.1% DEA):IPA=70:30, 1.5 ml/min). LC-MS (ESI): [M+H]$^+$=536.1; $^1$H NMR (300 MHz, CDCl3) δ 9.38 (s, 2H), 8.39 (s, 1H), 7.63-7.59 (m, 2H), 7.18-7.13 (m, 2H), 5.73-5.71 (m, 1H), 4.72-4.68 (m, 1H), 3.76-3.73 (m, 1H), 3.34-3.24 (m, 2H), 2.40-2.34 (m, 1H), 2.20-1.98 (m, 3H).

Isomer 5: (69.7 mg, 9.0%) as a white solid. $t_R$=4.81 min. (Chiralpak IB4.6*250 mm, 5 um HPLC Chiral-A(IB) 001IB00CE-LA026, Hex (0.1% DEA):IPA=70:30, 1.5 ml/min). LC-MS (ESI): [M+H]$^+$=536.1; $^1$H NMR (300 MHz, CDCl3) δ 9.38 (s, 2H), 8.39 (s, 1H), 7.63-7.59 (m, 2H), 7.18-7.13 (m, 2H), 5.73-5.71 (m, 1H), 4.72-4.68 (m, 1H), 3.76-3.73 (m, 1H), 3.34-3.24 (m, 2H), 2.40-2.34 (m, 1H), 2.20-1.98 (m, 3H).

Isomer 6: (31.4 mg, 4.1%) as a white solid. tR=3.35 min. (Chiralpak IB4.6*250 mm, 5 um HPLC Chiral-A(IB) 001IB00CE-LA026, Hex (0.1% DEA):EtOH=80:20, 1 ml/min). LC-MS (ESI): [M+H]$^+$=536.1; $^1$H NMR (300 MHz, CDCl3) δ 9.35 (s, 2H), 8.54 (s, 1H), 7.57-7.54 (m, 2H), 7.22-7.18 (m, 2H), 6.21-6.09 (m, 1H), 4.60-4.51 (m, 1H), 3.72-3.55 (m, 3H), 2.29-2.35 (m, 1H), 2.17-1.99 (m, 2H), 1.63-1.55 (m, 1H).

Isomer 7: (24.7 mg, 3.2%) as a white solid. $t_R$=4.03 min. (Chiralpak IB4.6*250 mm, 5 um HPLC Chiral-A(IB) 001IB00CE-LA026, Hex (0.1% DEA):EtOH=80:20, 1 ml/min). LC-MS (ESI): [M+H]$^+$=536.1; $^1$H NMR (300 MHz, CDCl3) δ 9.35 (s, 2H), 8.54 (s, 1H), 7.57-7.54 (m, 2H), 7.22-7.18 (m, 2H), 6.21-6.09 (m, 1H), 4.60-4.51 (m, 1H), 3.72-3.55 (m, 3H), 2.29-2.35 (m, 1H), 2.17-1.99 (m, 2H), 1.63-1.55 (m, 1H).

Example 3: N-((1S, 2R)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide The overall Example 3 reaction scheme was as follows:

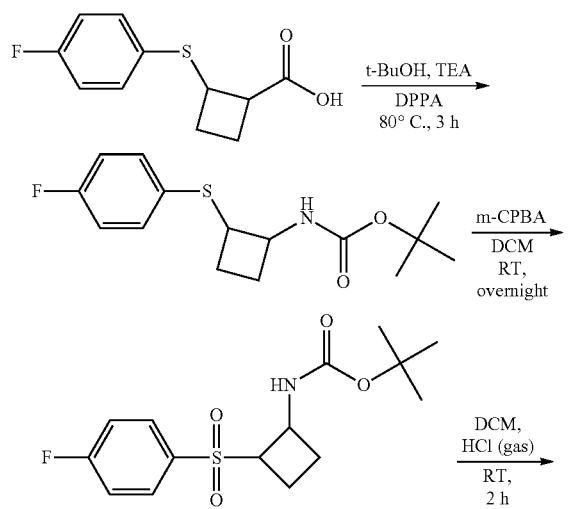

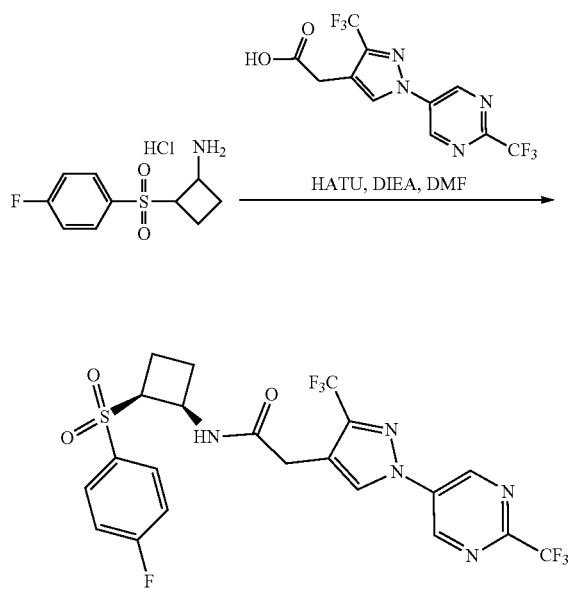

Example 3, Step 1: Preparation of 2-((4-fluorophenyl)thio)cyclobutanecarboxylic acid Step 1 proceeded according to the following scheme:

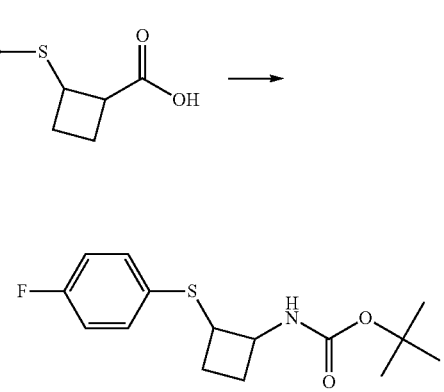

To a 3000-mL 4-necked round-bottom flask purged and maintained with an inert atmosphere of nitrogen was placed 2-[(4-fluorophenyl)sulfanyl]cyclobutane-1-carboxylic acid (220 g, 972.30 mmol, 1.00 equiv), and 2-methylpropan-2-ol (2.4 L) and TEA (171 g, 1.69 mol, 1.60 equiv) followed by the addition of DPPA (350 g, 1.27 mol, 1.20 equiv) dropwise with stirring at 60° C. The resulting solution was stirred at 80° C. for 3 h, cooled to 25° C. with a water/ice bath, and concentrated under vacuum. The residue was then quenched by the addition of 600 mL of water/ice. The resulting solution was extracted with 3×800 mL of ethyl acetate. The organic layers were combined, washed with 1×500 mL of brine, dried over anhydrous sodium sulfate, and concentrated under vacuum. The residue was applied onto a silica gel column eluted with ethyl acetate/petroleum ether (1:50) to afford 130 g (45%) of tert-butyl N-[2-[(4-fluorophenyl)sulfanyl]cyclobutyl]carbamate as a white solid.

Example 3, Step 2: Preparation of tert-butyl (2-((4-fluorophenyl)sulfonyl)cyclobutyl) carbamate Step 2 proceeded according to the following scheme:

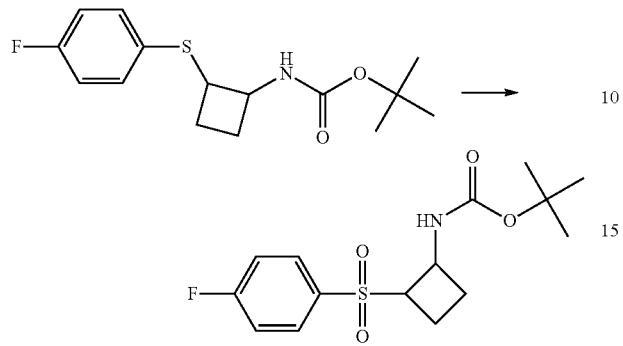

To a 2000-mL 4-necked round-bottom flask purged and maintained with an inert atmosphere of nitrogen was placed tert-butyl N-[2-[(4-fluorophenyl)sulfanyl]cyclobutyl]carbamate (120 g, 403.51 mmol, 1.00 equiv) and dichloromethane (1.5 L) followed by the addition of m-CPBA (205 g, 1.19 mol, 3.00 equiv) in portions with stirring in an ice/water bath. The resulting solution was stirred overnight at room temperature, cooled with a water/ice bath, and quenched by the addition of 50 mL of ice aqueous sodium carbonate. The pH value of the solution was adjusted to 9 with aqueous sodium carbonate. The resulting solution was extracted with 2×800 mL of dichloromethane. The organic layers were combined, washed with 1×500 mL of brine, dried over anhydrous sodium sulfate and concentrated under vacuum. The residue was applied onto a silica gel column eluted with ethyl acetate/petroleum ether (1:15-1:10-1:5) to afford 92 g (24 g of A, 64 g of B, 4 g of C) of tert-butyl N-[2-[(4-fluorobenzene)sulfonyl]-cyclobutyl]carbamate as a white solid.

Example 3, Step 3: Preparation of 2-((4-fluorophenyl)sulfonyl)cyclobutanamine hydrochloride Step 3 proceeded according to the following scheme:

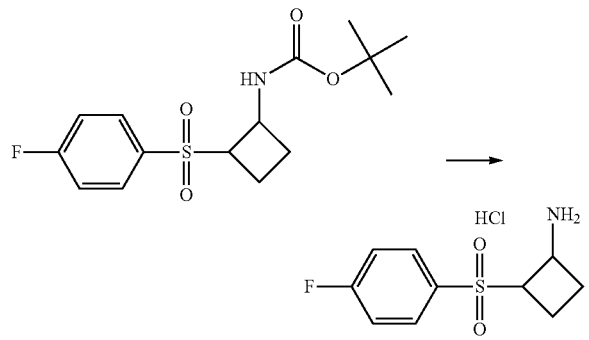

To a 500-mL 3-necked round-bottom flask purged and maintained with an inert atmosphere of nitrogen was placed tert-butyl N-[2-[(4-fluorobenzene)sulfonyl]cyclobutyl]carbamate (24/35/4 g in three batches, 72.86 mmol, 1.00 equiv) and dichloromethane (240/350/40 mL) followed by introducing hydrogen chloride (gas). The resulting solution was stirred at room temperature for 2 h, concentrated under vacuum, washed with 2×30 mL of ether to afford 17 (A)/23 (B)/2.4 (C) g (88%) of 2-[(4-fluorobenzene)sulfonyl]cyclobutan-1-amine hydrochloride as a white solid. LC-MS: (ES, m/z): (ES+[M+H]$^+$=230; $^1$H-NMR: (300 MHz, D2O, ppm): δ2.143-2.209 (m, 1H), 2.355-2.480 (m, 3H), 4.291-4.400 (m, 2H), 7.331-7.390 (m, 2H), 7.926-7.972 (m, 2H).

Example 3, Step 4: Preparation of N-((1R, 2S)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide Step 4 proceeded according to the following scheme:

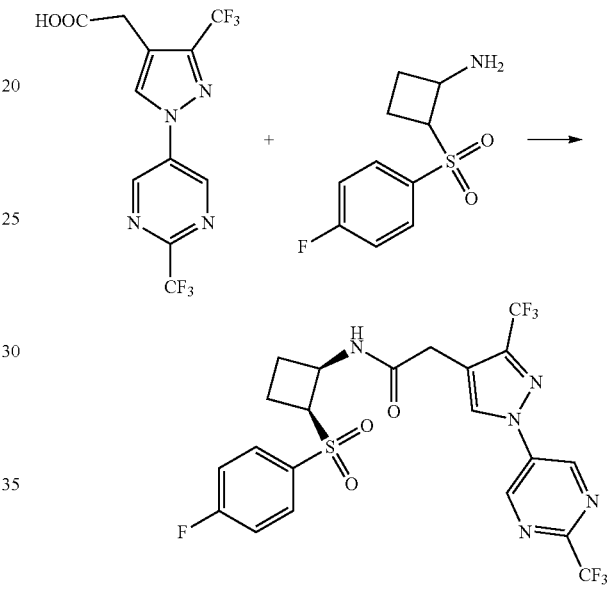

A solution of 2-[3-(trifluoromethyl)-1-[2-(trifluoromethyl)pyrimidin-5-yl]-1H-pyrazol-4-yl]acetic acid (6.2 g, 18.22 mmol, 1.0 equiv), 2-[(4-fluorobenzene)sulfonyl]cyclobutan-1-amine (3.7 g, 16.13 mmol, 0.8 equiv), HATU (10.3 g, 27.08 mmol, 1.4 equiv) and DIEA (7.04 g, 54.47 mmol, 2.9 equiv) in DMF (50 mL) was stirred for 12 h at room temperature. The resulting solution was diluted with ethyl acetate, washed with brine, dried over anhydrous sodium sulfate, and concentrated under vacuum. The crude product was purified by Prep-SFC to afford N-((1R,2S)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide (1.1 g, 11%) as a white solid. $t_R$=1.51 min. (CHIRALCEL OD-3(SFC2)4.6*100 mm, 3 um UPC Chiral-A(OD-H)0050D30CS-MH018; MeOH (0.1% DEA)=10%, 4 mL/min). LC-MS (ESI): [M+H]$^+$=552.1; $^1$H NMR (400 MHz, CDCl3) δ 9.35 (s, 2H), 8.52 (s, 1H), 7.91-7.88 (m, 2H), 7.29-7.25 (m, 2H), 6.69 (d, J=8.8 Hz, 1H), 5.22-5.13 (m, 1H), 4.06-4.04 (m, 1H), 3.71-3.62 (m, 2H), 2.61-2.48 (m, 2H), 2.11-207 (m, 2H). The crude product also yielded N-((1 S,2R)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide (1.2 g, 12%) as a white solid. $t_R$=2.14 min. (CHIRALCEL OD-3(SFC2)4.6*100 mm, 3 um UPC Chiral-A(OD-H)0050D30CS-MH018; MeOH (0.1% DEA)=10%, 4 mL/min) LC-MS (ESI):[M+H]$^+$=552.1; $^1$H NMR (400 MHz, CDCl3) δ 9.35 (s, 2H), 8.52 (s, 1H), 7.91-7.88 (m, 2H), 7.29-7.25 (m, 2H), 6.69 (d, J=8.8 Hz, 1H), 5.22-5.13 (m, 1H), 4.06-4.04 (m, 1H), 3.71-3.62 (m, 2H), 2.61-2.48 (m, 2H), 2.11-207 (m, 2H).

Example 4: Preparation of (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide The overall Example 4 reaction scheme was as follows:

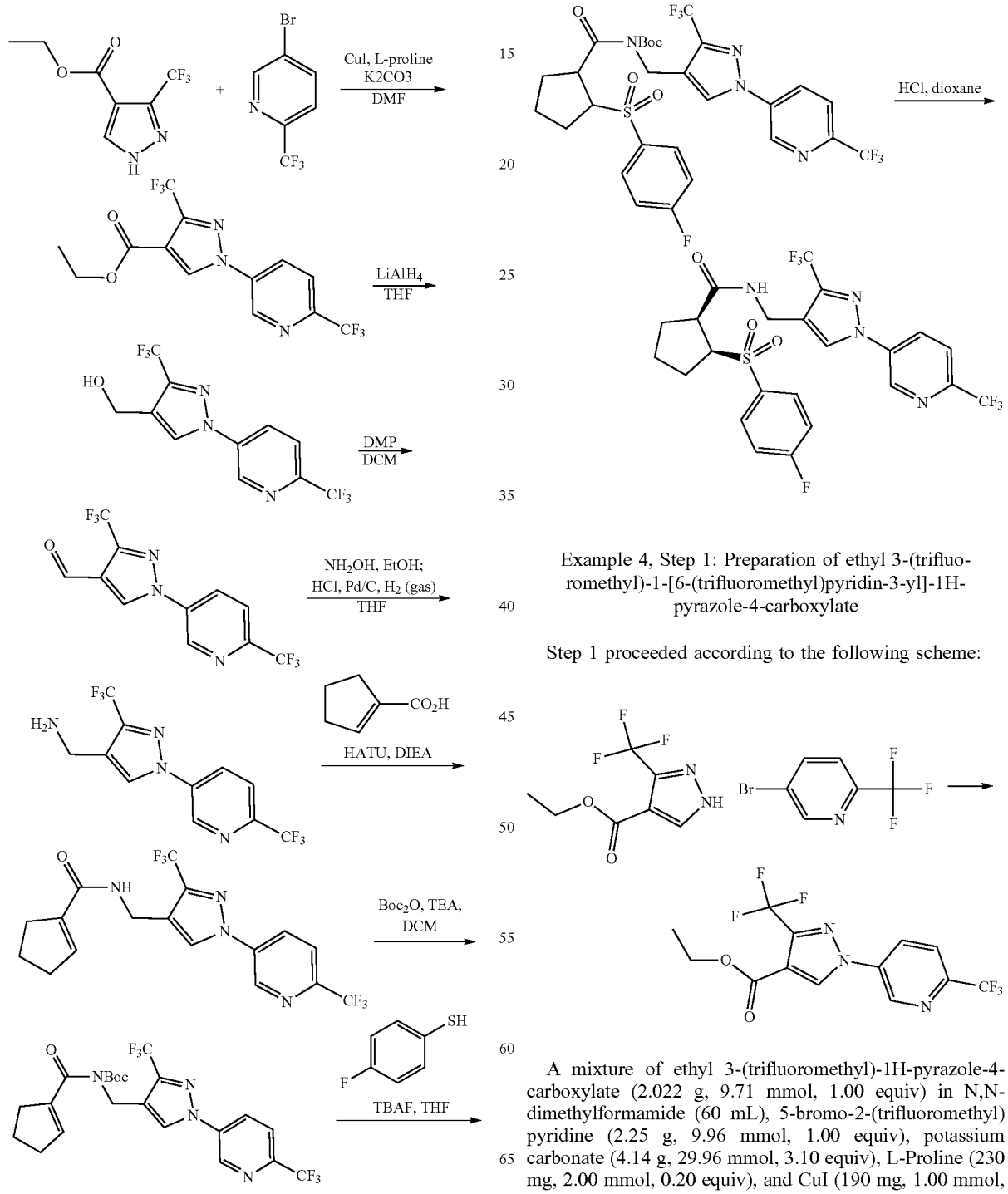

Example 4, Step 1: Preparation of ethyl 3-(trifluoromethyl)-1-[6-(trifluoromethyl)pyridin-3-yl]-1H-pyrazole-4-carboxylate Step 1 proceeded according to the following scheme:

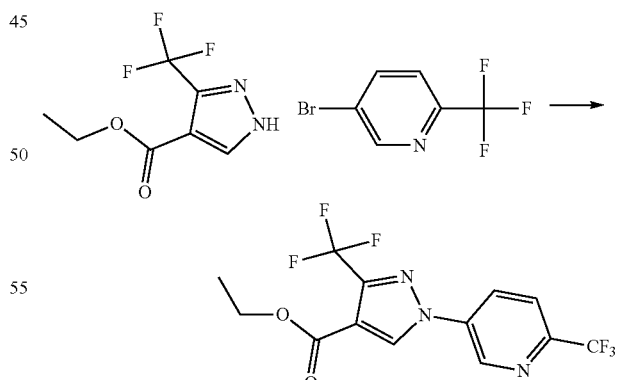

A mixture of ethyl 3-(trifluoromethyl)-1H-pyrazole-4-carboxylate (2.022 g, 9.71 mmol, 1.00 equiv) in N,N-dimethylformamide (60 mL), 5-bromo-2-(trifluoromethyl)pyridine (2.25 g, 9.96 mmol, 1.00 equiv), potassium carbonate (4.14 g, 29.96 mmol, 3.10 equiv), L-Proline (230 mg, 2.00 mmol, 0.20 equiv), and CuI (190 mg, 1.00 mmol, 0.10 equiv) was stirred overnight at 100° C. in an oil bath under nitrogen. The solid was filtered out. The resulting solution was diluted with brine, extracted with ethyl acetate, washed with brine, dried over anhydrous sodium sulfate and concentrated under vacuum. The residue was purified by a silica gel column eluting with ethyl acetate/petroleum ether (5:100) to afford the title compound (1.47 g, 43%) as a white solid. LC-MS (ESI): [M+H]$^+$=354.1.

Example 4: Step 2: Preparation of [3-(trifluoromethyl)-1-[6-(trifluoromethyl)pyridin-3-yl]-1H-pyrazol-4-yl]methanol Step 2 proceeded according to the following scheme:

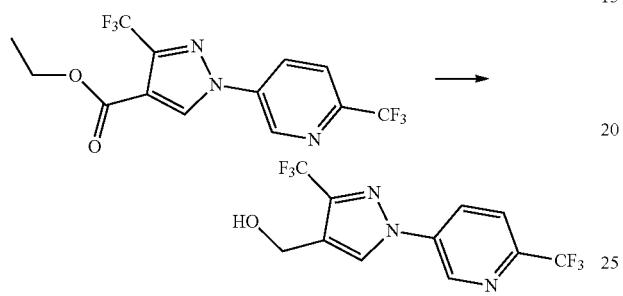

LiAlH$_4$ (190 mg, 5.01 mmol, 1.20 equiv) was added in several batches into a solution of ethyl 3-(trifluoromethyl)-1-[6-(trifluoromethyl)pyridin-3-yl]-1H-pyrazole-4-carboxylate (1.47 g, 4.16 mmol, 1.00 equiv) in tetrahydrofuran (30 mL) at 0° C. under nitrogen. The resulting solution was stirred for 30 min at 0° C. in an ice/salt bath. The reaction was then quenched by the addition of 10 mL of NaOH (1 mol/L). The resulting mixture was filtered. The solution was diluted with water, extracted with ethyl acetate, washed with brine, dried over anhydrous sodium sulfate and concentrated under vacuum. This resulted in the title compound (1.257 g, 97%) as a yellow solid. LC-MS (ESI): [M+H]$^+$= 312.0.

Example 4, Step 3: Preparation of 3-(trifluoromethyl)-1-[6-(trifluoromethyl)pyridin-3-yl]-1H-pyrazole-4-carbaldehyde Step 3 proceeded according to the following scheme:

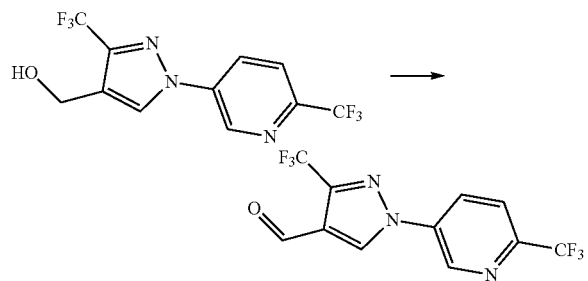

A mixture of [3-(trifluoromethyl)-1-[6-(trifluoromethyl)pyridin-3-yl]-1H-pyrazol-4-yl]methanol (1.257 g, 4.04 mmol, 1.00 equiv) in dichloromethane (40 mL), and DMP (2.06 g, 4.86 mmol, 1.20 equiv) was stirred for 3 h at room temperature. The resulting solution was diluted with ethyl acetate, washed with saturated solution of sodium bicarbonate and brine, dried over anhydrous sodium sulfate and concentrated under vacuum. The residue was purified by silica gel column eluting with ethyl acetate/petroleum ether (7:100). This resulted in the title compound (1.13 g, 90%) as a light yellow solid. LC-MS (ESI): [M+H]$^+$=310.0.

Example 4, Step 4: Preparation of [3-(trifluoromethyl)-1-[6-(trifluoromethyl)pyridin-3-yl]-1H-pyrazol-4-yl]methanamine Step 4 proceeded according to the following scheme:

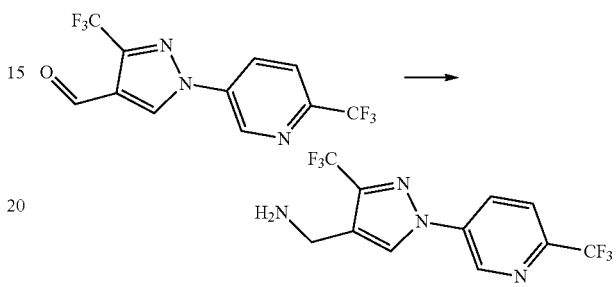

A mixture of 3-(trifluoromethyl)-1-[6-(trifluoromethyl)pyridin-3-yl]-1H-pyrazole-4-carbaldehyde (500 mg, 1.62 mmol, 1.00 equiv) in ethanol (40 mL), NH$_2$OH.HCl (230 mg, 3.31 mmol, 2.00 equiv), and water (5 mL) was stirred for 2 h at room temperature. Concentrated hydrogen chloride (2 mL), Pd/C (100 mg, 10%) was added into the mixture. The resulting mixture was stirred for 1 h at room temperature under hydrogen. The solids were filtered out. The resulting solution was diluted with water. The pH value of the solution was adjusted to 9 with sodium carbonate. The resulting solution was extracted with ethyl acetate, dried over anhydrous sodium sulfate and concentrated under vacuum. This resulted in the title compound (800 mg, crude) as a yellow solid, which was used for the next step without any further purification. LC-MS (ESI): [M+H]$^+$=311.1.

Example 4, Step 5: Preparation of N-[[3-(trifluoromethyl)-1-[6-(trifluoromethyl)pyridin-3-yl]-1H-pyrazol-4-yl]methyl]cyclopent-1-ene-1-carboxamide Step 5 proceeded according to the following scheme:

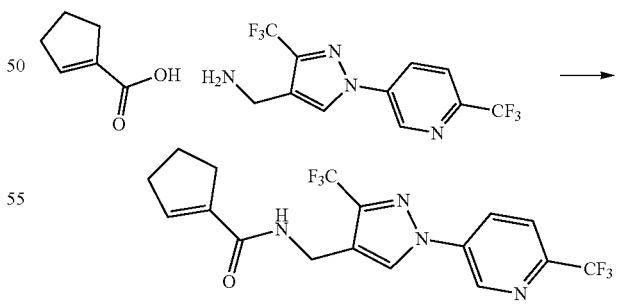

A mixture of [3-(trifluoromethyl)-1-[6-(trifluoromethyl)pyridin-3-yl]-1H-pyrazol-4-yl]methanamine (1.84 g, 5.93 mmol, 1.00 equiv) in N,N-dimethylformamide (100 mL), cyclopent-1-ene-1-carboxylic acid (1.008 g, 8.99 mmol, 1.50 equiv), DIEA (7.74 g, 59.89 mmol, 10.10 equiv), HATU (3.04 g, 8.00 mmol, 1.30 equiv) was stirred overnight at room temperature. The reaction was diluted with water, extracted with ethyl acetate, washed with brine, dried over anhydrous sodium sulfate and concentrated under vacuum. The residue was purified by a silica gel column eluting with ethyl acetate/petroleum ether (10:100) to afford the title compound (1.13 g, 47%) as a light yellow solid. LC-MS (ESI): [M+H]$^+$=405.1.

Example 4, Step 6: Preparation of tert-butyl N-[(cyclopent-1-en-1-yl)carbonyl]-N-[[3-(trifluoromethyl)-1-[6-(trifluoromethyl)pyridin-3-yl]-1H-pyrazol-4-yl]methyl]carbamate Step 6 proceeded according to the following scheme:

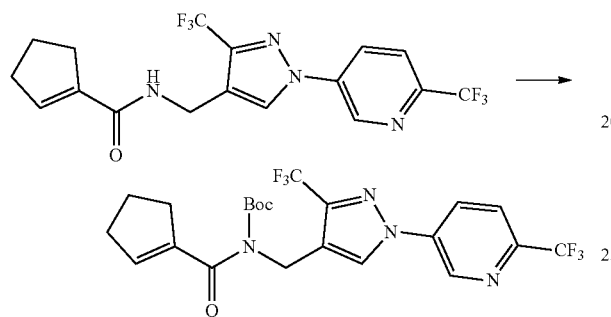

A mixture of N-[[3-(trifluoromethyl)-1-[6-(trifluoromethyl)pyridin-3-yl]-1H-pyrazol-4-yl]methyl]cyclopent-1-ene-1-carboxamide (1.4 g, 3.46 mmol, 1.00 equiv) in dichloromethane (40 mL), TEA (1.05 g, 10.38 mmol, 3.00 equiv), and Boc$_2$O (7.6 g, 34.82 mmol, 10.10 equiv) was stirred overnight at room temperature. The resulting solution was diluted with ethyl acetate, washed with brine, dried over anhydrous sodium sulfate and concentrated under vacuum. The residue was purified by a silica gel column eluting with ethyl acetate/petroleum ether (7:100) to afford the title compound (1.28 g, 73%) as a light yellow solid. LC-MS (ESI): [M+H]$^+$=505.2.

Example 4, Step 7: Preparation of tert-butyl N-([2-[(4-fluorophenyl)sulfanyl]cyclopentyl]carbonyl)-N-[[3-(trifluoromethyl)-1-[6-(trifluoromethyl)pyridin-3-yl]-1H-pyrazol-4-yl]methyl]carbamate Step 7 proceeded according to the following scheme:

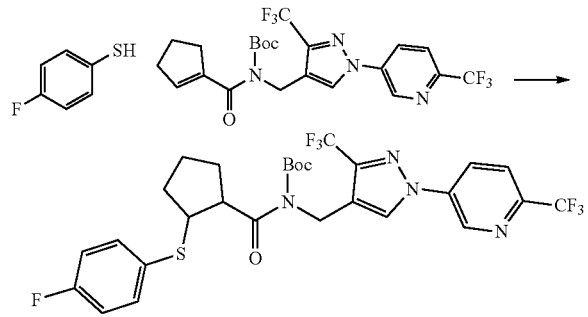

A solution of tert-butyl N-[(cyclopent-1-en-1-yl)carbonyl]-N-[[3-(trifluoromethyl)-1-[6-(trifluoromethyl)pyridin-3-yl]-1H-pyrazol-4-yl]methyl]carbamate (1.48 g, 2.93 mmol, 1.00 equiv) in tetrahydrofuran (20 mL), TBAF (261 mg, 1.00 mmol, 0.30 equiv), and 4-fluorobenzene-1-thiol (3 g, 23.41 mmol, 8.00 equiv) was stirred for overnight at room temperature. The reaction was then quenched by the addition of water. The resulting solution was extracted with ethyl acetate, washed with brine, dried over anhydrous sodium sulfate and concentrated under vacuum. The residue was purified by a silica gel column eluting with ethyl acetate/petroleum ether (8:100) to afford the title compound (1.6 g, 86%) as colorless oil. LC-MS (ESI): [M+H]$^+$=633.2.

Example 4, Step 8: Preparation of tert-butyl N-([2-[(4-fluorobenzene)sulfonyl]cyclopentyl]carbonyl)-N-[[3-(trifluoromethyl)-1-[6-(trifluoromethyl)pyridin-3-yl]-1H-pyrazol-4-yl]methyl]carbamate Step 8 proceeded according to the following scheme:

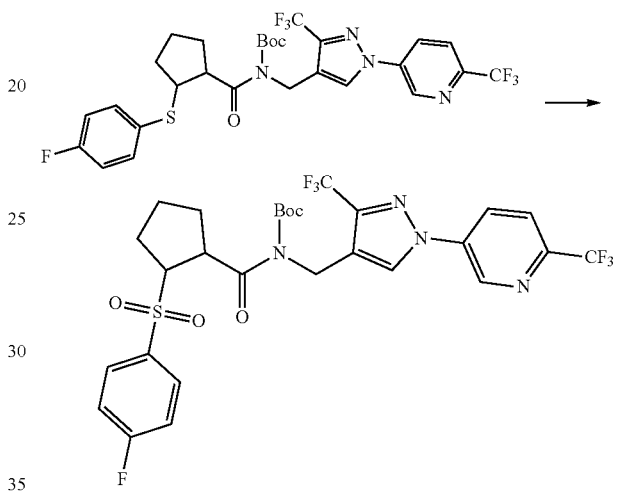

A solution of m-CPBA (42 mg, 0.24 mmol, 2.20 equiv) in ethyl acetate (1 mL) was added dropwise with stirring into a solution of tert-butyl N-([2-[(4-fluorophenyl)sulfanyl]cyclopentyl]carbonyl)-N-[[3-(trifluoromethyl)-1-[6-(trifluoromethyl)pyridin-3-yl]-1H-pyrazol-4-yl]methyl]carbamate (70 mg, 0.11 mmol, 1.00 equiv) in dichloromethane (10 mL) at 0° C. under nitrogen. The resulting solution was stirred for 30 min at 0° C. in an ice/salt bath. The reaction was then quenched by the addition of saturated solution of sodium bicarbonate, diluted with ethyl acetate, washed with brine, dried over anhydrous sodium sulfate and concentrated under vacuum. This resulted in the title compound (60 mg, 82%) as colorless oil. LC-MS (ESI): [M+H]$^+$=665.2.

Example 4, Step 9: Preparation of (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide Step 9 proceeded according to the following scheme:

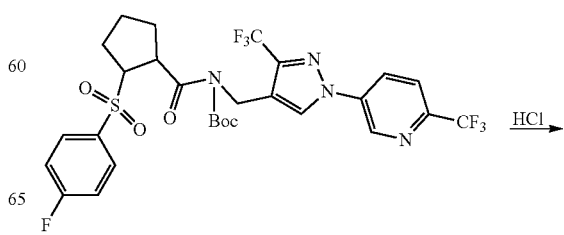

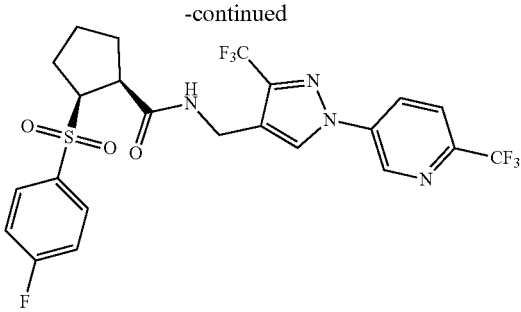

A mixture of tert-butyl N-[[2-(benzenesulfonyl)cyclopentyl]carbonyl]-N-[[3-(trifluoromethyl)-1-[6-(trifluoromethyl)pyridin-3-yl]-1H-pyrazol-4-yl]methyl]carbamate (1.2 g, 1.86 mmol, 1.00 equiv) and 4N of HCl in dioxane (50 mL) was stirred overnight at room temperature. The resulting mixture was concentrated under vacuum. The resulting solution was diluted with ethyl acetate, washed with saturated solution of sodium bicarbonate and brine, dried over anhydrous sodium sulfate and concentrated under vacuum. The residue was purified by a silica gel column eluting with ethyl acetate/petroleum ether (30:100). The crude product (1.2 g) was purified by Chiral-Prep-HPLC with the following conditions (Prep-HPLC-009): Column, Chiralpak IA, 2*25 cm, 5 um; mobile phase, Hex and ethanol (hold 30.0% ethanol in 18 min); Detector, UV 254/220 nm. This resulted in (1S,2S)-2-(4-fluorophenylsulfonyl)-N-((3-(trifluoromethyl)-1-(6-(trifluoromethyl)pyridin-3-yl)-1H-pyrazol-4-yl)methyl)cyclopentanecarboxamide (209.9 mg, 20%) as a white solid. $t_R$=8.02 min (CHIRALPAK IA-3, 0.46×15 cm, 3 μm, Hex:EtOH=70:30, 1.0 ml/min). LC-MS (ESI): [M+H]$^+$=565.1; $^1$H NMR (300 MHz, DMSO-d6) δ 9.24 (s, 1H), 8.80 (s, 1H), 8.52-8.42 (m, 2H), 8.14-8.11 (m, 1H), 7.94-7.90 (m, 2H), 7.50-7.45 (m, 2H), 4.27-3.97 (m, 3H), 3.08-3.02 (m, 1H), 2.28-2.22 (m, 1H), 1.93-1.77 (m, 4H), 1.64-1.50 (m, 1H).

Three more stereoisomers were also isolated from the Chiral-Prep-HPLC resolution.

Isomer 1: (179.9 mg, 17%) as a white solid. $t_R$=4.95 min (CHIRALPAK IA-3, 0.46×15 cm, 3 μm, Hex:EtOH=70:30, 1.0 ml/min). LC-MS (ESI): [M+H]$^+$=565.1; $^1$H NMR (300 MHz, DMSO-d6) δ 9.28 (s, 1H), 8.73 (s, 1H), 8.54-8.49 (m, 2H), 8.15-8.12 (m, 1H), 7.96-7.91 (m, 2H), 7.44-7.38 (m, 2H), 4.22-4.02 (m, 3H), 3.14-3.06 (m, 1H), 2.09-1.92 (m, 3H), 1.71-1.55 (m, 3H).

Isomer 2: (235.6 mg, 22%) as a white solid. $t_R$=6.01 min (CHIRALPAK IA-3, 0.46×15 cm, 3 μm, Hex:EtOH=70:30, 1.0 ml/min). LC-MS (ESI): [M+H]$^+$=565.1; $^1$H NMR (300 MHz, DMSO-d6) δ 9.24 (s, 1H), 8.80 (s, 1H), 8.52-8.42 (m, 2H), 8.14-8.11 (m, 1H), 7.94-7.90 (m, 2H), 7.50-7.45 (m, 2H), 4.27-4.00 (m, 3H), 3.08-3.04 (m, 1H), 2.28-2.22 (m, 1H), 1.93-1.77 (m, 4H), 1.70-1.50 (m, 1H).

Isomer 3: (155.7 mg, 15%) as a white solid. $t_R$=10.30 min (CHIRALPAK IA-3, 0.46×15 cm, 3 μm, Hex:EtOH=70:30, 1.0 ml/min). LC-MS (ESI): [M+H]$^+$=565.1; $^1$H NMR (300 MHz, DMSO-d6) δ 9.28 (s, 1H), 8.73 (s, 1H), 8.54-8.49 (m, 2H), 8.15-8.12 (m, 1H), 7.96-7.92 (m, 2H), 7.44-7.37 (m, 2H), 4.20-4.01 (m, 3H), 3.14-3.06 (m, 1H), 2.05-1.92 (m, 3H), 1.73-1.55 (m, 3H).

Example 5: Preparation of (1R,2R)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide The overall Example 5 reaction scheme was as follows:

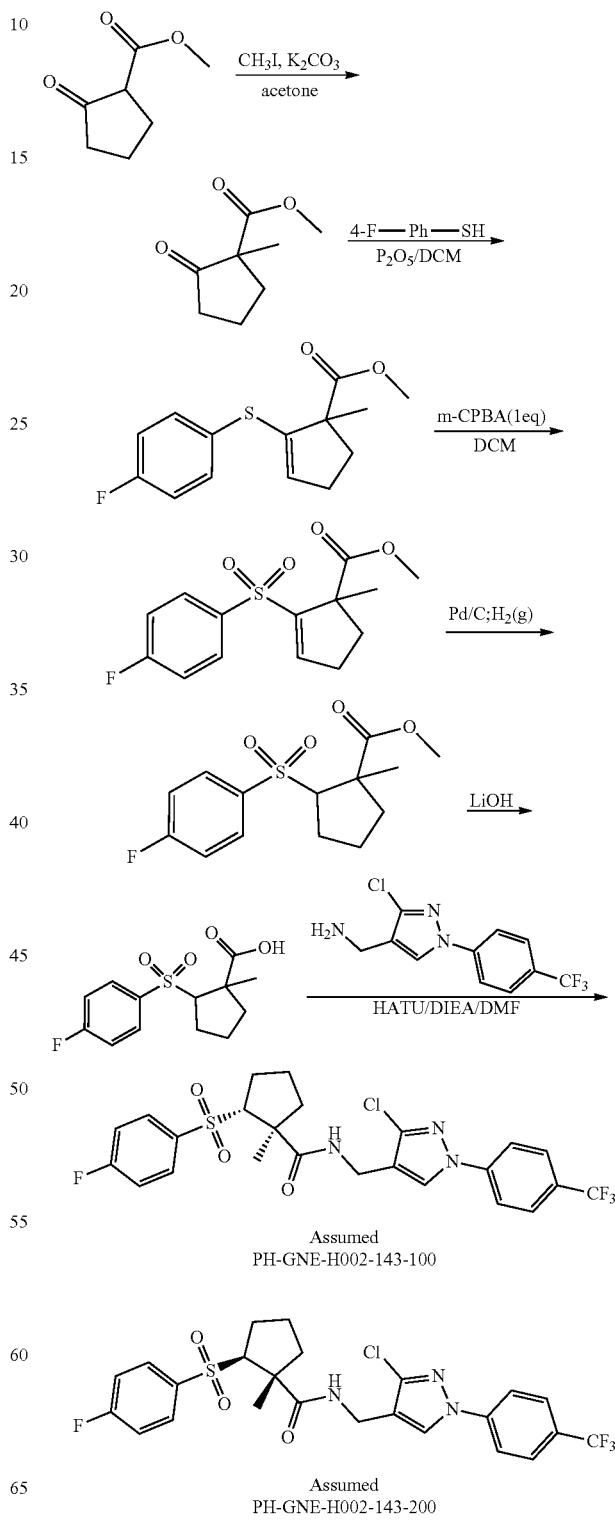

Assumed
PH-GNE-H002-143-100

Assumed
PH-GNE-H002-143-200

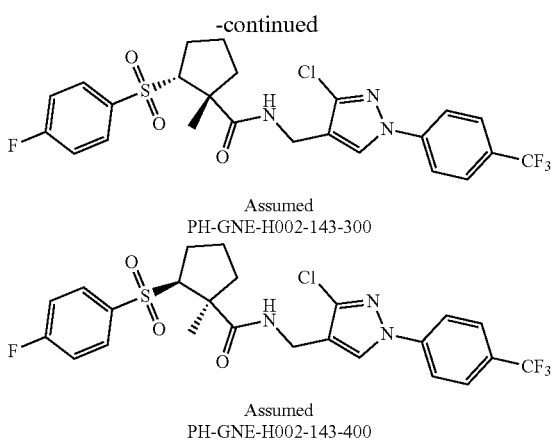

Assumed
PH-GNE-H002-143-300

Assumed
PH-GNE-H002-143-400

Example 5, Step 1: Preparation of methyl 1-methyl-2-oxocyclopentane-1-carboxylate Step 1 proceeded according to the following scheme:

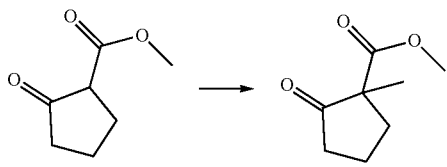

A mixture of methyl 2-oxocyclopentane-1-carboxylate (10 g, 70.35 mmol, 1.00 equiv) and K$_2$CO$_3$ (11.7 g, 84.04 mmol, 1.20 equiv) in acetone (100 mL) was stirred for 0.5 h at room temperature. This was followed by the addition of iodomethane (12 g, 84.54 mmol, 1.20 equiv) dropwise with stirring. The resulting solution was heated to reflux for 2 h. The reaction mixture was cooled to room temperature. The solids were filtered out. The filtrate was concentrated to afford the title compound (12 g, crude) as light yellow oil which was used for the next step without further purification.

Example 5, Step 2: Preparation of methyl 2-[(4-fluorophenyl)sulfanyl]-1-methylcyclopent-2-ene-1-carboxylate Step 2 proceeded according to the following scheme:

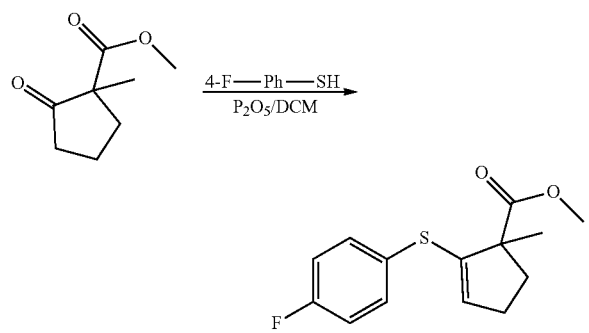

A mixture of methyl 1-methyl-2-oxocyclopentane-1-carboxylate (3.12 g, 19.98 mmol, 1.00 equiv), 4-fluorobenzene-1-thiol (2.56 g, 19.97 mmol, 1.00 equiv), phosphorus pentoxide (5.68 g, 40.02 mmol, 2.00 equiv), and dichloromethane (30 mL) was stirred for 18 h at room temperature. The resulting mixture was diluted with dichloromethane, washed with sodium hydroxide (10%) and brine, dried over anhydrous sodium sulfate and concentrated under vacuum. This resulted in the title compound (5.1 g, 96%) as light yellow oil which was used for the next step without further purification.

Example 5, Step 3: Preparation of methyl 2-[(4-fluorobenzene)sulfonyl]-1-methylcyclopent-2-ene-1-carboxylate Step 3 proceeded according to the following scheme:

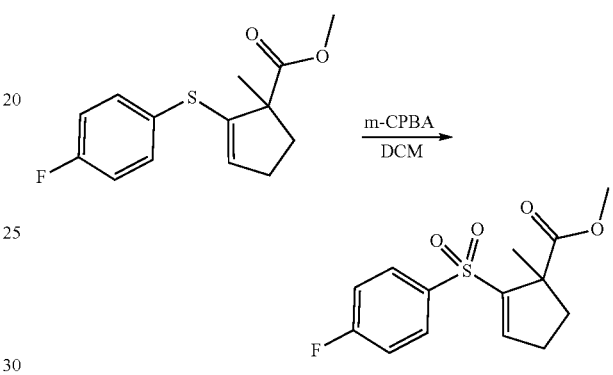

m-CPBA (8.93 g, 51.75 mmol, 3.00 equiv) was added in portions into a mixture of methyl 2-[(4-fluorophenyl)sulfanyl]-1-methylcyclopent-2-ene-1-carboxylate (4.6 g, 17.27 mmol, 1.00 equiv) in dichloromethane (150 mL). The resulting solution was stirred for 3 h at room temperature. The resulting mixture was washed with saturated solution of sodium bicarbonate and brine, dried over anhydrous sodium sulfate, and concentrated under vacuum. The residue was purified by a silica gel column eluting with ethyl acetate/petroleum ether (1:2) to afford the title compound (2.8 g, 54%) as a white solid.

Example 5, Step 4: Preparation of methyl 2-[(4-fluorobenzene)sulfonyl]-1-methylcyclopentane-1-carboxylate Step 4 proceeded according to the following scheme:

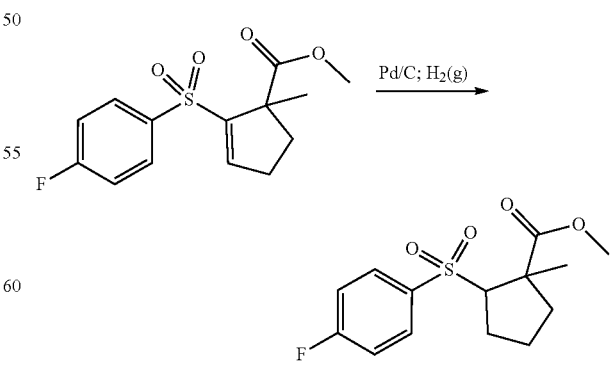

A mixture of methyl 2-[(4-fluorobenzene)sulfonyl]-1-methylcyclopent-2-ene-1-carboxylate (950 mg, 3.18 mmol, 1.00 equiv), ethyl acetate (50 mL), and Pd/C (2 g, 10%) was stirred for 2 h at room temperature under hydrogen. The solid was filtered out. The resulting mixture was concentrated under vacuum to afford the title compound (880 mg, crude) as colorless oil.

Example 5, Step 5: Preparation of 2-[(4-fluorobenzene)sulfonyl]-1-methylcyclopentane-1-carboxylic acid Step 5 proceeded according to the following scheme:

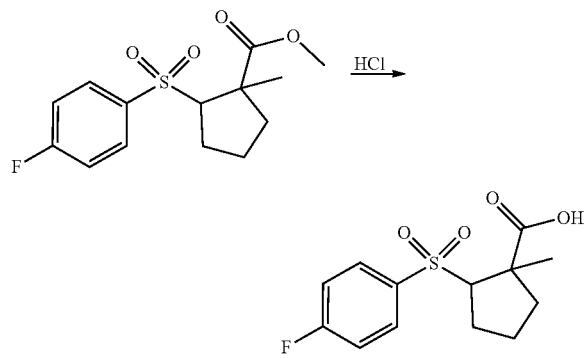

A mixture of methyl 2-[(4-fluorobenzene)sulfonyl]-1-methylcyclopentane-1-carboxylate (300 mg, 1.00 mmol, 1.00 equiv), dioxane (4 mL), and concentrated hydrogen chloride (6 mL) was stirred for 24 h at 60° C. in an oil bath. The reaction mixture was cooled to room temperature. The resulting solution was diluted with water, extracted with ethyl acetate, dried over anhydrous sodium sulfate and concentrated under vacuum. This resulted in the title compound (250 mg, 87%) as brown oil. LC-MS (ESI): [M−H]⁻= 285.1

Example 5, Step 6: Preparation of (1R,2R)—N-((3-chloro-1-(4-(trifluoromethyl)phenyl)-1H-pyrazol-4-yl)methyl)-2-(4-fluorophenylsulfonyl)-1-methylcyclopentanecarboxamide Step 6 proceeded according to the following reaction scheme:

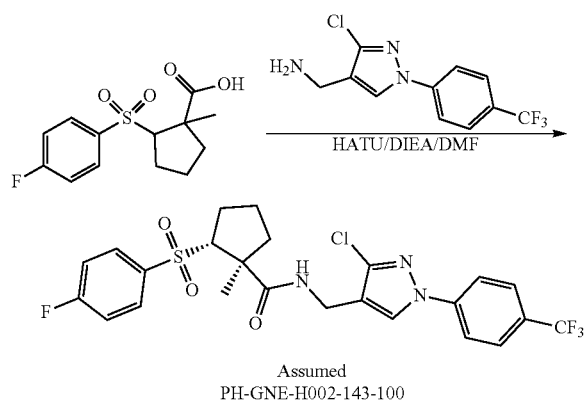

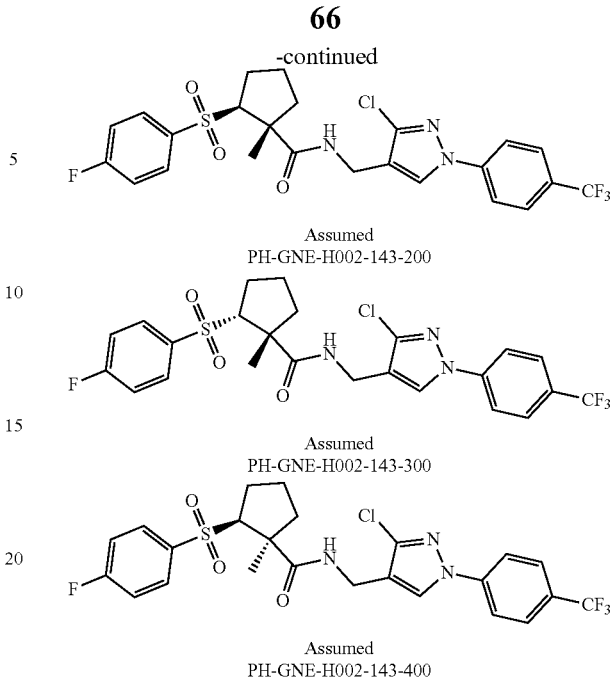

A mixture of [3-chloro-1-[4-(trifluoromethyl)phenyl]-1H-pyrazol-4-yl]methanamine (520 mg, 1.886 mmol, 1.000 equiv), N,N-dimethylformamide (50 mL), DIEA (703 mg, 5.439 mmol, 2.883 equiv), HATU (691 mg, 1.817 mmol, 0.963 equiv), and 2-[(4-fluorobenzene)sulfonyl]-1-methyl-cyclopentane-1-carboxylic acid (1.0 g, 3.493 mmol, 1.851 equiv) was stirred for 12 h at room temperature. The resulting solution was diluted with water, extracted with ethyl acetate, washed with brine, dried over anhydrous sodium sulfate and concentrated under vacuum. The residue was purified by a silica gel column eluting with PE:EA (5:1). The crude product was purified by Chiral-Prep-HPLC with the following conditions (Prep-HPLC-009): Column, Chiralpak IA, 2*25 cm, 5 um; mobile phase, Hex and ethanol (hold 30.0% ethanol in 18 min); Detector, UV 254/220 nm. This resulted in (1S,2R)—N-((3-chloro-1-(4-(trifluoromethyl)phenyl)-1H-pyrazol-4-yl)methyl)-2-(4-fluorophenylsulfonyl)-1-methylcyclopentanecarboxamide (10.6 mg, 1%) as a white solid. $t_R$=2.14 min (CHIRALPAK IB-3, 0.46×5 cm, 3 μm, Hex:EtOH=90:10, 1.0 ml/min). LC-MS (ESI): [M+H]⁺=544.1; ¹H NMR (300 MHz, DMSO-d6) δ 8.54 (s, 1H), 8.21 (m, 1H), 8.00-7.97 (m, 2H), 7.88-7.86 (m, 2H), 7.50-7.45 (m, 2H), 4.33-4.27 (m, 1H), 4.12-4.07 (m, 2H), 2.13-1.56 (m, 6H), 1.46 (s, 3H).

Three more stereoisomers were also isolated from the Chiral-Prep-HPLC resolution.

Isomer 1: (12.7 mg, 1%) as a white solid. $t_R$=4.08 min (CHIRALPAK IB-3, 0.46×5 cm, 3 μm, Hex:EtOH=90:10, 1.0 ml/min). LC-MS (ESI): [M+H]⁺=544.1; ¹H NMR (300 MHz, DMSO-d6) δ 8.54 (s, 1H), 8.21 (m, 1H), 8.00-7.97 (m, 2H), 7.88-7.86 (m, 2H), 7.50-7.44 (m, 2H), 4.33-4.27 (m, 1H), 4.12-4.05 (m, 2H), 2.14-1.52 (m, 6H), 1.46 (s, 3H).

Isomer 2: (86.8 mg, 8%) as a white solid. $t_R$=3.47 min (CHIRALPAK IB-3, 0.46×5 cm, 3 μm, Hex:EtOH=90:10, 1.0 ml/min). LC-MS (ESI): [M+H]⁺=544.1; ¹H NMR (300 MHz, DMSO-d6) δ 8.57 (s, 1H), 8.06-7.86 (m, 7H), 7.49-7.44 (m, 2H), 4.19-3.99 (m, 2H), 3.73-3.70 (m, 1H), 2.22-2.14 (m, 2H), 1.99-1.52 (m, 4H), 1.39 (s, 3H).

Isomer 3: (80.8 mg, 8%) as a white solid. $t_R$=4.84 min (CHIRALPAK IB-3, 0.46×5 cm, 3 μm, Hex:EtOH=90:10, 1.0 ml/min). LC-MS (ESI): [M+H]⁺=544.1; ¹H NMR (300

MHz, DMSO-d6) δ 8.57 (s, 1H), 8.00-7.86 (m, 7H), 7.50-7.44 (m, 2H), 4.19-4.00 (m, 2H), 3.73-3.68 (m, 1H), 2.22-2.14 (m, 2H), 1.99-1.52 (m, 4H), 1.38 (s, 3H).

IC$_{50}$ Determinations of Exemplified Compounds.

IC$_{50}$ values (effective concentration) of compounds on the human and rat TRPA1 channels were determined using a FLIPR Tetra instrument. CHO cells expressing TRPA1 were plated into 384-well plates, incubated overnight at 37 C, and loaded with BD calcium indicator dye for 1 hr at 37° C. followed by 15 minutes. at room temperature. The assay buffer was Hank's Balanced Salt Solution (HBSS) containing 20 mM HEPES (pH readjusted to 7.4) along with 0.02% BSA.

Following dye load and plate cool down, compounds were added to the cells using FLIPR Tetra. Plates were then incubated with compounds for 20 minutes at room temperature prior to adding agonist. Following this incubation, ~EC80 concentration of cinnamaldehyde (75 uM for human TRPA1 and 45 uM for rat TRPA1) was added to active the channels and block of cinnamaldehyde induced calcium influx was measured.

IC$_{50}$ values were fit with a standard Hill function, keeping the Hill coefficient (n) fixed to 1.5. Fixing the Hill coefficient will generally reduce variability of the IC$_{50}$ determination. The IC$_{50}$ values were individually examined to make sure the MIN and MAX points were set correctly prior to validation of the results.

The above compounds of Examples 1-6, together with additional compounds made using the above procedures or purchased via commercial sources, are shown in Table 2 below where: "Ex" denotes example number, "LCMS" denotes measured molecular weight, and the asterisks denote chiral centers.

TABLE 2

| Ex | Structure | Name | LCMS |
|---|---|---|---|
| 1 | 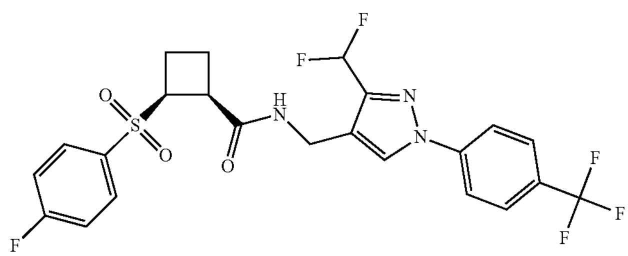 [SMILES: O=C(NCc1cn(-c2ccc(C(F)(F)F)cc2)nc1C(F)F)[C@@H]1CC[C@@H]1S(=O)(=O)c1ccc(F)cc1] | (1S,2S)-N-((3-(difluoromethyl)-1-(4-(trifluoromethyl)phenyl)-1H-pyrazol-4-yl)methyl)-2-(4-fluorophenylsulfonyl)cyclobutanecarboxamide | 532.1 |
| 2 | 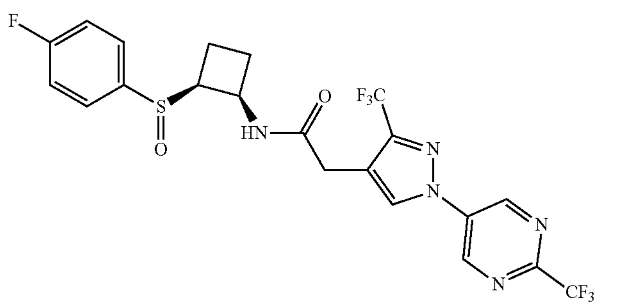 [SMILES: O=C(Cc1cn(-c2cnc(C(F)(F)F)nc2)nc1C(F)(F)F)N[C@@H]1CC[C@@H]1S(=O)c1ccc(F)cc1] | N-((1R,2S)-2-(4-fluorophenylsulfinyl)cyclobutyl)-2-(3-(trifluoromethyl)-1-(2-(trifluoromethyl)pyrimidin-5-yl)-1H-pyrazol-4-yl)acetamide | 536.1 |
| 3 | 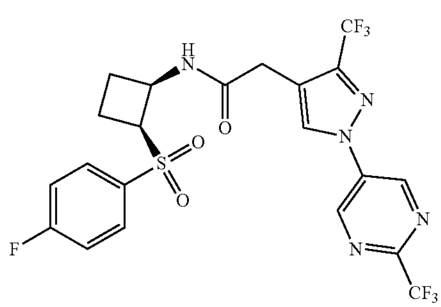 | N-((1R,2S)-2-(4-fluorophenylsulfonyl)cyclobutyl)-2-(3-(trifluoromethyl)-1-(2-(trifluoromethyl)pyrimidin-5-yl)-1H-pyrazol-4-yl)acetamide | 552.1 |
| 4 | 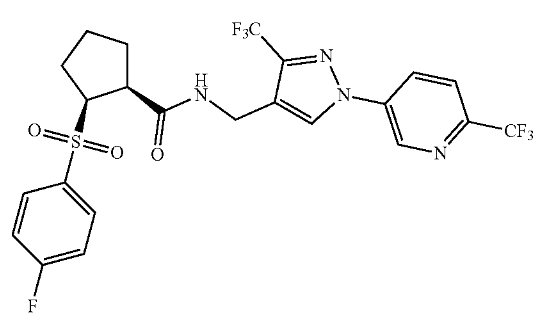 [SMILES: O=C(NCc1cn(-c2ccc(C(F)(F)F)nc2)nc1C(F)(F)F)[C@@H]1CCC[C@@H]1S(=O)(=O)c1ccc(F)cc1] | (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide | 565.1 |

TABLE 2-continued

| Ex | Structure | Name | LCMS |
|---|---|---|---|
| 5 | 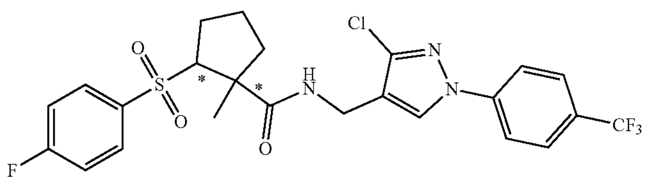 [SMILES: CC1(C(=O)NCc2cn(-c3ccc(C(F)(F)F)cc3)nc2Cl)CCCC1S(=O)(=O)c1ccc(F)cc1] | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 1) | 544.1 |
| 6 | 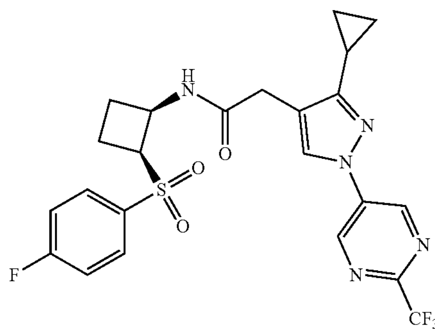 [SMILES: O=C(Cc1cn(-c2cnc(C(F)(F)F)nc2)nc1C1CC1)N[C@@H]1CC[C@@H]1S(=O)(=O)c1ccc(F)cc1] | 2-(3-cyclopropyl-1-(2-(trifluoromethyl)pyrimidin-5-yl)-1H-pyrazol-4-yl)-N-((1R,2S)-2-(4-fluorophenylsulfonyl)cyclobutyl)acetamide | 524.1 |
| 7 | 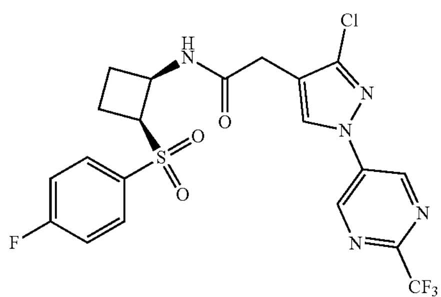 [SMILES: O=C(Cc1cn(-c2cnc(C(F)(F)F)nc2)nc1Cl)N[C@@H]1CC[C@@H]1S(=O)(=O)c1ccc(F)cc1] | 2-(3-chloro-1-(2-(trifluoromethyl)pyrimidin-5-yl)-1H-pyrazol-4-yl)-N-((1R,2S)-2-(4-fluorophenylsulfonyl)cyclobutyl)acetamide | 518.1 |
| 8 | 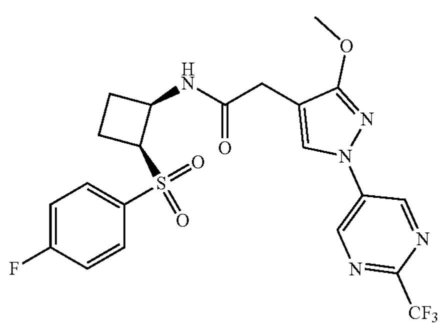 [SMILES: COc1nn(-c2cnc(C(F)(F)F)nc2)cc1CC(=O)N[C@@H]1CC[C@@H]1S(=O)(=O)c1ccc(F)cc1] | N-((1R,2S)-2-(4-fluorophenylsulfonyl)cyclobutyl)-2-(3-methoxy-1-(2-(trifluoromethyl)pyrimidin-5-yl)-1H-pyrazol-4-yl)acetamide | 513.1 |
| 9 | 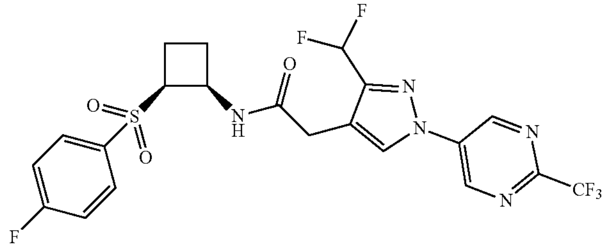 [SMILES: O=C(Cc1cn(-c2cnc(C(F)(F)F)nc2)nc1C(F)F)N[C@@H]1CC[C@@H]1S(=O)(=O)c1ccc(F)cc1] | 2-(3-(difluoromethyl)-1-(2-(trifluoromethyl)pyrimidin-5-yl)-1H-pyrazol-4-yl)-N-((1R,2S)-2-(4-fluorophenylsulfonyl)cyclobutyl)acetamide | NR |

TABLE 2-continued

| Ex | Structure | Name | LCMS |
|---|---|---|---|
| 10 | 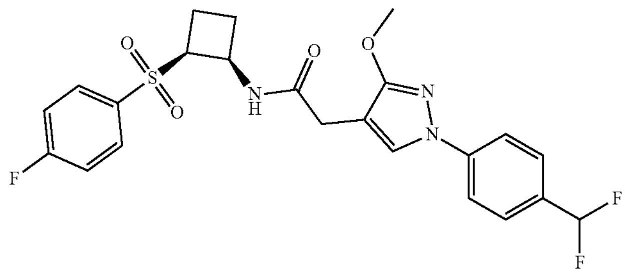 [SMILES: COc1nn(-c2ccc(C(F)F)cc2)cc1CC(=O)N[C@@H]1CC[C@@H]1S(=O)(=O)c1ccc(F)cc1] | 2-(1-(4-(difluoromethyl)phenyl)-3-methoxy-1H-pyrazol-4-yl)-N-((1R,2S)-2-(4-fluorophenylsulfonyl)cyclobutyl)acetamide | 494.1 |
| 11 | 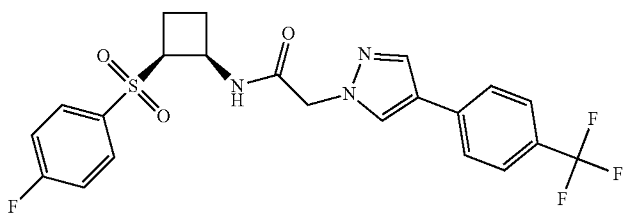 [SMILES: O=C(Cn1cc(-c2ccc(C(F)(F)F)cc2)cn1)N[C@@H]1CC[C@@H]1S(=O)(=O)c1ccc(F)cc1] | N-((1R,2S)-2-((4-fluorophenyl)sulfonyl)cyclobutyl)-2-(4-(4-(trifluoromethyl)phenyl)-1H-pyrazol-1-yl)acetamide | 481.1 |
| 12 | 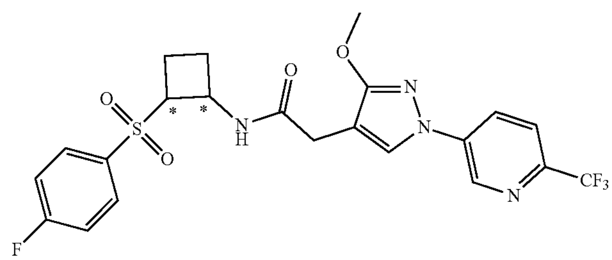 [SMILES: COc1nn(-c2ccc(C(F)(F)F)nc2)cc1CC(=O)NC1CCC1S(=O)(=O)c1ccc(F)cc1] | N-(2-((4-fluorophenyl)sulfonyl)cyclobutyl)-2-(3-methoxy-1-(6-(trifluoromethyl)pyridin-3-yl)-1H-pyrazol-4-yl)acetamide (Enantiomer 2) | 513.1 |
| 13 | 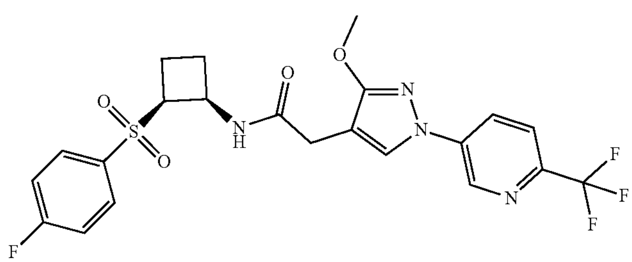 [SMILES: COc1nn(-c2ccc(C(F)(F)F)nc2)cc1CC(=O)N[C@@H]1CC[C@@H]1S(=O)(=O)c1ccc(F)cc1] | N-((1R,2S)-2-((4-fluorophenyl)sulfonyl)cyclobutyl)-2-(3-methoxy-1-(6-(trifluoromethyl)pyridin-3-yl)-1H-pyrazol-4-yl)acetamide | 513.1 |
| 14 | 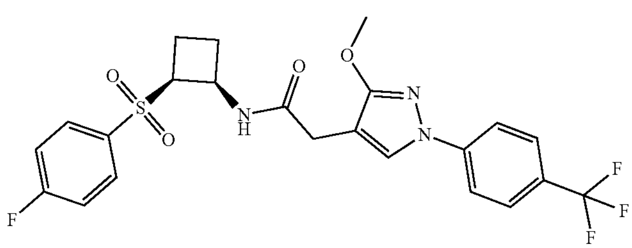 [SMILES: COc1nn(-c2ccc(C(F)(F)F)cc2)cc1CC(=O)N[C@@H]1CC[C@@H]1S(=O)(=O)c1ccc(F)cc1] | N-((1R,2S)-2-((4-fluorophenyl)sulfonyl)cyclobutyl)-2-(3-methoxy-1-(4-(trifluoromethyl)phenyl)-1H-pyrazol-4-yl)acetamide | 512.1 |
| 15 | 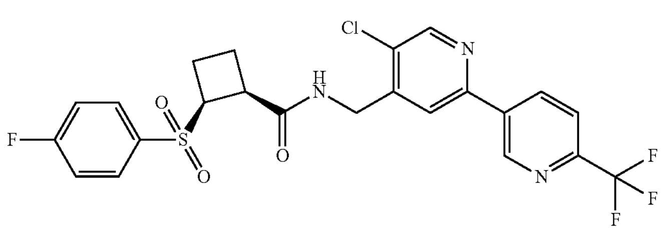 [SMILES: O=C(NCc1cc(-c2ccc(C(F)(F)F)nc2)ncc1Cl)[C@@H]1CC[C@@H]1S(=O)(=O)c1ccc(F)cc1] | (1S,2S)-N-(5-chloro-6'-(trifluoromethyl)-2,3'-bipyridin-4-yl)methyl)-2-(4-fluorophenylsulfonyl)cyclobutanecarboxamide | 528.1 |

TABLE 2-continued

| Ex | Structure | Name | LCMS |
|---|---|---|---|
| 16 | 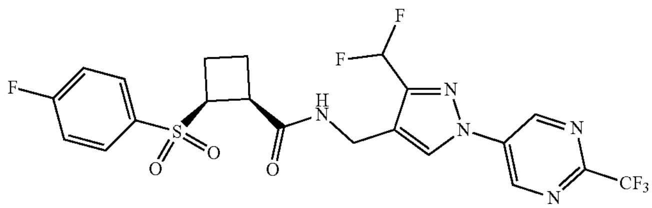 [SMILES: O=C(NCc1cn(-c2cnc(C(F)(F)F)nc2)nc1C(F)F)[C@@H]1CC[C@@H]1S(=O)(=O)c1ccc(F)cc1] | (1S,2S)-N-((3-(difluoromethyl)-1-(2-(trifluoromethyl)pyrimidin-5-yl)-1H-pyrazol-4-yl)methyl)-2-(4-fluorophenylsulfonyl)cyclobutanecarboxamide | 534.1 |
| 17 | 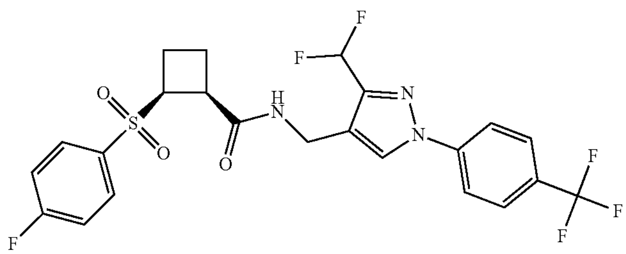 [SMILES: O=C(NCc1cn(-c2ccc(C(F)(F)F)cc2)nc1C(F)F)[C@@H]1CC[C@@H]1S(=O)(=O)c1ccc(F)cc1] | (1S,2S)-N-((3-(difluoromethyl)-1-(4-(trifluoromethyl)phenyl)-1H-pyrazol-4-yl)methyl)-2-(4-fluorophenylsulfonyl)cyclobutanecarboxamide | 532.1 |
| 18 | 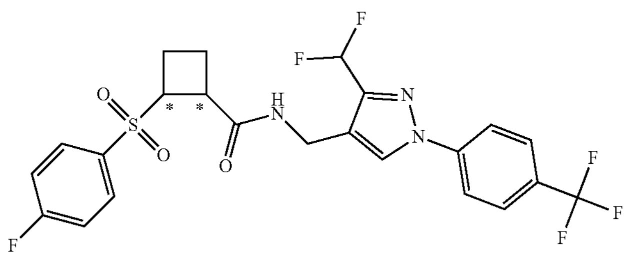 [SMILES: O=C(NCc1cn(-c2ccc(C(F)(F)F)cc2)nc1C(F)F)C1CCC1S(=O)(=O)c1ccc(F)cc1] | N-((3-(difluoromethyl)-1-(4-(trifluoromethyl)phenyl)-1H-pyrazol-4-yl)methyl)-2-(4-fluorophenylsulfonyl)cyclobutanecarboxamide (Enantiomer 2) | 532.1 |
| 19 | 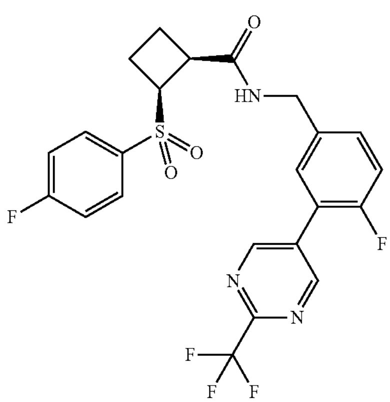 [SMILES: O=C(NCc1ccc(F)c(-c2cnc(C(F)(F)F)nc2)c1)[C@@H]1CC[C@@H]1S(=O)(=O)c1ccc(F)cc1] | (1S,2S)-2-(4-fluorophenyl)sulfonyl-N-[[4-fluoro-3-[2-(trifluoromethyl)pyrimidin-5-yl]phenyl]methyl]cyclobutanecarboxamide | 512.2 |
| 20 | 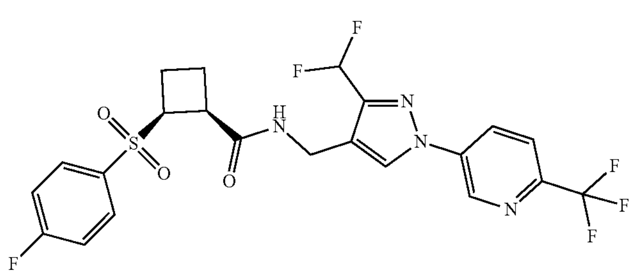 [SMILES: O=C(NCc1cn(-c2ccc(C(F)(F)F)nc2)nc1C(F)F)[C@@H]1CC[C@@H]1S(=O)(=O)c1ccc(F)cc1] | (1S,2S)-N-((3-(difluoromethyl)-1-(6-(trifluoromethyl)pyridin-3-yl)-1H-pyrazol-4-yl)methyl)-2-((4-fluorophenyl)sulfonyl)cyclobutanecarboxamide | 533.1 |

TABLE 2-continued

| Ex | Structure | Name | LCMS |
|---|---|---|---|
| 21 | 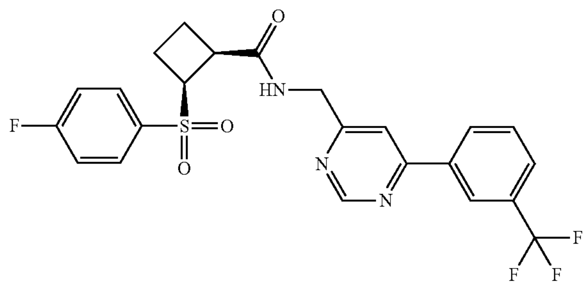 [SMILES: O=C(NCc1cc(-c2cccc(C(F)(F)F)c2)ncn1)[C@@H]1CC[C@@H]1S(=O)(=O)c1ccc(F)cc1] | (1S,2S)-2-((4-fluorophenyl)sulfonyl)-N-((6-(3-(trifluoromethyl)phenyl)pyrimidin-4-yl)methyl)cyclobutanecarboxamide | 494.1 |
| 22 | 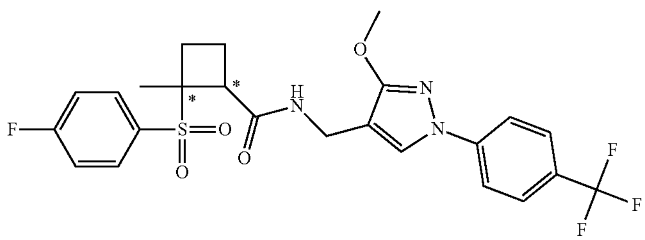 [SMILES: COc1nn(-c2ccc(C(F)(F)F)cc2)cc1CNC(=O)C1CCC1(C)S(=O)(=O)c1ccc(F)cc1] | 2-(4-fluorophenylsulfonyl)-N-(3-methoxy-1-(4-(trifluoromethyl)phenyl)-1H-pyrazol-4-yl)methyl)-2-methylcyclobutanecarboxamide (Enantiomer 1) | 526.1 |
| 23 | 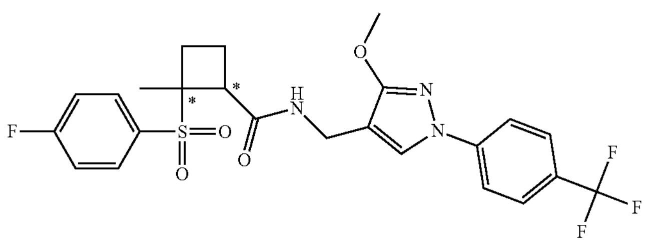 [SMILES: COc1nn(-c2ccc(C(F)(F)F)cc2)cc1CNC(=O)C1CCC1(C)S(=O)(=O)c1ccc(F)cc1] | 2-(4-fluorophenylsulfonyl)-N-((3-methoxy-1-(4-(trifluoromethyl)phenyl)-1H-pyrazol-4-yl)methyl)-2-methylcyclobutanecarboxamide (Enantiomer 2) | 526.1 |
| 24 | 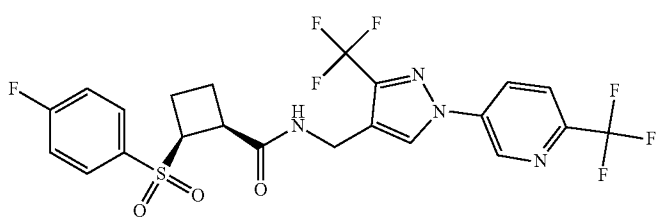 [SMILES: O=C(NCc1cn(-c2ccc(C(F)(F)F)nc2)nc1C(F)(F)F)[C@@H]1CC[C@@H]1S(=O)(=O)c1ccc(F)cc1] | (1S,2S)-2-(4-fluorophenylsulfonyl)-N-((3-(trifluoromethyl)-1-(6-(trifluoromethyl)pyridin-3-yl)-1H-pyrazol-4-yl)methyl)cyclobutanecarboxamide | 551.1 |
| 25 | 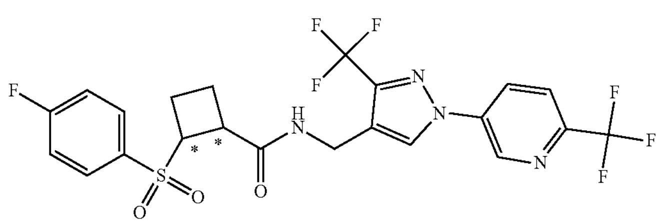 [SMILES: O=C(NCc1cn(-c2ccc(C(F)(F)F)nc2)nc1C(F)(F)F)C1CCC1S(=O)(=O)c1ccc(F)cc1] | 2-(4-fluorophenylsulfonyl)-N-((3-(trifluoromethyl)-1-(6-(trifluoromethyl)pyridin-3-yl)-1H-pyrazol-4-yl)methyl) cyclobutanecarboxamide (Enantiomer 2) | 551.1 |
| 26 | 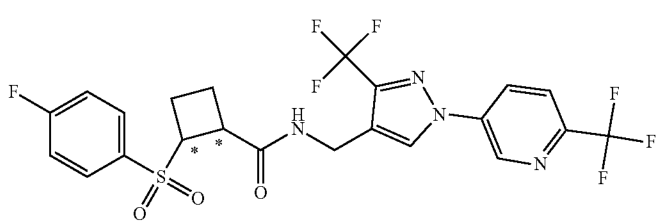 [SMILES: O=C(NCc1cn(-c2ccc(C(F)(F)F)nc2)nc1C(F)(F)F)C1CCC1S(=O)(=O)c1ccc(F)cc1] | 2-(4-fluorophenylsulfonyl)-N-((3-(trifluoromethyl)-1-(6-(trifluoromethyl)pyridin-3-yl)-1H-pyrazol-4-yl)methyl) cyclobutanecarboxamide (Enantiomer 3) | 551.1 |

TABLE 2-continued

| Ex | Structure | Name | LCMS |
|---|---|---|---|
| 27 | 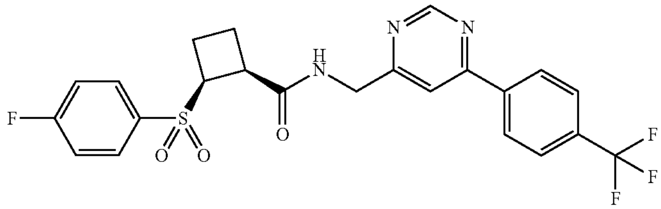 [SMILES: O=C(NCc1cc(-c2ccc(C(F)(F)F)cc2)ncn1)[C@@H]1CC[C@@H]1S(=O)(=O)c1ccc(F)cc1] | (1S,2S)-2-(4-fluorophenylsulfonyl)-N-((6-(4-(trifluoromethyl)phenyl)pyrimidin-4-yl)methyl)cyclobutanecarboxamide | 494.1 |
| 28 | 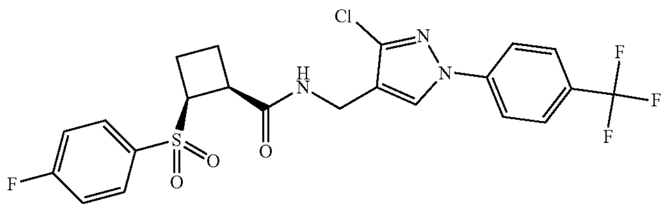 [SMILES: O=C(NCc1cn(-c2ccc(C(F)(F)F)cc2)nc1Cl)[C@@H]1CC[C@@H]1S(=O)(=O)c1ccc(F)cc1] | (1S,2S)-N-((3-chloro-1-(4-(trifluoromethyl)phenyl)-1H-pyrazol-4-yl)methyl)-2-(4-fluorophenylsulfonyl)cyclobutanecarboxamide | 516.1 |
| 29 | 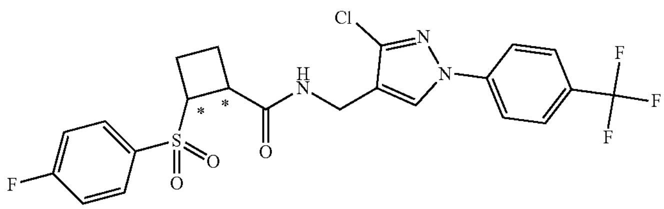 | N-((3-chloro-1-(4-(trifluoromethyl)phenyl)-1H-pyrazol-4-yl)methyl)-2-(4-fluorophenylsulfonyl)cyclobutanecarboxamide (Enantiomer 2) | 516.1 |
| 30 | 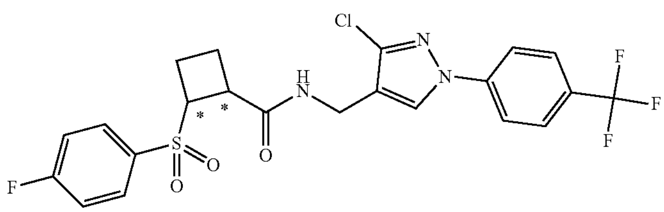 [SMILES: O=C(NCc1cn(-c2ccc(C(F)(F)F)cc2)nc1Cl)C1CCC1S(=O)(=O)c1ccc(F)cc1] | N-((3-chloro-1-(4-(trifluoromethyl)phenyl)-1H-pyrazol-4-yl)methyl)-2-(4-fluorophenylsulfonyl)cyclobutanecarboxamide (Enantiomer 3) | 516.1 |
| 31 | 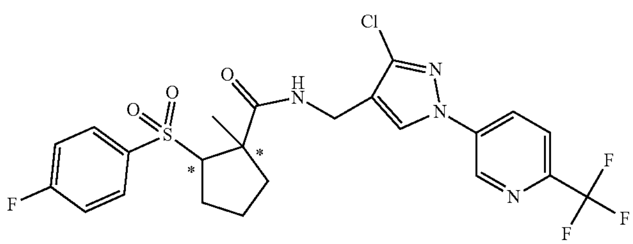 [SMILES: CC1(C(=O)NCc2cn(-c3ccc(C(F)(F)F)nc3)nc2Cl)CCCC1S(=O)(=O)c1ccc(F)cc1] | N-((3-chloro-1-(6-(trifluoromethyl)pyridin-3-yl)-1H-pyrazol-4-yl)methyl)-2-(4-fluorophenylsulfonyl)-1-methylcyclopentanecarboxamide (Enantiomer 1) | 545.1 |
| 32 | 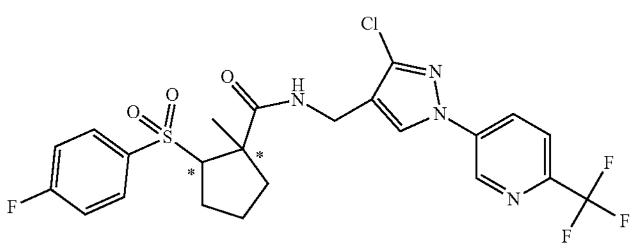 [SMILES: CC1(C(=O)NCc2cn(-c3ccc(C(F)(F)F)nc3)nc2Cl)CCCC1S(=O)(=O)c1ccc(F)cc1] | N-((3-chloro-1-(6-(trifluoromethyl)pyridin-3-yl)-1H-pyrazol-4-yl)methyl)-2-(4-fluorophenylsulfonyl)-1-methylcyclopentanecarboxamide (Enantiomer 2) | 545.1 |
| 33 | 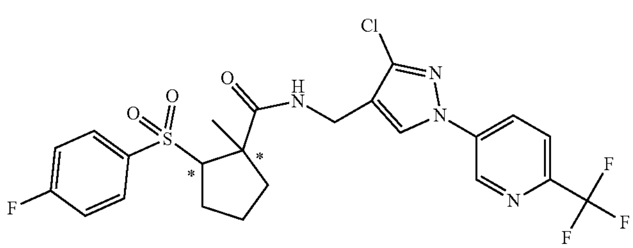 [SMILES: CC1(C(=O)NCc2cn(-c3ccc(C(F)(F)F)nc3)nc2Cl)CCCC1S(=O)(=O)c1ccc(F)cc1] | N-((3-chloro-1-(6-(trifluoromethyl)pyridin-3-yl)-1H-pyrazol-4-yl)methyl)-2-(4-fluorophenylsulfonyl)-1-methylcyclopentanecarboxamide (Enantiomer 3) | 545.1 |

TABLE 2-continued

| Ex | Structure | Name | LCMS |
|---|---|---|---|
| 34 | 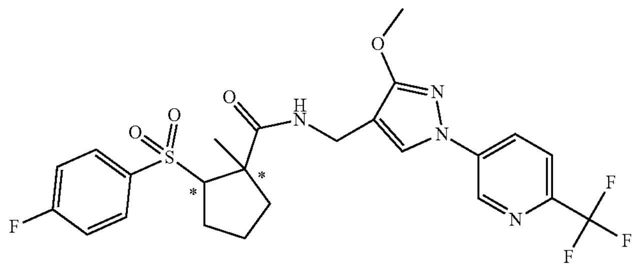 [SMILES: COc1nn(-c2ccc(C(F)(F)F)nc2)cc1CNC(=O)C1(C)CCCC1S(=O)(=O)c1ccc(F)cc1] | 2-(4-fluorophenylsulfonyl)-N-((3-methoxy-1-(6-(trifluoromethyl)pyridin-3-yl)-1H-pyrazol-4-yl)methyl)-1-methylcyclopentanecarboxamide (Enantiomer 1) | 541.2 |
| 35 | 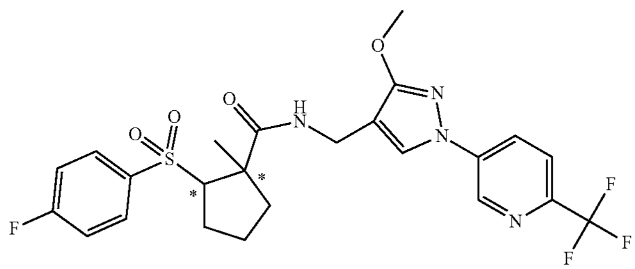 [SMILES: COc1nn(-c2ccc(C(F)(F)F)nc2)cc1CNC(=O)C1(C)CCCC1S(=O)(=O)c1ccc(F)cc1] | 2-(4-fluorophenylsulfonyl)-N-((3-methoxy-1-(6-(trifluoromethyl)pyridin-3-yl)-1H-pyrazol-4-yl)methyl)-1-methylcyclopentanecarboxamide (Enantiomer 2) | 541.2 |
| 36 | 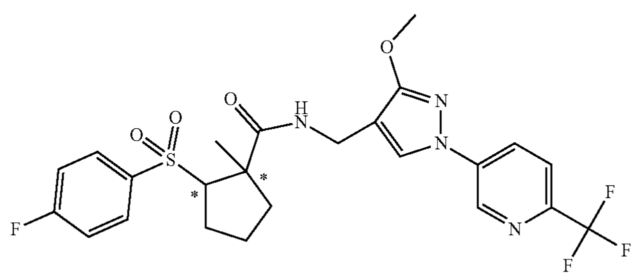 [SMILES: COc1nn(-c2ccc(C(F)(F)F)nc2)cc1CNC(=O)C1(C)CCCC1S(=O)(=O)c1ccc(F)cc1] | 2-(4-fluorophenylsulfonyl)-N-((3-methoxy-1-(6-(trifluoromethyl)pyridin-3-yl)-1H-pyrazol-4-yl)methyl)-1-methylcyclopentanecarboxamide (Enantiomer 3) | 541.2 |
| 37 | 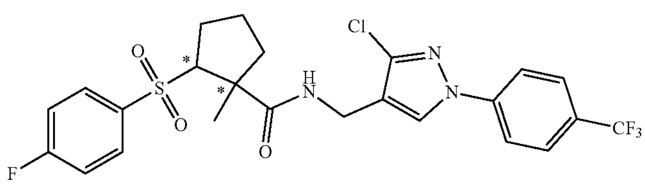 [SMILES: CC1(C(=O)NCc2cn(-c3ccc(C(F)(F)F)cc3)nc2Cl)CCCC1S(=O)(=O)c1ccc(F)cc1] | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 2) | 544.1 |
| 38 | 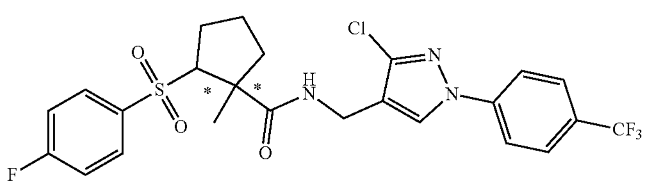 [SMILES: CC1(C(=O)NCc2cn(-c3ccc(C(F)(F)F)cc3)nc2Cl)CCCC1S(=O)(=O)c1ccc(F)cc1] | N-((3-chloro-1-(4-(trifluoromethyl)phenyl)-1H-pyrazol-4-yl)methyl)-2-(4-fluorophenylsulfonyl)-1-methylcyclopentanecarboxamide (Enantiomer 3) | 544.1 |
| 39 | 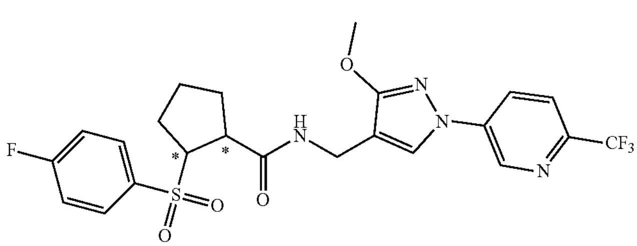 [SMILES: COc1nn(-c2ccc(C(F)(F)F)nc2)cc1CNC(=O)C1CCCC1S(=O)(=O)c1ccc(F)cc1] | 2-(4-fluorophenylsulfonyl)-N-((3-methoxy-1-(6-(trifluoromethyl)pyridin-3-yl)-1H-pyrazol-4-yl)methyl)cyclopentanecarboxamide (Enantiomer 2) | 527 |

TABLE 2-continued

| Ex | Structure | Name | LCMS |
|---|---|---|---|
| 40 | 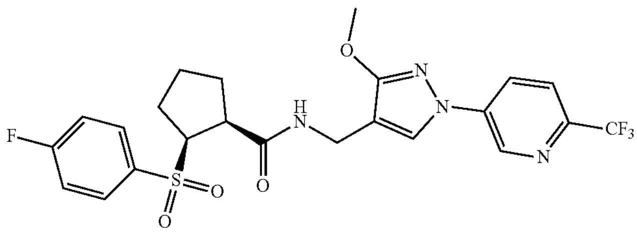 [SMILES: COc1nn(-c2ccc(C(F)(F)F)nc2)cc1CNC(=O)[C@@H]1CCC[C@@H]1S(=O)(=O)c1ccc(F)cc1] | (1S,2S)-2-(4-fluorophenylsulfonyl)-N-((3-methoxy-1-(6-(trifluoromethyl)pyridin-3-yl)-1H-pyrazol-4-yl)methyl)cyclopentanecarboxamide | 527 |
| 41 | 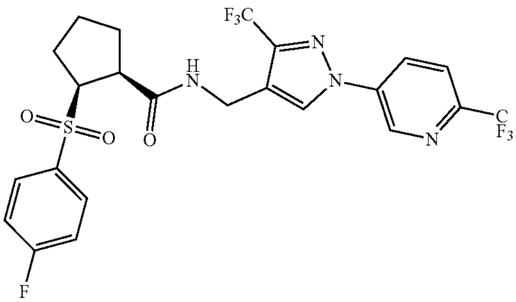 [SMILES: O=C(NCc1cn(-c2ccc(C(F)(F)F)nc2)nc1C(F)(F)F)[C@@H]1CCC[C@@H]1S(=O)(=O)c1ccc(F)cc1] | (1S,2S)-2-[(4-fluorobenzene)sulfonyl]-N-[[3-(trifluoromethyl)-1-[6-(trifluoromethyl)pyridin-3-yl]-1H-pyrazol-4-yl]methyl]cyclopentane-1-carboxamide | 565.1 |
| 42 | 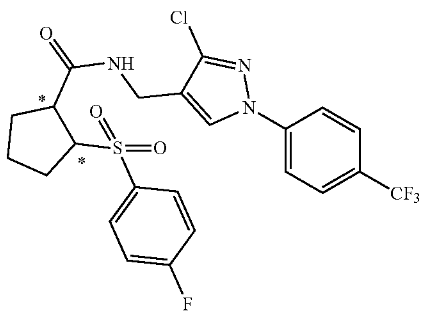 [SMILES: O=C(NCc1cn(-c2ccc(C(F)(F)F)cc2)nc1Cl)C1CCCC1S(=O)(=O)c1ccc(F)cc1] | N-((3-chloro-1-(4-(trifluoromethyl)phenyl)-1H-pyrazol-4-yl)methyl)-2-(4-fluorophenylsulfonyl)cyclopentanecarboxamide (Enantiomer 2) | 530.1 |
| 43 | 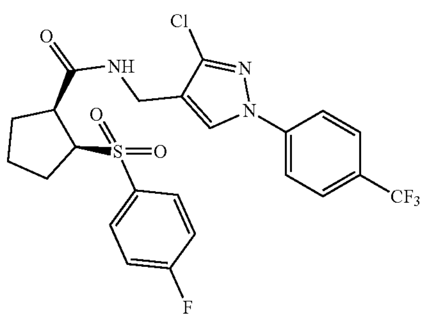 [SMILES: O=C(NCc1cn(-c2ccc(C(F)(F)F)cc2)nc1Cl)[C@@H]1CCC[C@@H]1S(=O)(=O)c1ccc(F)cc1] | (1S,2S)-N-((3-chloro-1-(4-(trifluoromethyl)phenyl)-1H-pyrazol-4-yl)methyl)-2-(4-fluorophenylsulfonyl)cyclopentanecarboxamide | 530.1 |

The $IC_{50}$ and proton $^1H$ NMR results for the compounds detailed in Table 2 are reported in Table 3 below where "$IC_{50}$" denotes hTRPA1 CHO Ca2+AUC EVO ($IC_{50}$) in micromolar units and the asterisks denote chiral centers.

TABLE 3

| Ex | Structure | $IC_{50}$ | $^1H$ NMR |
|---|---|---|---|
| 1 | 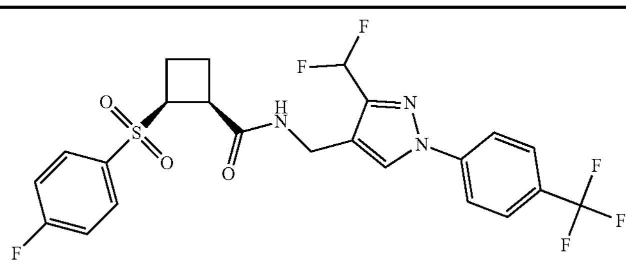 | 0.0346 | $^1H$ NMR (400 MHz, CDCl$_3$) δ 8.12 (s, 1H), 7.9-7.83 (m, 4H), 7.75 (d, J = 8.4 Hz, 2H), 7.24 (t, J = 8.4 Hz, 2H), 6.98-6.71 (m, 2H), 4.58 (dd, J = 15, 6 Hz, 1H), 4.43 (dd, J = 15, 5.6 Hz, 1H), 4.00-3.95 (m, 1H), 3.64-3.57 (m, 1H), 2.45-2.3 (m, 2H), 2.23-2.16 (m, 1H), 2.01-1.97 (m, 1H). |

TABLE 3-continued
| Ex | Structure | IC$_{50}$ | $^1$H NMR |
|---|---|---|---|
| 2 | 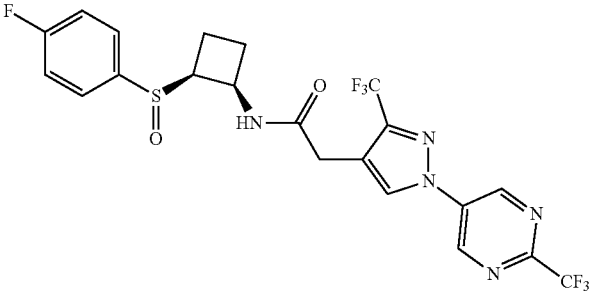 [SMILES: O=C(Cc1cn(-c2cnc(C(F)(F)F)nc2)nc1C(F)(F)F)N[C@@H]1CC[C@@H]1S(=O)c1ccc(F)cc1] | 0.50 | $^1$H NMR (300 MHz, CDCl$_3$) δ 9.32 (s, 2H), 8.34 (s, 1H), 7.64-7.58 (m, 2H), 7.54-7.48 (m, 1H), 7.28-7.16 (m, 2H), 5.01-4.94 (m, 1H), 3.75-3.67 (m, 2H), 3.55-3.38 (m, 2H), 2.53 (m, 1H), 2.46-2.29 (m, 3H). |
| 3 | 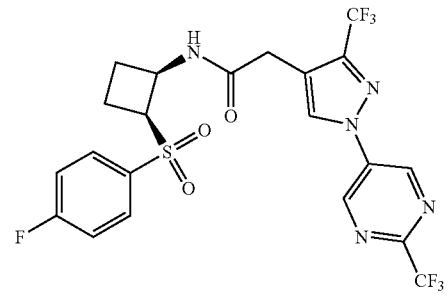 | 0.00788 | $^1$H NMR (400 MHz, CDCl$_3$) δ 9.35 (s, 2H), 8.52 (s, 1H), 7.91-7.88 (m, 2H), 7.29-7.25 (m, 2H), 6.69 (d, J = 8.8 Hz, 1H), 5.22-5.13 (m, 1H), 4.06-4.04 (m, 1H), 3.71-3.62 (m, 2H), 2.61-2.48 (m, 2H), 2.11-207 (m, 2H). |
| 4 | 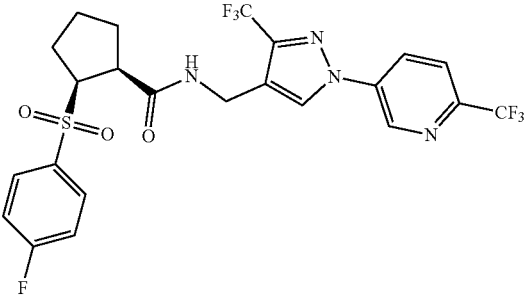 [SMILES: O=C(NCc1cn(-c2ccc(C(F)(F)F)nc2)nc1C(F)(F)F)[C@@H]1CCC[C@@H]1S(=O)(=O)c1ccc(F)cc1] | 0.0218 | $^1$H NMR (300 MHz, DMSO-d6) δ 9.24 (s, 1H), 8.80 (s, 1H), 8.52-8.42 (m, 2H), 8.14-8.11 (m, 1H), 7.94-7.90 (m, 2H), 7.50-7.45 (m, 2H), 4.27-3.97 (m, 3H), 3.08-3.02 (m, 1H), 2.28-2.22 (m, 1H), 1.93-1.77 (m, 4H), 1.64-1.50 (m, 1H). |
| 5 | 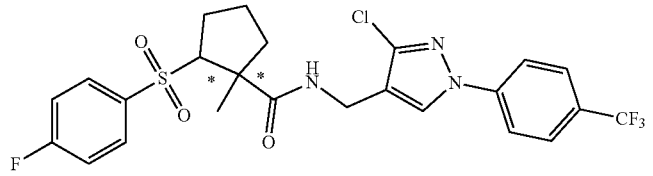 [SMILES: CC1(C(=O)NCc2cn(-c3ccc(C(F)(F)F)cc3)nc2Cl)CCCC1S(=O)(=O)c1ccc(F)cc1] | 0.00879 | $^1$H NMR (300 MHz, DMSO-d6) δ 8.57 (s, 1H), 8.06-7.86 (m, 7H), 7.49-7.44 (m, 2H), 4.19-3.99 (m, 2H), 3.73-3.70 (m, 1H), 2.22-2.14 (m, 2H), 1.99-1.52 (m, 4H), 1.39 (s, 3H). |
| 6 | 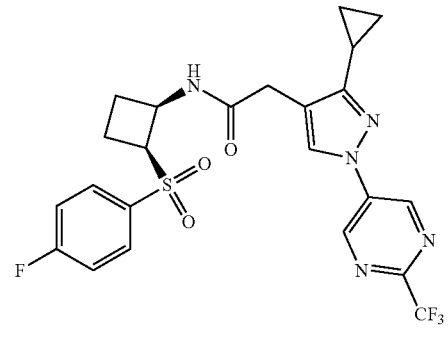 [SMILES: O=C(Cc1cn(-c2cnc(C(F)(F)F)nc2)nc1C1CC1)N[C@@H]1CC[C@@H]1S(=O)(=O)c1ccc(F)cc1] | 0.0469 | $^1$H NMR (300 MHz, DMSO-d6) δ 9.46 (s, 2H), 8.50-8.46 (s, 2H), 7.98-7.94 (m, 2H), 7.48-7.42 (m, 2H), 6.53-6.36 (m, 2H), 4.73-4.67 (m, 1H), 4.29 (s, 1H), 3.46 (d, J = 15 Hz, 1H), 3.19 (d, J = 18 Hz, 1H), 2.49 (s, 1H), 2.27-2.22 (m, 3H), 1.88 (d, J = 6 Hz, 3H). |

TABLE 3-continued

| Ex | Structure | IC$_{50}$ | $^1$H NMR |
|---|---|---|---|
| 7 | 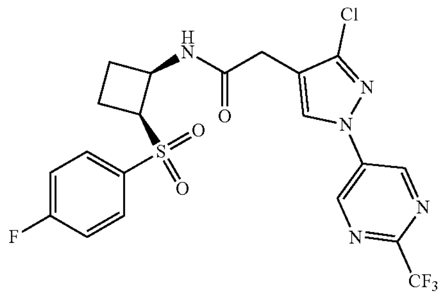 [SMILES: O=C(Cc1cn(-c2cnc(C(F)(F)F)nc2)nc1Cl)N[C@@H]1CC[C@@H]1S(=O)(=O)c1ccc(F)cc1] | 0.0403 | $^1$H NMR (300 MHz, DMSO-d6) δ 9.46 (s, 2H), 8.61 (s, 1H), 8.53 (d, J = 8.1 Hz, 1H), 7.97-7.93 (m, 2H), 7.46-7.40 (m, 2H), 4.70 (m, 1H), 4.29 (m, 1H), 3.43-3.38 (m, 1H), 3.19-3.13 (m, 1H), 2.49 (m, 1H), 2.27-2.21 (m, 3H). |
| 8 | 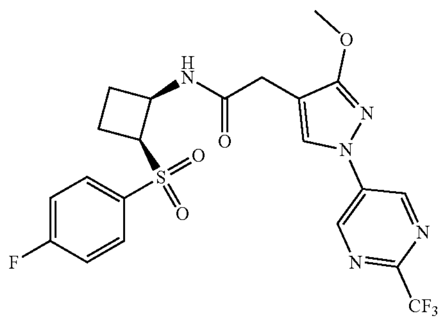 [SMILES: COc1nn(-c2cnc(C(F)(F)F)nc2)cc1CC(=O)N[C@@H]1CC[C@@H]1S(=O)(=O)c1ccc(F)cc1] | 0.246 | $^1$H NMR (300 MHz, CDCl$_3$) δ 8.65-8.64 (s, 1H), 8.11 (s, 1H), 7.95 (s, 1H), 7.89-7.84 (m, 2H), 7.66-7.61 (s, 1H), 7.22-7.16 (m, 2H), 6.84 (d, J = 9 Hz, 1H), 5.14-5.08 (m, 1H), 4.08 (s, 3H), 4.01 (s, 1H), 3.39 (s, 2H), 2.54-2.41 (m, 2H), 2.18-2.02 (m, 2H) |
| 9 | 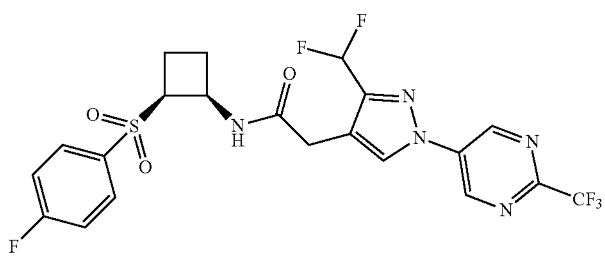 [SMILES: O=C(Cc1cn(-c2cnc(C(F)(F)F)nc2)nc1C(F)F)N[C@@H]1CC[C@@H]1S(=O)(=O)c1ccc(F)cc1] | 0.0352 | $^1$HNMR (300 MHz, CDCl$_3$) δ 9.29 (s, 2H), 8.42 (s, 1H), 7.89-7.85 (s, 2H), 7.26-7.21 (m, 2H), 7.02-6.66 (m, 2H), 5.17-5.11 (s, 1H), 4.04-4.02 (s, 1H), 3.70 (s, 2H), 2.60-2.44 (m, 2H), 2.11-2.03 (m, 2H). |
| 10 | 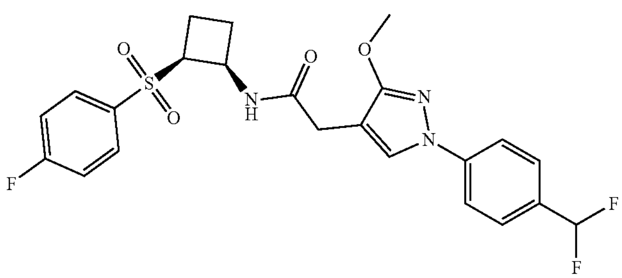 [SMILES: COc1nn(-c2ccc(C(F)F)cc2)cc1CC(=O)N[C@@H]1CC[C@@H]1S(=O)(=O)c1ccc(F)cc1] | 0.0436 | $^1$H NMR (400 MHz, DMSO-d6) δ 8.33 (d, J = 8.1 Hz, 1H), 8.15 (s, 1H), 7.96-7.92 (m, 2H), 7.80 (d, J = 8.4 Hz, 2H), 7.65 (d, J = 8.4 Hz, 2H), 7.45-7.40 (m, 2H), 7.05 (t, J = 60.0 Hz, 1H), 4.72-4.66 (m, 1H), 4.30-4.20 (m, 1H), 3.92 (s, 3H), 3.21-3.17 (m, 1H), 3.07-3.02 (m, 1H), 2.51-2.40 (m, 1H), 2.30-2.10 (m, 3H). |
| 11 | 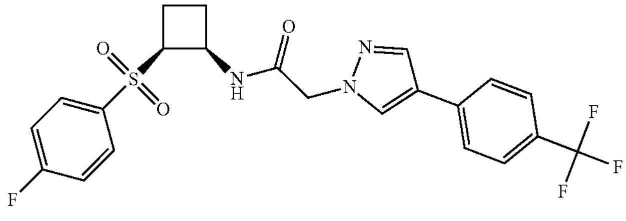 [SMILES: O=C(Cn1cc(-c2ccc(C(F)(F)F)cc2)cn1)N[C@@H]1CC[C@@H]1S(=O)(=O)c1ccc(F)cc1] | 0.20 | $^1$HNMR (300 MHz, CDCl$_3$) δ 7.89-7.81 (m, 3H), 7.70-7.52 (m, 5H), 7.17-7.13 (m, 2H), 6.86 (s, 1H), 4.76-4.46 (m, 3H), 4.00-3.94 (m, 1H), 2.36-2.06 (m, 4H) |

TABLE 3-continued

| Ex | Structure | IC$_{50}$ | $^1$H NMR |
|---|---|---|---|
| 12 | 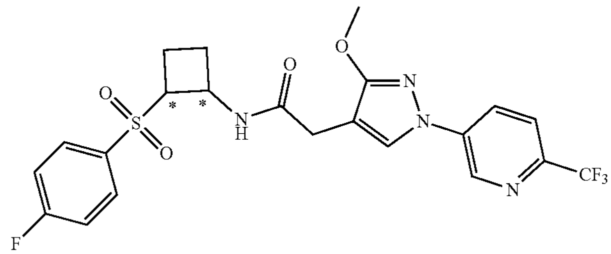 [SMILES: COc1nn(-c2ccc(C(F)(F)F)nc2)cc1CC(=O)NC1CCC1S(=O)(=O)c1ccc(F)cc1] | 0.213 | $^1$HNMR (300 MHz, CDCl$_3$) δ 9.00 (s, 1H), 8.10 (m, 1H), 8.07 (s, 1H), 7.99-7.84 (m, 2H), 7.71 (m, 1H), 7.26-7.18 (m, 2H), 6.91-6.85 (m, 1H), 5.14-5.05 (m, 1H), 4.07 (s, 3H), 4.07 (m, 1H), 3.39 (s, 2H), 2.53-2.03 (m, 4H). |
| 13 | 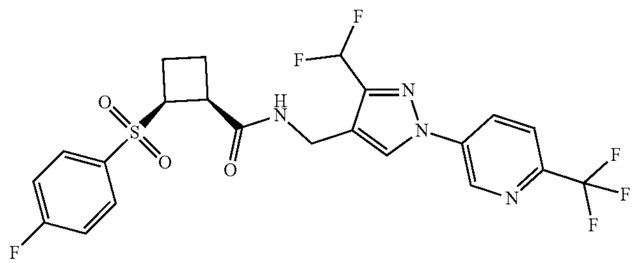 [SMILES: O=C(NCc1cn(-c2ccc(C(F)(F)F)nc2)nc1C(F)F)[C@@H]1CC[C@@H]1S(=O)(=O)c1ccc(F)cc1] | 0.0185 | $^1$HNMR (300 MHz, CDCl$_3$) δ 9.00 (s, 1H), 8.10 (m, 1H), 8.07 (s, 1H), 7.99-7.84 (m, 2H), 7.71 (m, 1H), 7.26-7.18 (m, 2H), 6.91-6.85 (m, 1H), 5.14-5.05 (m, 1H), 4.07 (s, 3H), 4.07 (m, 1H), 3.39 (s, 2H), 2.53-2.03 (m, 4H). |
| 14 | 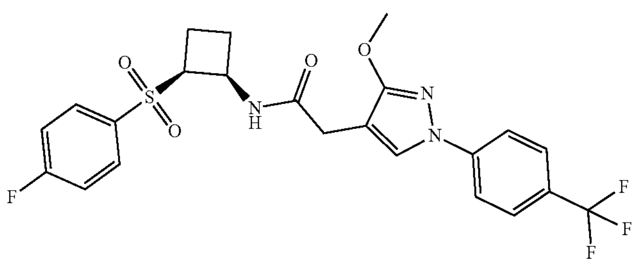 [SMILES: COc1nn(-c2ccc(C(F)(F)F)cc2)cc1CC(=O)N[C@@H]1CC[C@@H]1S(=O)(=O)c1ccc(F)cc1] | 0.0052 | $^1$H NMR (300 MHz, DMSO-d6) δ 8.07 (s, 1H), 7.92-7.26 (m, 8H), 4.84-4.76 (m, 1H), 4.18 (m, 1H), 3.99 (s, 3H), 3.33-3.21 (m, 2H), 2.60-2.13 (m, 4H) |
| 15 | 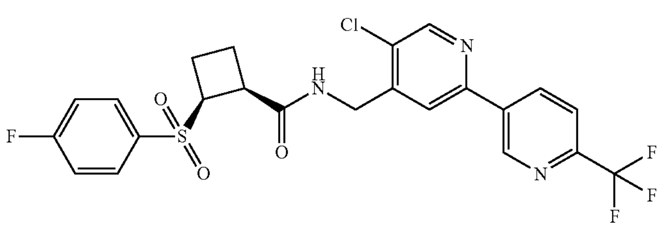 [SMILES: O=C(NCc1cc(-c2ccc(C(F)(F)F)nc2)ncc1Cl)[C@@H]1CC[C@@H]1S(=O)(=O)c1ccc(F)cc1] | 0.14 | $^1$H NMR (300 MHz, CDCl$_3$) δ 9.37 (s, 1H), 8.67 (s, 1H), 8.57 (d, J = 7.8 Hz, 1H), 7.90-7.86 (m, 3H), 7.78 (d, J = 7.5 Hz, 1H), 7.26-7.23 (m, 2H), 6.97-6.89 (m, 1H), 4.80 (d, J = 15 Hz, 1H), 4.47 (d, J = 16.8 Hz, 1H), 3.94 (br, 1H), 3.76-3.71 (s, 1H), 2.43 (s, 2H), 2.18-2.10 (s, 1H), 2.05-1.97 (s, 1H) |
| 16 | 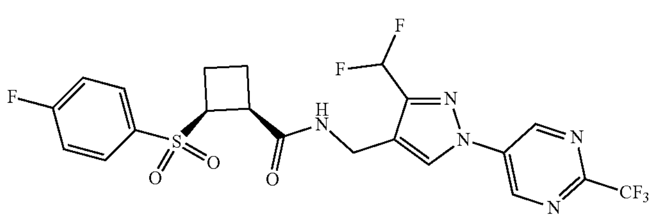 [SMILES: O=C(NCc1cn(-c2cnc(C(F)(F)F)nc2)nc1C(F)F)[C@@H]1CC[C@@H]1S(=O)(=O)c1ccc(F)cc1] | 0.162 | $^1$H NMR (400 MHz, CDCl$_3$) δ 9.30 (s, 2H), 8.66 (s, 1H), 7.89-7.88 (m, 2H), 7.28 (s, 1H), 7.26-7.24 (m, 1H), 6.94-6.65 (m, 2H), 4.89-4.83 (m, 1H), 4.46-4.40 (m, 1H), 4.08-4.02 (m, 1H), 3.62-3.56 (m, 1H), 2.76-2.69 (m, 1H), 2.55-2.46 (m, 1H), 2.20-2.07 (m, 2H). |
| 17 | 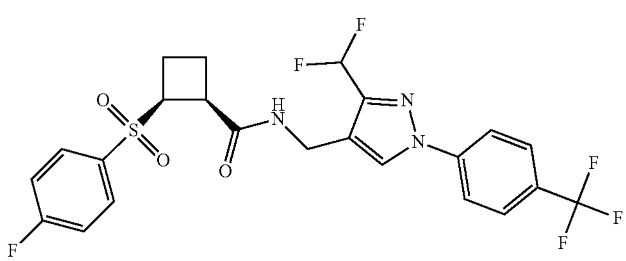 [SMILES: O=C(NCc1cn(-c2ccc(C(F)(F)F)cc2)nc1C(F)F)[C@@H]1CC[C@@H]1S(=O)(=O)c1ccc(F)cc1] | 0.0242 | $^1$H NMR (400 MHz, CDCl$_3$) δ 8.42 (s, 1H), 7.91-7.84 (m, 4H), 7.70 (d, J = 8.4 Hz, 2H), 7.26 (d, J = 6.8 Hz, 2H), 6.84 (t, J = 54 Hz, 1H), 6.60 (t, J = 5.6 Hz, 1H), 4.73 (dd, J = 15.6, 6.4 Hz, 1H), 4.56 (dd, J = 15.6, 5.2 Hz, 1H), 4.11-4.05 (m, 1H), 3.59-3.55 (m, 1H), 2.73-2.52 (m, 2H), 2.19-2.12 (m, 2H). |

TABLE 3-continued

| Ex | Structure | IC$_{50}$ | $^1$H NMR |
|---|---|---|---|
| 18 | 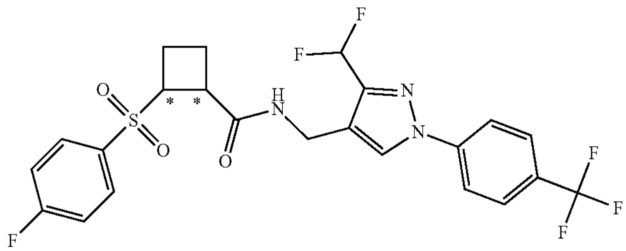 [SMILES: O=C(NCc1cn(-c2ccc(C(F)(F)F)cc2)nc1C(F)F)C1CCC1S(=O)(=O)c1ccc(F)cc1] | 0.096 | $^1$H NMR (400 MHz, CDCl$_3$) δ 8.42 (s, 1H), 7.91-7.84 (m, 4H), 7.70 (d, J = 8.4 Hz, 2H), 7.25 (d, J = 8.4 Hz, 2H), 6.99 (t, J = 54.4 Hz, 1H), 6.60 (s, 1H), 4.73 (dd, J = 16, 6.8 Hz, 1H), 4.56 (dd, J = 15.6, 5.2 Hz, 1H), 4.11-4.05 (m, 1H), 3.61-3.55 (m, 1H), 2.74-2.51 (m, 2H), 2.2-2.1 (m, 2H). |
| 19 | 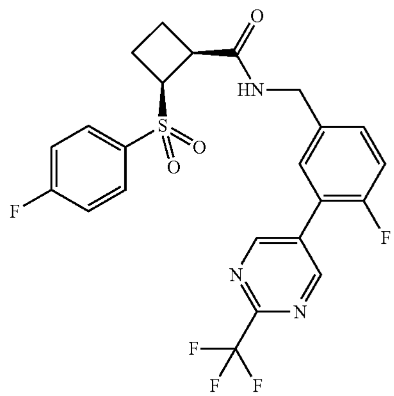 [SMILES: O=C(NCc1ccc(F)c(-c2cnc(C(F)(F)F)nc2)c1)[C@@H]1CC[C@@H]1S(=O)(=O)c1ccc(F)cc1] | 0.159 | 1H NMR (400 MHz, DMSO) δ 9.31-9.25 (d, J = 1.3 Hz, 2H), 8.52-8.47 (t, J = 5.9 Hz, 1H), 7.95-7.88 (m, 2H), 7.62-7.56 (dd, J = 7.4, 2.2 Hz, 1H), 7.45-7.35 (m, 3H), 7.34-7.27 (m, 1H), 4.35-4.27 (m, 1H), 4.25-4.14 (m, 2H), 3.52-3.42 (m, 1H), 2.35-2.24 (m, 1H), 2.15-1.98 (m, 3H) |
| 20 | 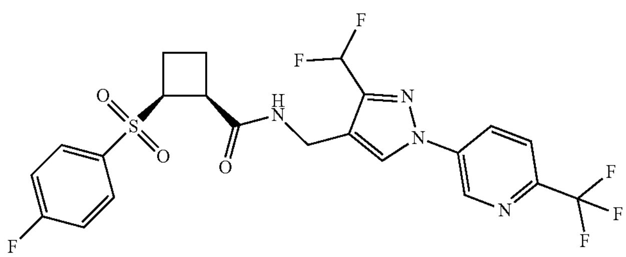 [SMILES: O=C(NCc1cn(-c2ccc(C(F)(F)F)nc2)nc1C(F)F)[C@@H]1CC[C@@H]1S(=O)(=O)c1ccc(F)cc1] | 0.0984 | $^1$HNMR (300 MHz, CDCl$_3$) δ 9.11 (s, 1H), 8.54 (s, 1H), 8.23 (d, J = 6 Hz, 1H), 7.90-7.85 (m, 2H), 7.75 (d, J = 9 Hz, 1H), 7.28-7.23 (m, 2H), 6.96 (t, J = 54 Hz, 1H), 6.61 (br, 1H), 4.84-4.77 (m, 1H), 4.51-4.44 (m, 1H), 4.09-4.04 (m, 1H), 3.62-3.54 (m, 1H), 2.72-2.64 (m, 1H), 2.55-2.45 (m, 1H), 2.21-2.08 (m, 2H) |
| 21 | 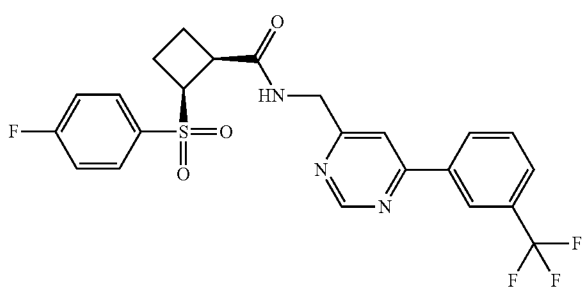 [SMILES: O=C(NCc1cc(-c2cccc(C(F)(F)F)c2)ncn1)[C@@H]1CC[C@@H]1S(=O)(=O)c1ccc(F)cc1] | 0.386 | $^1$HNMR (400 MHz, CDCl$_3$) δ 9.20 (s, 1H), 8.42 (s, 1H), 8.32 (d, J = 8 Hz, 1H), 7.92-7.89 (m, 2H), 7.89 (d, J = 7.2 Hz, 1H), 7.66 (t, J = 7.8 Hz, 1H), 7.26-7.20 (m, 3H), 4.77 (d, J = 17.6 Hz, 1H), 4.68 (d, J = 50.4 Hz, 2H), 4.14-4.07 (m, 1H), 3.75-3.67 (m, 1H), 2.49-2.34 (m, 2H), 2.32-2.19 (m, 1H), 2.06-1.99 (m, 1H) |
| 22 | 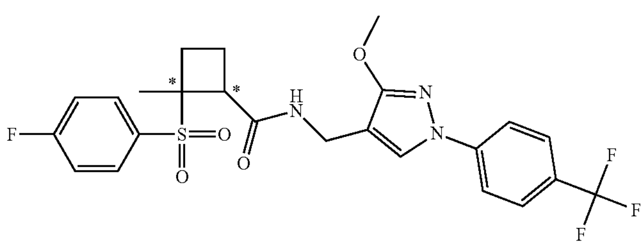 [SMILES: COc1nn(-c2ccc(C(F)(F)F)cc2)cc1CNC(=O)C1CCC1(C)S(=O)(=O)c1ccc(F)cc1] | 0.0717 | $^1$HNMR (300 MHz, CDCl$_3$) δ 8.04 (s, 1H), 7.89-7.85 (m, 2H), 7.70-7.58 (m, 4H), 7.26-7.19 (m, 2H), 6.37 (s, 1H), 4.37-4.35 (m, 2H), 4.02 (s, 3H), 3.26-3.20 (m, 1H), 2.76-2.61 (m, 2H), 2.17-2.12 (m, 1H), 1.90-1.82 (m, 1H), 1.60 (s, 3H). |

TABLE 3-continued

| Ex | Structure | IC$_{50}$ | $^1$H NMR |
|---|---|---|---|
| 23 | 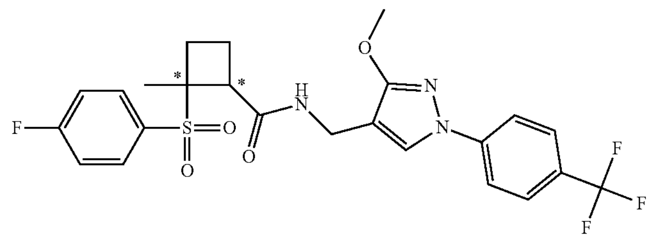 [SMILES: COc1nn(-c2ccc(C(F)(F)F)cc2)cc1CNC(=O)C1CCC1(C)S(=O)(=O)c1ccc(F)cc1] | 0.038 | $^1$HNMR (300 MHz, CDCl$_3$) δ 8.04 (s, 1H), 7.89-7.85 (m, 2H), 7.70-7.58 (m, 4H), 7.26-7.19 (m, 2H), 6.38 (s, 1H), 4.37-4.35 (m, 2H), 4.02 (s, 3H), 3.26-3.20 (m, 1H), 2.73-2.61 (m, 2H), 2.15-2.12 (m, 1H), 1.90-1.84 (m, 1H), 1.59 (s, 3H). |
| 24 | 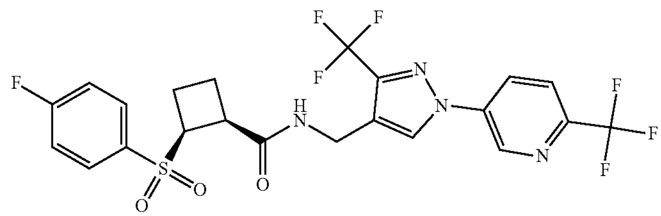 [SMILES: O=C(NCc1cn(-c2ccc(C(F)(F)F)nc2)nc1C(F)(F)F)[C@@H]1CC[C@@H]1S(=O)(=O)c1ccc(F)cc1] | 0.0415 | $^1$H NMR (300 MHz, DMSO-d6) δ 9.24 (s, 1H), 8.80 (s, 1H), 8.51-8.47 (m, 1H), 8.36-8.32 (m, 1H), 8.13 (d, J = 9 Hz, 1H), 7.91-7.87 (m, 2H), 7.50-7.44 (m, 2H), 4.40-4.20 (m, 3H), 3.51-3.49 (m, 1H), 2.41-2.35 (m, 2H), 2.16-2.15 (m, 1H), 1.97-1.96 (m, 1H). |
| 25 | 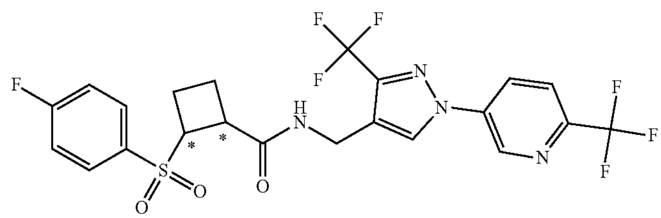 [SMILES: O=C(NCc1cn(-c2ccc(C(F)(F)F)nc2)nc1C(F)(F)F)C1CCC1S(=O)(=O)c1ccc(F)cc1] | 0.192 | $^1$H NMR (300 MHz, DMSO-d6) δ 9.24 (s, 1H), 8.80 (s, 1H), 8.51-8.47 (m, 1H), 8.36-8.32 (m, 1H), 8.13 (d, J = 9 Hz, 1H), 7.91-7.86 (m, 2H), 7.50-7.44 (m, 2H), 4.43-4.14 (m, 3H), 3.51-3.46 (m, 1H), 2.42-2.37 (m, 2H), 2.16-2.14 (m, 1H), 1.98-1.96 (m, 1H). |
| 26 | 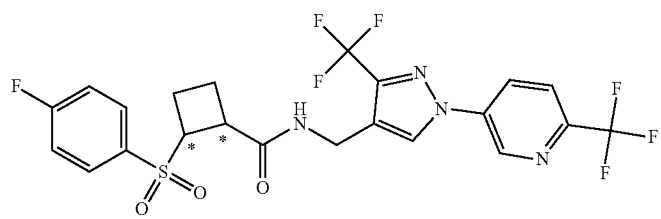 [SMILES: O=C(NCc1cn(-c2ccc(C(F)(F)F)nc2)nc1C(F)(F)F)C1CCC1S(=O)(=O)c1ccc(F)cc1] | 0.0902 | $^1$H NMR (300 MHz, DMSO-d6) δ 9.29 (s, 1H), 8.71 (s, 1H), 8.55-8.52 (m, 1H), 8.47-8.43 (m, 1H), 8.14 (d, J = 9 Hz, 1H), 7.94-7.88 (m, 2H), 7.43-7.36 (m, 2H), 4.23-4.18 (m, 3H), 3.49-3.40 (m, 1H), 2.31-2.23 (m, 1H), 2.15-2.02 (m, 3H). |
| 27 | 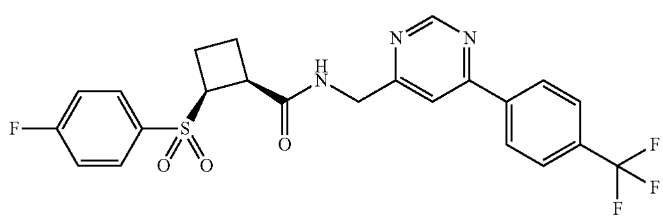 [SMILES: O=C(NCc1cc(-c2ccc(C(F)(F)F)cc2)ncn1)[C@@H]1CC[C@@H]1S(=O)(=O)c1ccc(F)cc1] | 0.113 | $^1$H NMR (400 MHz, DMSO-d6) δ 9.23 (s, 1H), 8.72-8.68 (m, 1H), 8.40-8.37 (m, 2H), 7.95-7.90 (m, 5H), 7.43-7.37 (m, 2H), 4.46-4.21 (m, 3H), 3.63-3.54 (m, 1H), 2.32-2.20 (m, 4H). |
| 28 | 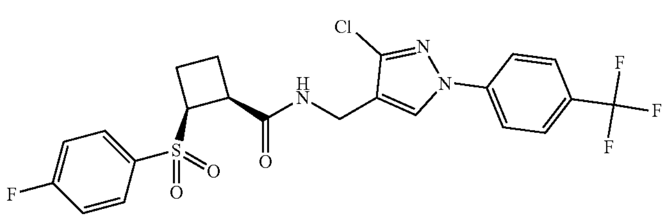 [SMILES: O=C(NCc1cn(-c2ccc(C(F)(F)F)cc2)nc1Cl)[C@@H]1CC[C@@H]1S(=O)(=O)c1ccc(F)cc1] | 0.0194 | $^1$H NMR (300 MHz, CDCl$_3$) δ 8.30 (s, 1H), 7.89-7.84 (m, 2H), 7.80-7.77 (m, 2H), 7.67-7.61 (m, 2H), 7.26-7.22 (m, 2H), 6.60-6.45 (s, 1H), 4.58-4.51 (m, 1H), 4.39-4.32 (m, 1H), 4.09-4.00 (m, 1H), 3.56-3.51 (m, 1H), 2.74-2.65 (m, 2H), 2.61-2.47 (m, 1H), 2.20-2.08 (m, 1H). |
| 29 | 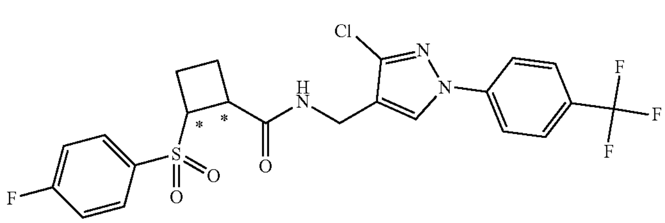 [SMILES: O=C(NCc1cn(-c2ccc(C(F)(F)F)cc2)nc1Cl)C1CCC1S(=O)(=O)c1ccc(F)cc1] | 0.0658 | $^1$H NMR (300 MHz, CDCl$_3$) δ 8.30 (s, 1H), 7.89-7.84 (m, 2H), 7.80-7.77 (m, 2H), 7.67-7.61 (m, 2H), 7.26-7.22 (m, 2H), 6.60-6.45 (s, 1H), 4.58-4.51 (m, 1H), 4.39-4.33 (m, 1H), 4.09-4.01 (m, 1H), 3.56-3.51 (m, 1H), 2.74-2.67 (m, 2H), 2.62-2.46 (m, 1H), 2.20-2.05 (m, 1H). |

TABLE 3-continued

| Ex | Structure | IC$_{50}$ | $^1$H NMR |
|---|---|---|---|
| 30 | 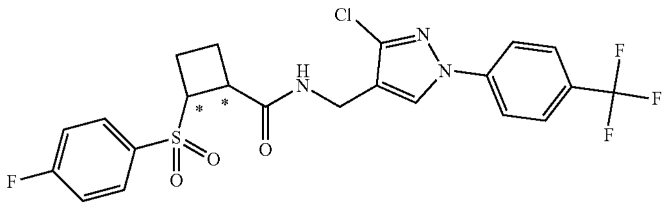 [SMILES: O=C(NCc1cn(-c2ccc(C(F)(F)F)cc2)nc1Cl)C1CCC1S(=O)(=O)c1ccc(F)cc1] | 0.0567 | $^1$H NMR (300 MHz, CDCl$_3$) δ 8.10 (s, 1H), 7.89-7.84 (m, 2H), 7.80-7.77 (m, 2H), 7.72-7.61 (m, 2H), 7.26-7.20 (m, 2H), 6.76-6.70 (s, 1H), 4.50-4.20 (m, 2H), 4.00-3.85 (m, 1H), 3.70-3.50 (m, 1H), 2.50-2.30 (m, 2H), 2.28-2.08 (m, 1H), 2.06-1.90 (m, 1H). |
| 31 | 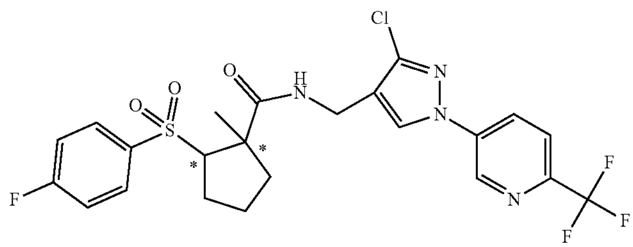 [SMILES: CC1(C(=O)NCc2cn(-c3ccc(C(F)(F)F)nc3)nc2Cl)CCCC1S(=O)(=O)c1ccc(F)cc1] | 0.0392 | $^1$H NMR (300 MHz, CDCl$_3$) δ 9.01 (s, 1H), 8.42 (s, 1H), 8.20-8.17 (m, 1H), 7.92-7.89 (m, 2H), 7.88-7.72 (m, 1H), 7.27-7.23 (m, 2H), 6.60 (s, 1H), 4.60-4.55 (m, 1H), 4.32-4.27 (m, 1H), 3.27-3.23 (m, 1H), 2.53-2.51 (m, 1H), 2.49-2.36 (m, 1H), 2.18-2.00 (m, 1H), 1.82-1.80 (m, 1H), 1.68-1.59 (m, 1H), 1.58 (s, 3H), 1.61-1.55 (m, 1H). |
| 32 | 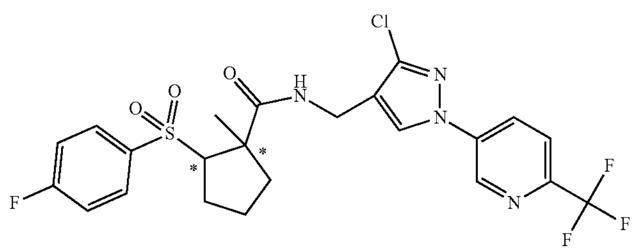 [SMILES: CC1(C(=O)NCc2cn(-c3ccc(C(F)(F)F)nc3)nc2Cl)CCCC1S(=O)(=O)c1ccc(F)cc1] | 0.0857 | $^1$H NMR (300 MHz, CDCl$_3$) δ 9.04 (s, 1H), 8.43 (s, 1H), 8.20-8.18 (m, 1H), 7.92-7.89 (m, 2H), 7.75-7.72 (m, 1H), 7.27-7.23 (m, 2H), 6.60 (s, 1H), 4.61-4.56 (m, 1H), 4.32-4.27 (m, 1H), 3.27-3.23 (m, 1H), 2.53-2.48 (m, 1H), 2.39-2.37 (m 1H), 2.18-2.10 (m, 1H), 1.82-1.68 (m, 2H), 1.68 (s, 3H), 1.55 (s, 1H). |
| 33 | 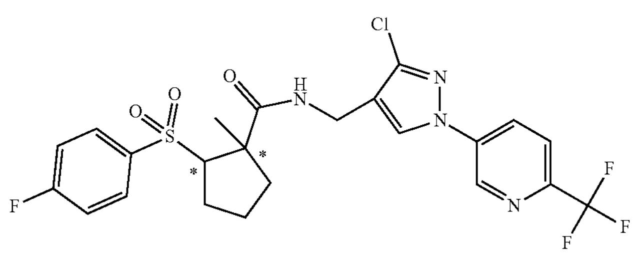 [SMILES: CC1(C(=O)NCc2cn(-c3ccc(C(F)(F)F)nc3)nc2Cl)CCCC1S(=O)(=O)c1ccc(F)cc1] | 0.0885 | $^1$H NMR (300 MHz, CDCl3) δ 9.08 (d, J = 12 Hz, 1H), 8.41 (s, 1H), 8.21-8.19 (m, 1H), 7.90-7.87 (m, 2H), 7.73-7.71 (m, 1H), 7.24-7.20 (m, 2H), 6.71 (s, 1H), 4.75-4.69 (m, 1H), 4.24-4.15 (m, 2H), 2.27-2.01 (m, 2H), 1.95-1.72 (m, 4H), 1.66 (s, 3H). |
| 34 | 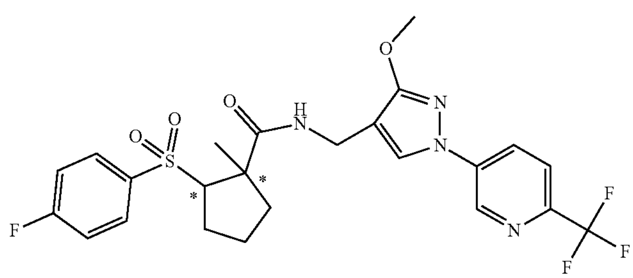 [SMILES: COc1nn(-c2ccc(C(F)(F)F)nc2)cc1CNC(=O)C1(C)CCCC1S(=O)(=O)c1ccc(F)cc1] | 0.0331 | $^1$H NMR (400 MHz, CDCl$_3$) δ 8.97 (s, 1H), 8.14 (s, 1H), 8.07-8.04 (m, 1H), 7.92-7.88 (m, 2H), 7.67 (d, J = 8.8 Hz, 1H), 7.25-7.21 (m, 2H), 6.53 (s, 1H), 4.45-4.40 (m, 1H), 4.28-4.23 (m, 1H), 4.03 (s, 3H), 3.27-3.23 (m, 1H), 2.52-2.47 (m, 1H), 2.46-2.37 (m, 1H), 2.12-2.11 (m, 1H), 1.84-1.82 (m, 1H), 1.81-1.68 (m, 1H), 1.59 (s, 3H), 1.57-1.54 (m, 1H). |
| 35 | 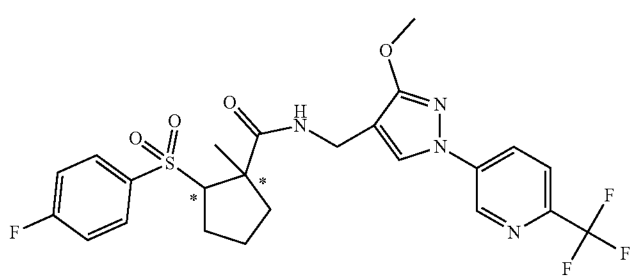 [SMILES: COc1nn(-c2ccc(C(F)(F)F)nc2)cc1CNC(=O)C1(C)CCCC1S(=O)(=O)c1ccc(F)cc1] | 0.199 | $^1$H NMR (400 MHz, CDCl$_3$) δ 8.97 (s, 1H), 8.14 (s, 1H), 8.07-8.04 (m, 1H), 7.92-7.88 (m, 2H), 7.67 (d, J = 8.4 Hz, 1H), 7.25-7.21 (m, 2H), 6.53-6.52 (m, 1H), 4.45-4.40 (m, 1H), 4.28-4.23 (m, 1H), 4.03 (s, 3H), 3.27-3.23 (m, 1H), 2.51-2.46 (m, 1H), 2.39-2.37 (m, 1H), 2.15-2.05 (m, 1H), 1.84-1.81 (m, 1H), 1.70-1.68 (m, 1H), 1.59 (s, 3H), 1.57-1.54 (m, 1H). |

TABLE 3-continued

| Ex | Structure | IC$_{50}$ | $^1$H NMR |
|---|---|---|---|
| 36 | 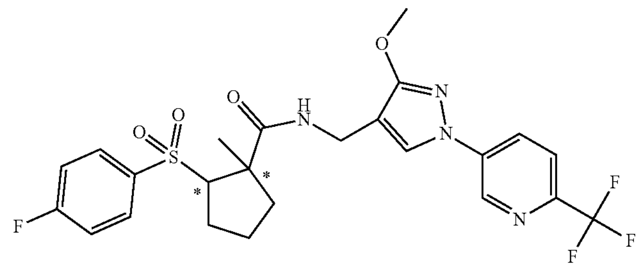 [SMILES: COc1nn(-c2ccc(C(F)(F)F)nc2)cc1CNC(=O)C1(C)CCCC1S(=O)(=O)c1ccc(F)cc1] | 0.0622 | $^1$H NMR (400 MHz, CDCl$_3$) δ 9.01 (s, 1H), 8.11-8.05 (m, 2H), 7.89-7.86 (m, 2H), 7.67 (d, J = 8.4 Hz, 1H), 7.20 (t, J = 8.8 Hz, 2H), 6.63-6.62 (m, 1H), 4.55-4.49 (m, 1H), 4.19-4.14 (m, 2H), 4.04 (s, 3H), 2.25-2.20 (m, 2H), 1.90-1.67 (m, 4H), 1.66 (s, 3H). |
| 37 | 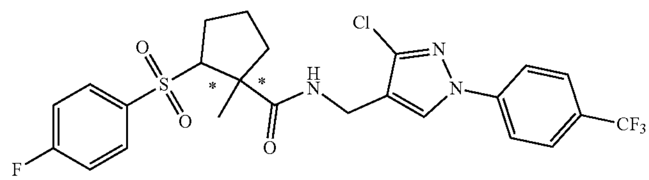 [SMILES: CC1(C(=O)NCc2cn(-c3ccc(C(F)(F)F)cc3)nc2Cl)CCCC1S(=O)(=O)c1ccc(F)cc1] | 0.0239 | $^1$H NMR (300 MHz, CDCl$_3$) δ 8.57 (s, 1H), 8.06-7.86 (m, 7H), 7.49-7.44 (m, 2H), 4.19-3.99 (m, 2H), 3.73-3.70 (m, 1H), 2.22-2.14 (m, 2H), 1.99-1.52 (m, 4H), 1.39 (s, 3H). |
| 38 | 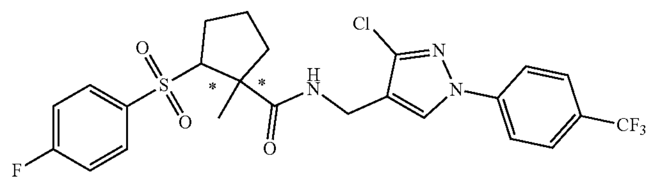 [SMILES: CC1(C(=O)NCc2cn(-c3ccc(C(F)(F)F)cc3)nc2Cl)CCCC1S(=O)(=O)c1ccc(F)cc1] | 0.0471 | $^1$H NMR (300 MHz, CDCl$_3$) δ 8.54 (s, 1H), 8.21 (m, 1H), 8.00-7.97 (m, 2H), 7.88-7.86 (m, 2H), 7.50-7.45 (m, 2H), 4.33-4.27 (m, 1H), 4.12-4.07 (m, 2H), 2.13-1.56 (m, 6H), 1.46 (s, 3H). |
| 39 | 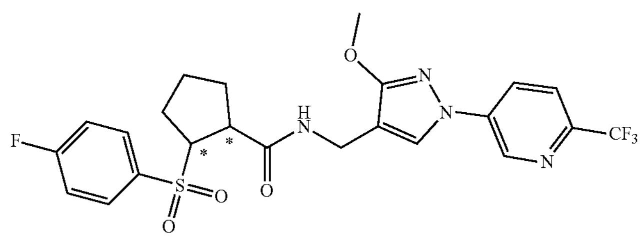 [SMILES: COc1nn(-c2ccc(C(F)(F)F)nc2)cc1CNC(=O)C1CCCC1S(=O)(=O)c1ccc(F)cc1] | 0.218 | $^1$H NMR (300 MHz, DMSO-d6) δ 9.11 (s, 1H), 8.46 (s, 1H), 8.29-8.26 (m, 1H), 8.15 (s, 1H), 8.00-7.88 (m, 3H), 7.49-7.43 (m, 2H), 4.02-3.79 (m, 6H), 2.99-2.97 (m, 1H), 2.26 (br, 1H), 1.87-1.63 (m, 5H) |
| 40 | 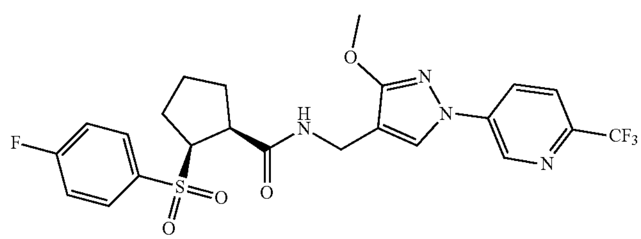 [SMILES: COc1nn(-c2ccc(C(F)(F)F)nc2)cc1CNC(=O)[C@@H]1CCC[C@@H]1S(=O)(=O)c1ccc(F)cc1] | 0.159 | $^1$H NMR (300 MHz, DMSO-d6) δ 9.14 (s, 1H), 8.37-8.26 (m, 3H), 8.01 7.90 (m, 3H), 7.44-7.38 (m, 2H), 4.04-3.90 (m, 6H), 3.09-3.06 (m, 1H), 2.07-1.97 (m, 3H), 1.68-1.59 (m, 3H). |
| 41 | 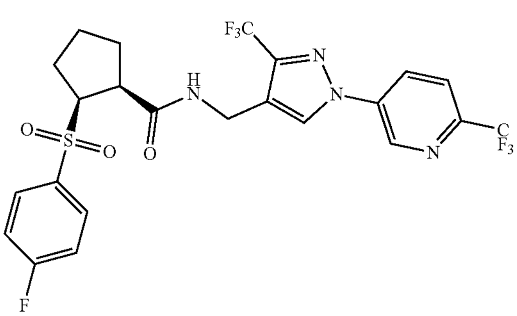 [SMILES: O=C(NCc1cn(-c2ccc(C(F)(F)F)nc2)nc1C(F)(F)F)[C@@H]1CCC[C@@H]1S(=O)(=O)c1ccc(F)cc1] | 0.0404 | $^1$H NMR (300 MHz, DMSO-d6) δ 9.28 (s, 1H), 8.73 (s, 1H), 8.54-8.49 (m, 2H), 8.15-8.12 (m, 1H), 7.96-7.91 (m, 2H), 7.44-7.38 (m, 2H), 4.22-4.02 (m, 3H), 3.14-3.06 (m, 1H), 2.09-1.92 (m, 3H), 1.71-1.55 (m, 3H). |

TABLE 3-continued

| Ex | Structure | IC$_{50}$ | $^1$H NMR |
|---|---|---|---|
| 42 | 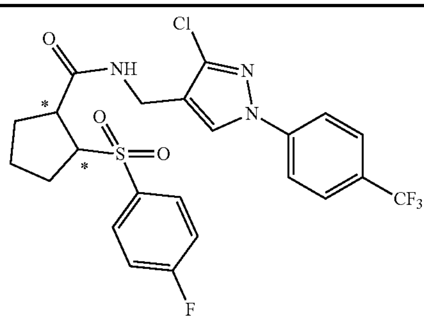 | 0.0455 | $^1$H NMR (300 MHz, CDCl$_3$) δ 8.33 (s, 1H), 7.93-7.88 (m, 2H), 7.79 (d, J = 8.7 Hz, 2H), 7.66 (d, J = 8.4 Hz, 2H), 7.26-7.22 (m, 2H), 6.33 (s, 1H), 4.54-4.47 (m, 1H), 4.33-4.26 (m, 1H), 3.57-3.52 (m, 1H), 3.15 (s, 1H), 2.36-2.21 (m, 3H), 1.83-1.71 (m, 3H). |
| 43 | 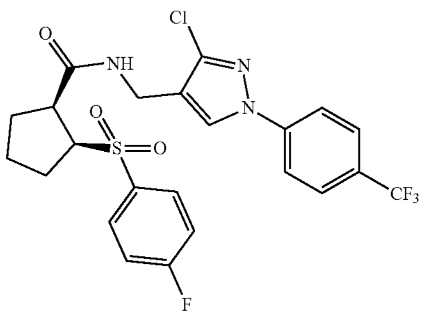 [SMILES: O=C(NCc1cn(-c2ccc(C(F)(F)F)cc2)nc1Cl)[C@@H]1CCC[C@@H]1S(=O)(=O)c1ccc(F)cc1] | 0.0389 | $^1$H NMR (300 MHz, CDCl$_3$) δ 8.08 (s, 1H), 7.92-7.89 (m, 2H), 7.79 (d, J = 8.4 Hz, 2H), 7.69 (d, J = 8.4 Hz, 2H), 7.29 (t, J = 8.4 Hz, 2H), 6.55 (s, 1H), 4.49-4.42 (m, 1H), 4.25-4.18 (m, 1H), 3.87-3.79 (m, 1H), 3.26-3.18 (m, 1H), 2.07-1.95 (m, 3H), 1.89-1.73 (m, 3H). |

It is to be understood that the invention is not limited to the particular embodiments of the invention described above, as variations of the particular embodiments may be made and still fall within the scope of the appended claims. All documents cited to or relied upon herein are expressly incorporated by reference.

The invention claimed is:

1. A compound of formula (I) or a pharmaceutically acceptable salt thereof:

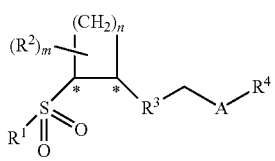

wherein:
n is 2 or 3;
R$^1$ is aryl or heteoraryl, each optionally substituted with one or more groups independently selected from halogen, —CN, —C$_{1-6}$ alkyl and —C$_{1-6}$ haloalkyl;
m is 0, 1, 2, or 3;
each R$^2$ is independently selected from halogen, —C$_{1-6}$ alkyl, —C$_{1-6}$ haloalkyl, —O—C$_{1-6}$ alkyl, —C$_{3-7}$ cycloalkyl, and —CN;
R$^3$ is an amide selected from the orientation —NH—C(O)— and —C(O)—NH—;
R$^4$ is a 4, 5, 6 or 7-membered heterocycle, aryl or heteroaryl optionally substituted with one or more groups independently selected from halogen, —C$_{1-6}$ alkyl, —C$_{1-6}$ haloalkyl, —O—C$_{1-6}$ haloalkyl, and —CN;

A is selected from A$^1$, A$^2$ and A$^3$ wherein:
A$^1$ is unsubstituted or substituted 5-membered heteroaryl comprising one or two nitrogen hetero atoms;
A$^2$ is unsubstituted or substituted aryl; and
A$^3$ is unsubstituted or substituted 6-membered heteroaryl comprising one or two hetero nitrogen atoms; and
each * independently denotes a chiral center (i) in an R configuration or in an S configuration or (ii) a mixture of R and S configurations for a plurality of compounds of formula (I).

2. The compound of claim 1 wherein n is 2.

3. The compound of claim 1 wherein n is 3.

4. The compound of claim 1 wherein R$^1$ is aryl substituted with a substituent selected from Br, Cl, F, —CHF$_2$, —CF$_3$, CHCl$_2$ and —CCl$_3$ at any of the ortho, meta or para positions.

5. The compound of claim 4 wherein R$^1$ is:

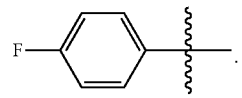 [SMILES: *c1ccc(F)cc1]

6. The compound of claim 1 wherein m is 0.

7. The compound of claim 1 wherein m is 1 or 2 and wherein each R$^2$ is independently selected from —CH$_3$, —CH$_2$CH$_3$, —CH$_2$-cyclopropane, —CF$_3$, —CN and F.

8. The compound of claim 1 wherein R$^3$ is —NH—C(O)—.

9. The compound of claim 1 wherein R$^3$ is —C(O)—NH—.

10. The compound of claim 1 wherein A is A$^1$, wherein A$^1$ is selected from:

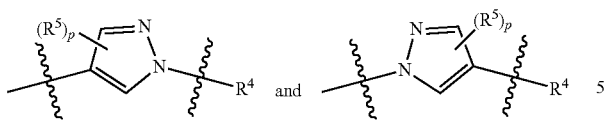

wherein p is 0 or 1 and wherein $R^5$ is selected from halogen, —O—$C_{1-6}$ alkyl, —$C_{1-6}$ haloalkyl and —$C_{3-7}$ cycloalkyl.

11. The compound of claim 10 wherein $A^1$ is selected from:

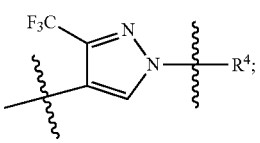 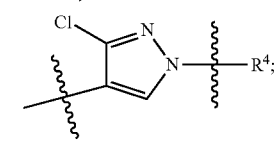

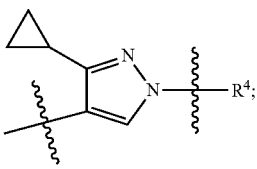 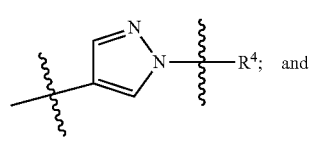

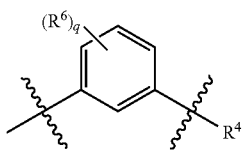

12. The compound of claim 1 wherein A is $A^2$, wherein $A^2$ is of the structure:

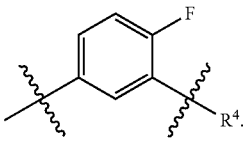

wherein q is 0, 1 or 2, and wherein each $R^6$, when present, is independently selected from halogen, O—$C_{1-6}$ alkyl and $C_{1-6}$ haloalkyl.

13. The compound of claim 12 wherein $A^2$ is:

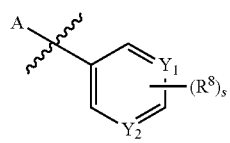

14. The compound of claim 1 wherein A is $A^3$, wherein $A^3$ is of the structure:

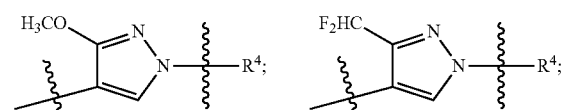

wherein:
(1) $X_1$, $X_2$ and $X_3$ are independently selected from C and N wherein
  (i) one of $X_1$, $X_2$ and $X_3$ is N and r is 0, 1 or 2, or
  (ii) $X_1$ and $X_3$ are each N and r is 0 or 1; and
(2) each $R^7$ is independently selected from halogen, O—$C_{1-6}$ alkyl, and $C_{1-6}$ haloalkyl.

15. The compound of claim 14 wherein $A^3$ is selected from:

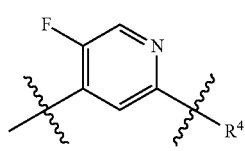 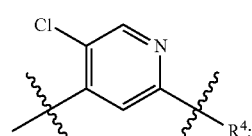

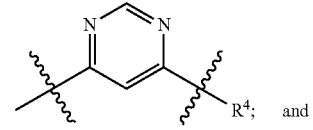 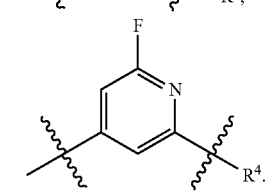

16. The compound of claim 1 wherein $R^4$ is:

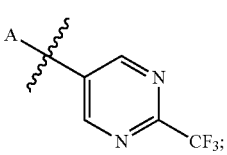

wherein:
$Y_1$ and $Y_2$ are independently selected from C and N;
s is 0 or 1; and
each $R^8$ is independently selected from halogen, —O—$C_{1-6}$ haloalkyl, and —$C_{1-6}$ haloalkyl.

17. The compound of claim 16 wherein $R^4$ is selected from:

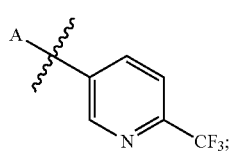 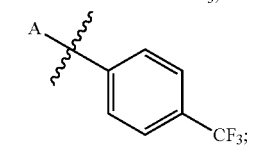

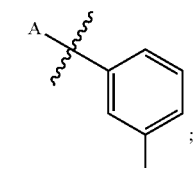

101
-continued
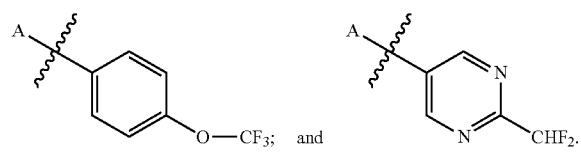
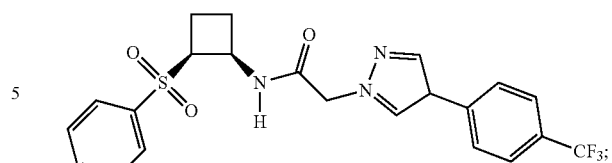 and
18. A compound of claim 1 selected from:
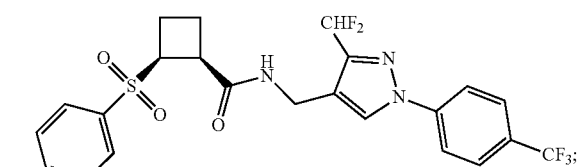
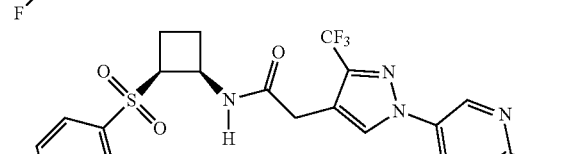
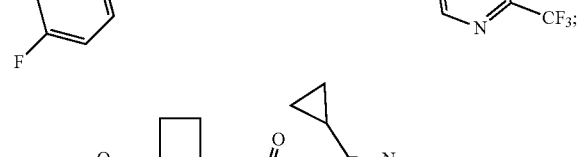
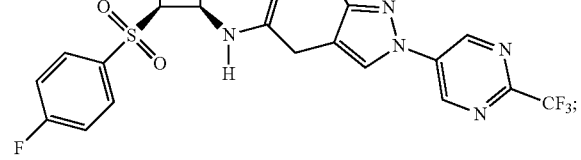
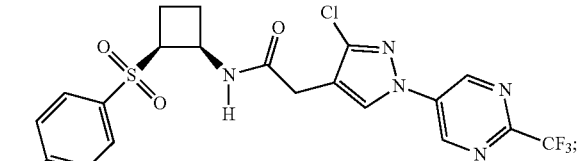
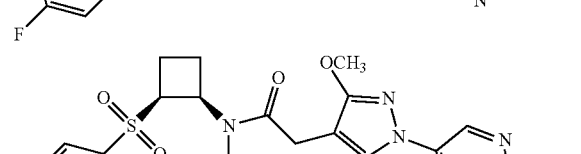
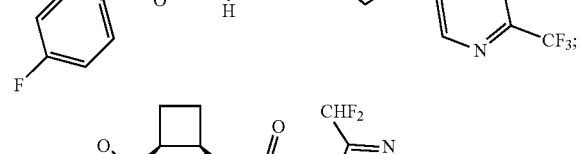
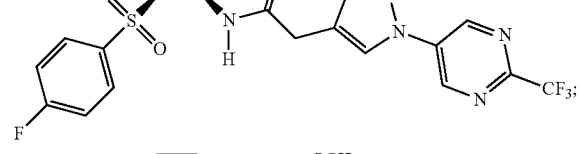
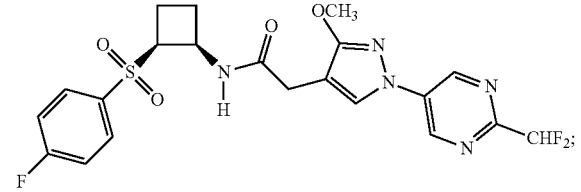
102
-continued
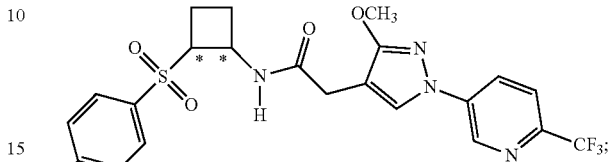
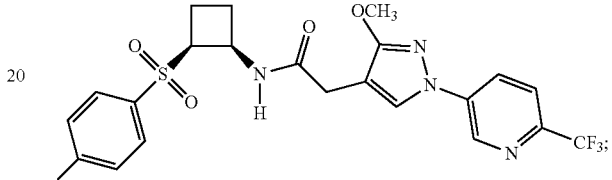
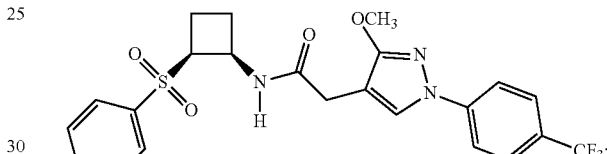
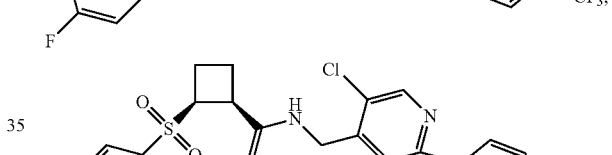
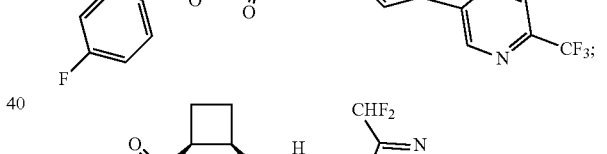
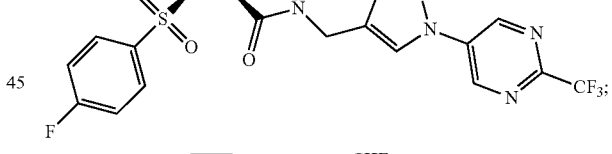
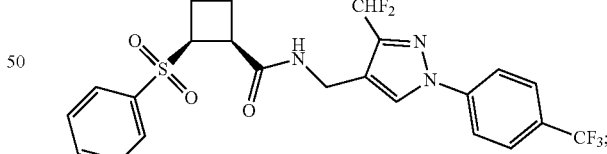
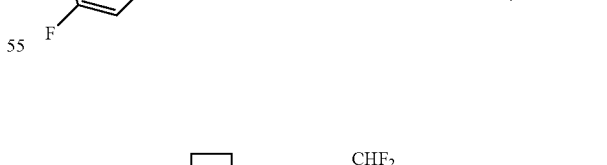
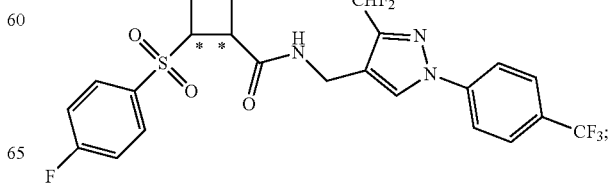

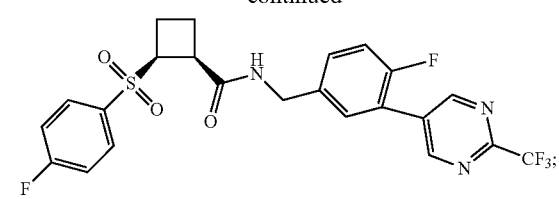
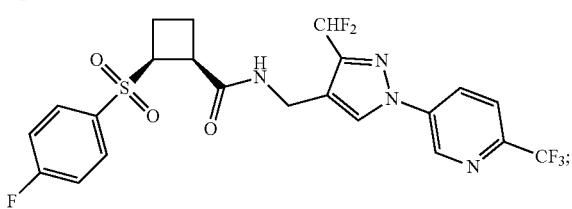
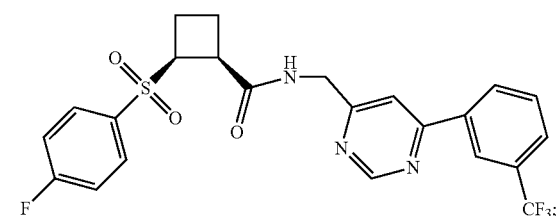
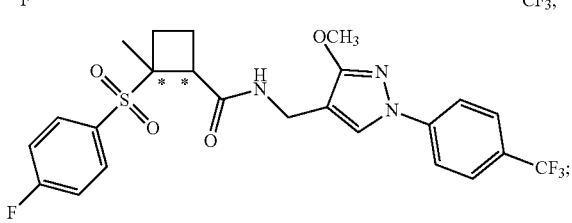
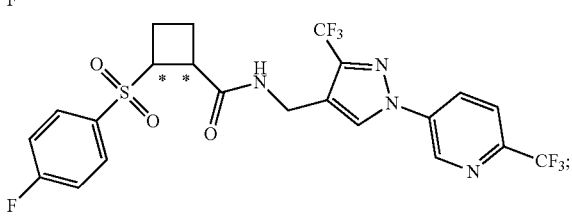
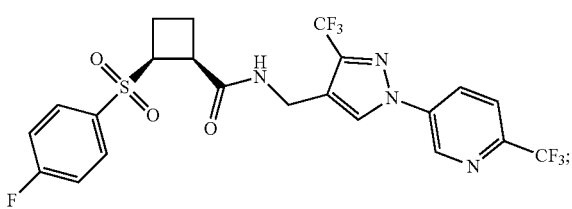 [SMILES: O=C(NCc1cn(-c2ccc(C(F)(F)F)cc2)nc1Cl)C1CCC1S(=O)(=O)c1ccc(F)cc1]
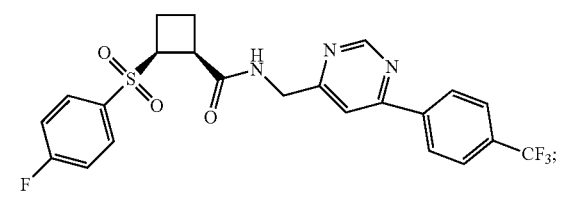
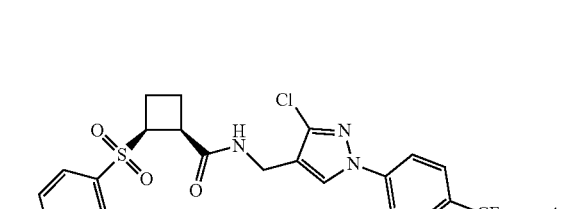 and
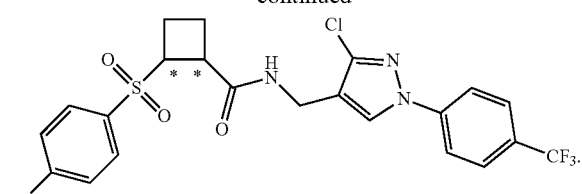
19. A compound of claim 1 selected from:
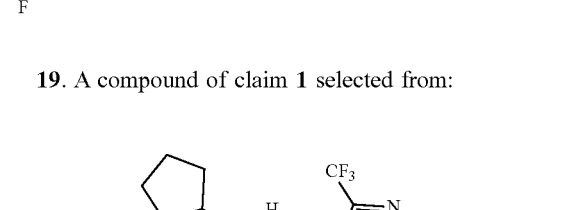
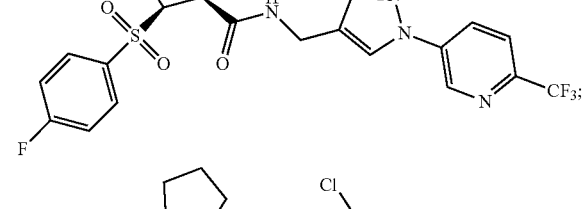
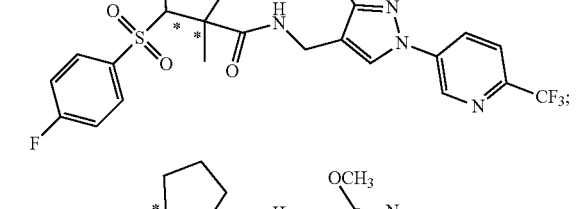
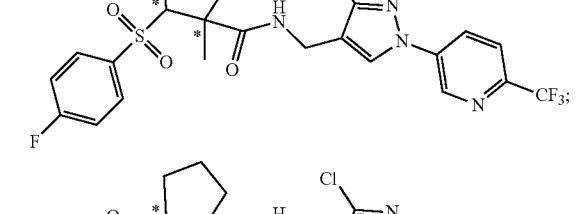
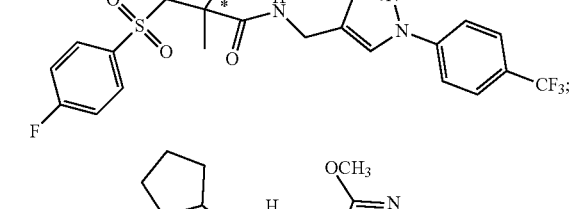
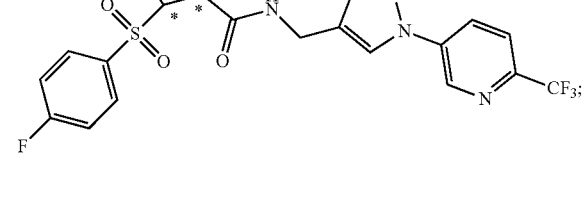

-continued
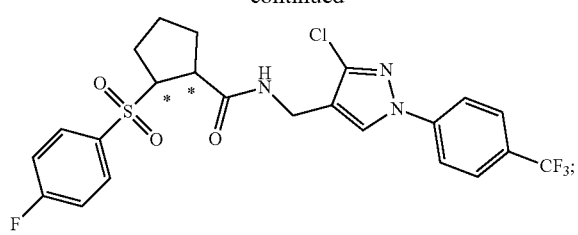
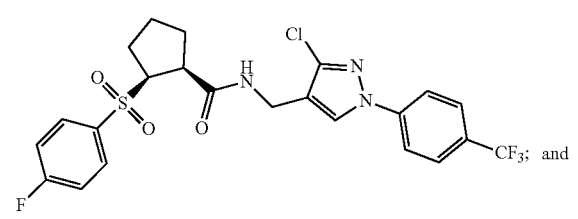 and
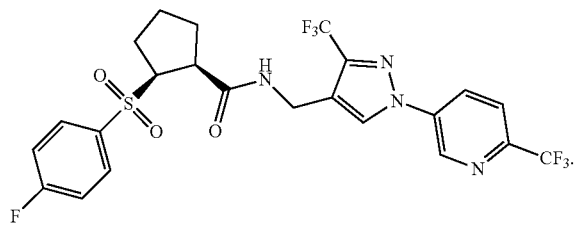
20. A compound selected from:
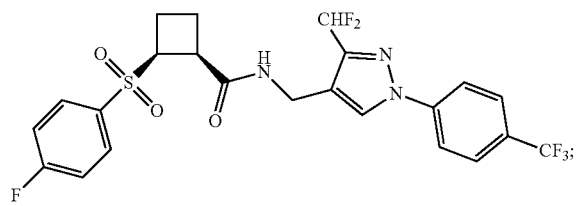
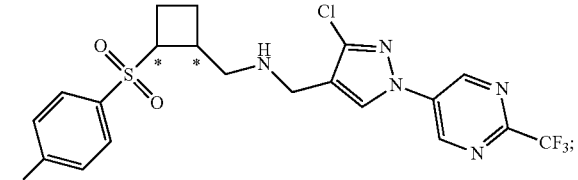
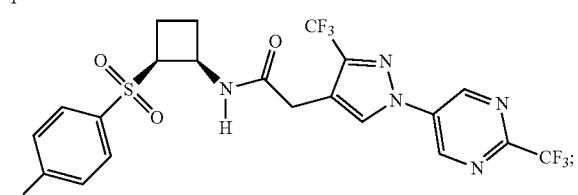
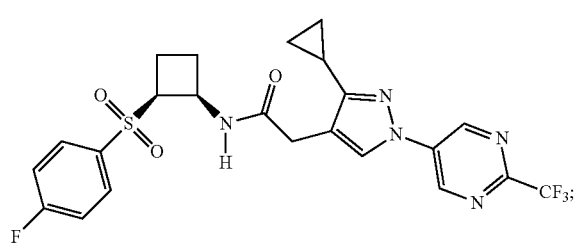
-continued
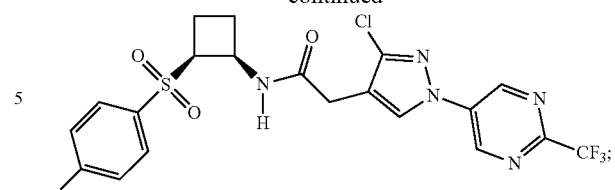
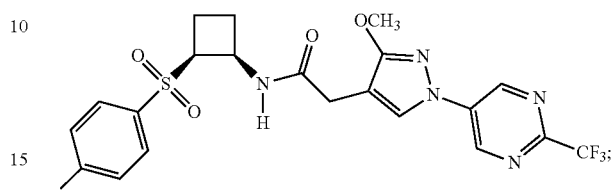
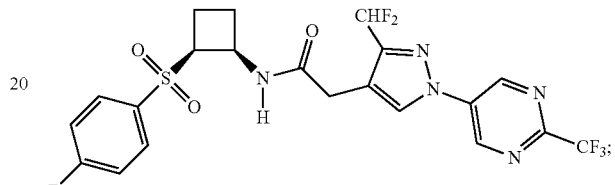
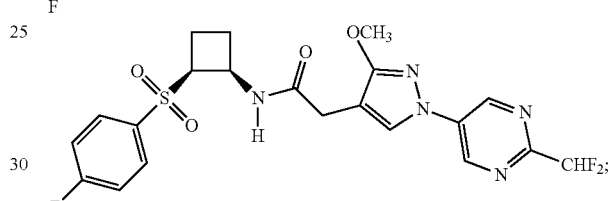
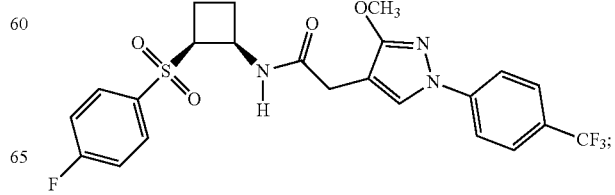

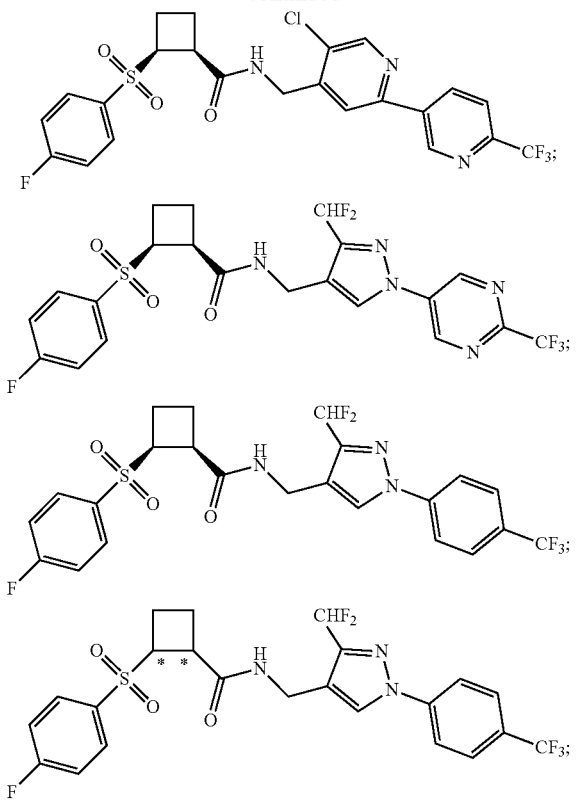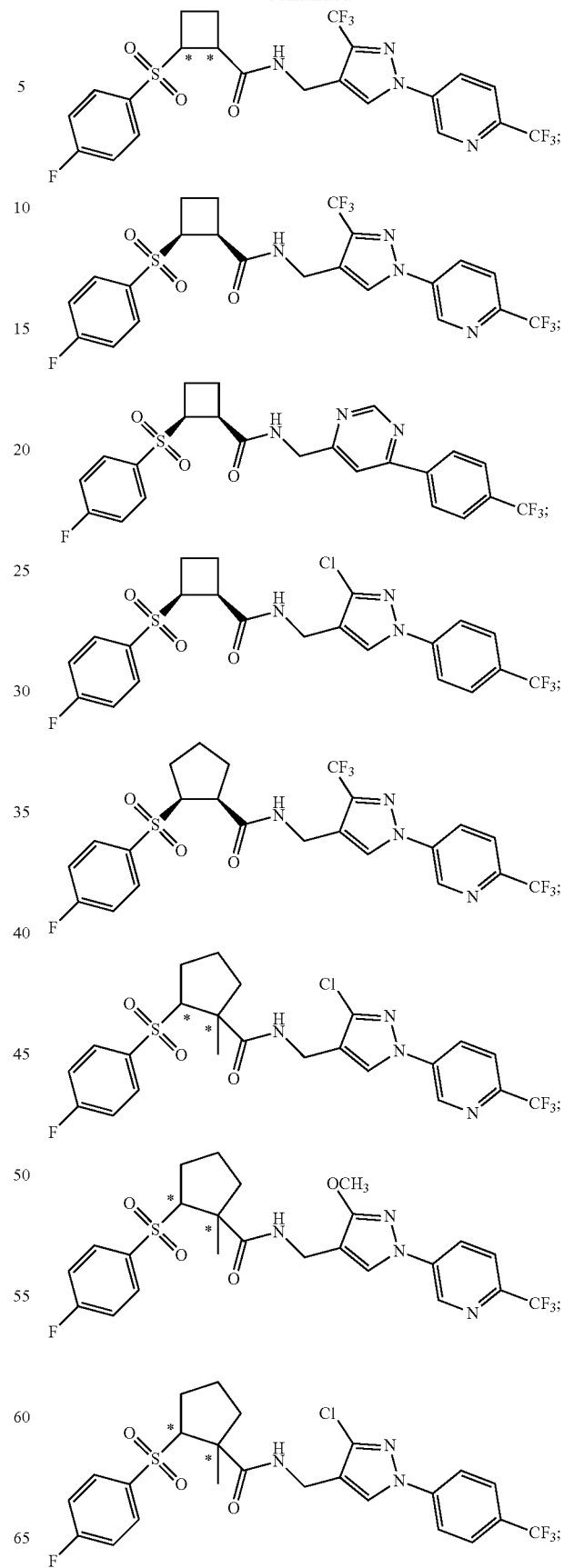

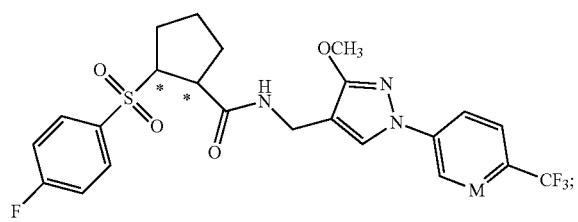
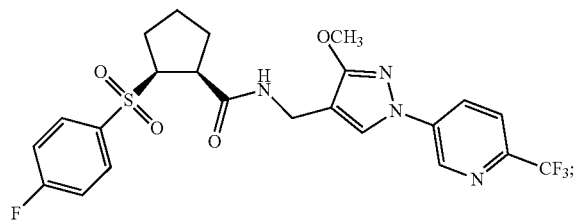
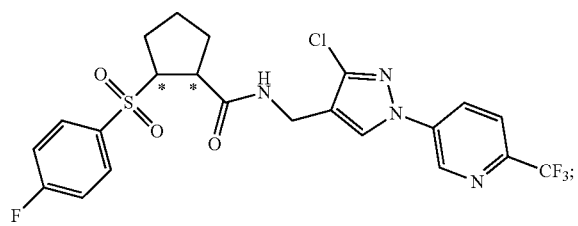
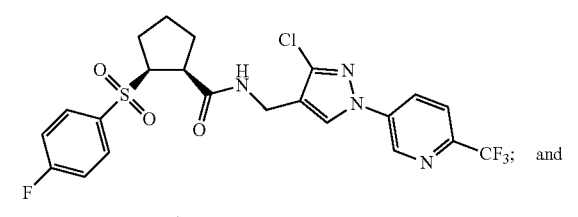
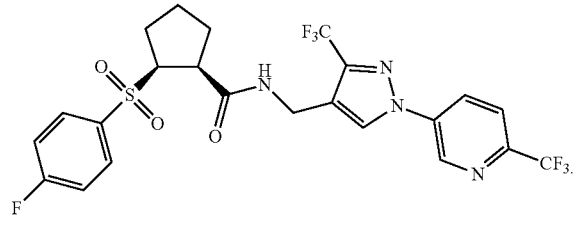
21. A compound selected from:
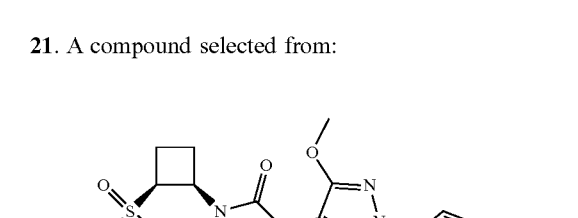
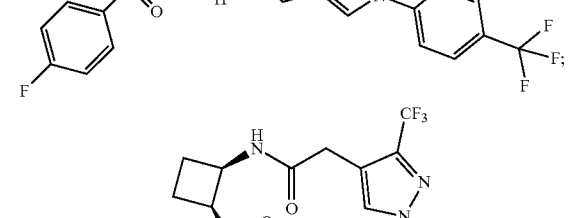
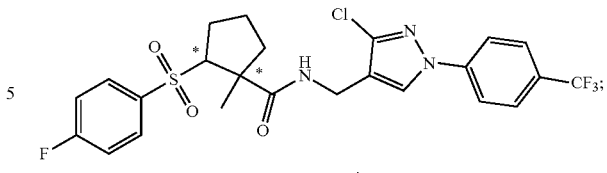
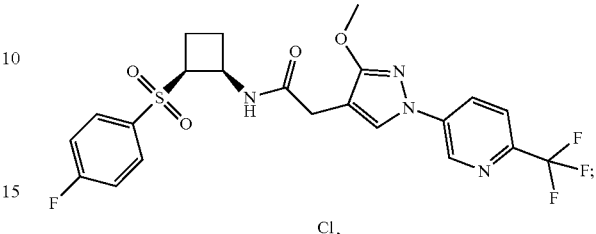
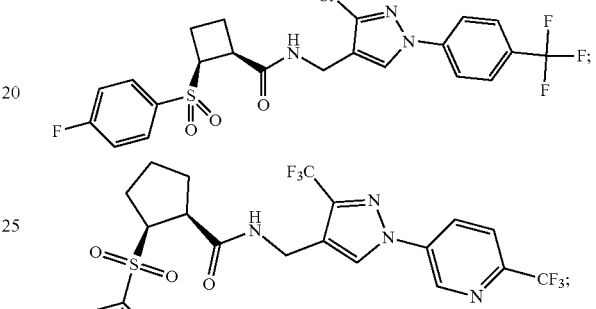
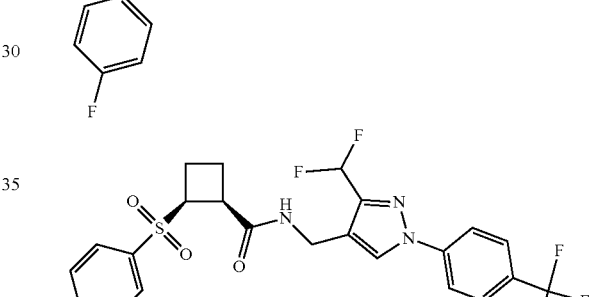
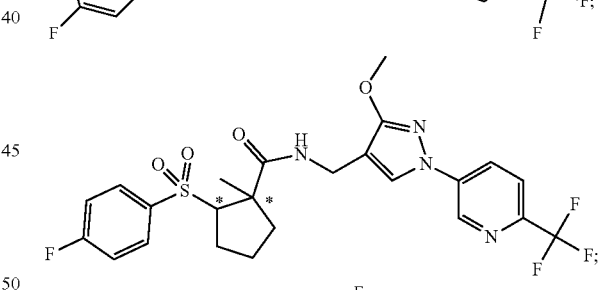
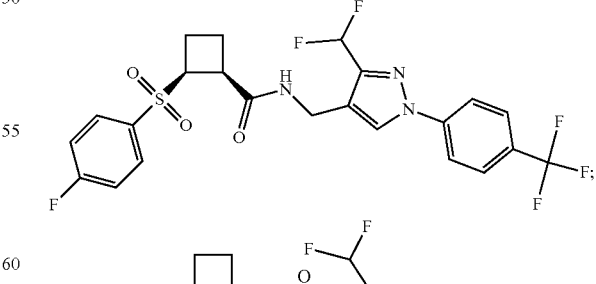
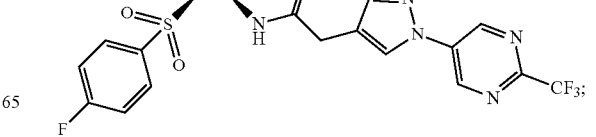

111
-continued
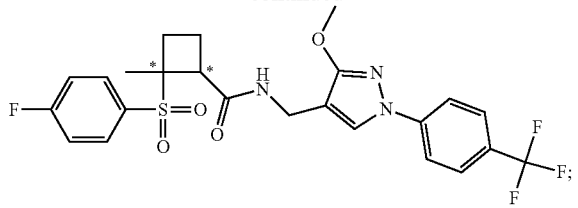
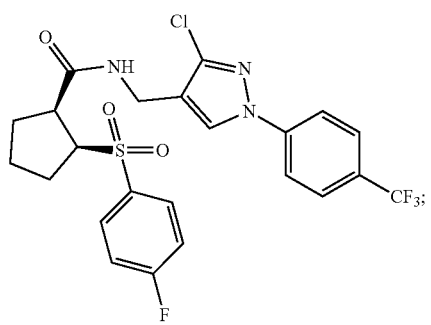
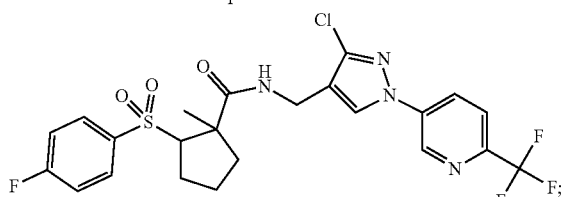
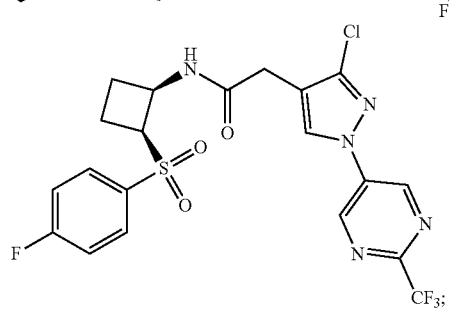
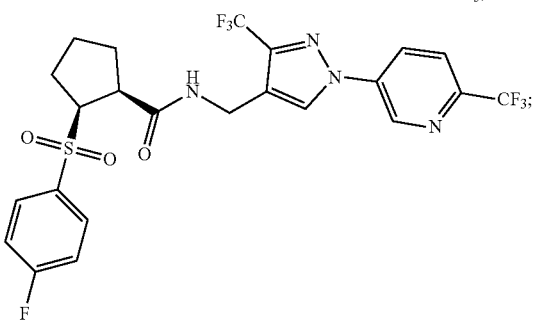
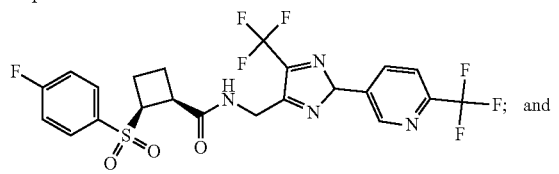; and
112
-continued
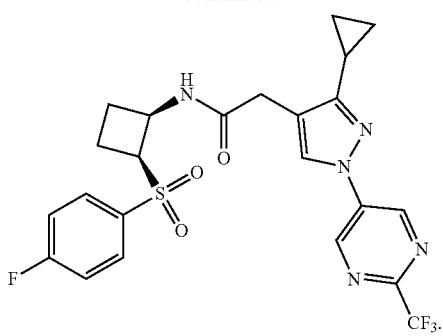
22. A compound selected from:
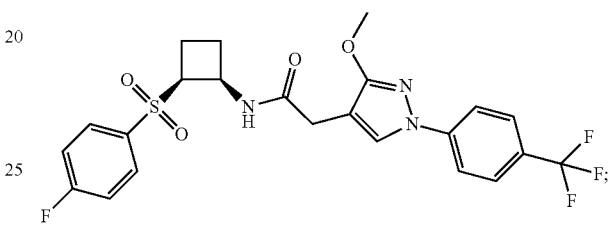
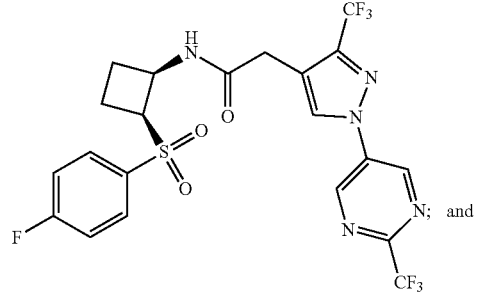; and
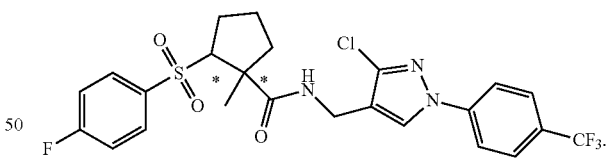
23. A pharmaceutical composition, comprising a compound as described in any one of claim 1 or a pharmaceutically acceptable salt thereof, and a pharmaceutically acceptable carrier, diluent or excipient.
* * * * *